US011390909B2

(12) United States Patent
Lamble et al.

(10) Patent No.: US 11,390,909 B2
(45) Date of Patent: Jul. 19, 2022

(54) NUCLEIC ACID DETECTION METHOD

(71) Applicant: Sense Biodetection Limited, Abingdon (GB)

(72) Inventors: Henry John Lamble, Abingdon (GB); Christopher Egan, Abingdon (GB); David Lloyd, Abingdon (GB); Eryk Dunski, Abingdon (GB)

(73) Assignee: Sense Biodetection Limited, Abingdon (GB)

( * ) Notice: Subject to any disclaimer, the term of this patent is extended or adjusted under 35 U.S.C. 154(b) by 317 days.

(21) Appl. No.: 15/747,130

(22) PCT Filed: Jul. 22, 2016

(86) PCT No.: PCT/GB2016/052265
§ 371 (c)(1),
(2) Date: Jan. 23, 2018

(87) PCT Pub. No.: WO2017/017424
PCT Pub. Date: Feb. 2, 2017

(65) Prior Publication Data
US 2018/0216157 A1 Aug. 2, 2018

(30) Foreign Application Priority Data
Jul. 24, 2015 (GB) .................................... 1513128

(51) Int. Cl.
*C12Q 1/68* (2018.01)
*C12Q 1/682* (2018.01)
*C07H 21/04* (2006.01)

(52) U.S. Cl.
CPC .............. *C12Q 1/682* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 5,011,769 A | 4/1991 | Duck et al. | |
| 5,200,313 A * | 4/1993 | Carrico ................... | C12Q 1/68 435/6.11 |
| 5,403,711 A | 4/1995 | Walder et al. | |
| 6,444,661 B1 * | 9/2002 | Barton .................. | C07F 15/008 514/185 |
| 2009/0011943 A1 * | 1/2009 | Drmanac ............... | C12N 15/64 506/4 |
| 2019/0002971 A1 * | 1/2019 | Koslover ............... | G01N 33/48 |

FOREIGN PATENT DOCUMENTS

| | | |
|---|---|---|
| WO | 97/12062 A1 | 4/1997 |
| WO | 99/01569 A2 | 1/1999 |
| WO | 03/054214 A2 | 7/2003 |
| WO | 2005052127 A2 | 6/2005 |
| WO | 2006088910 A2 | 8/2006 |
| WO | 2010096202 A2 | 8/2010 |

OTHER PUBLICATIONS

"Oligonucleotide definition," Merriam-Webster.com; accessed Aug. 23, 2017. (Year: 2017).*
"Oligonucleotide", Wikipedia.com, accessed Feb. 17, 2019. (Year: 2019).*
"Viruses", Wikipedia.com, accessed Nov. 24, 2012. (Year: 2012).*
"How many species of bacteria are there", wisegeek.com; accessed Jan. 21, 2014. (Year: 2014).*
"Fungi," Wikipedia.com; accessed Jun. 3, 2013. (Year: 2013).*
"Plant," Wikipedia.com; accessed Aug. 28, 2015. (Year: 2015).*
"Mammal," Wikipedia.com; accessed Sep. 22, 2011. (Year: 2011).*
"Murinae," Wikipedia.com, accessed Mar. 18, 2013. (Year: 2013).*
"Fish," Wikipedia.com, accessed Nov. 2, 2014. (Year: 2014).*
"Archaea," Wikipedia.com, accessed May 11, 2016. (Year: 2016).*
"Algae," Wikipedia.com, accessed Mar. 4, 2016. (Year: 2016).*
"Protozoa," Wikipedia.com, accessed May 11, 2016. (Year: 2016).*
Zeberg et al., "The major genetic risk factor for severe COVID-19 is inherited from Neanderthals", Nature, Sep. 30, 2020. (Year: 2020).*
Forster et al., "A human gut bacterial genome and culture collection for improved metagenomic analyses", Nature Biotechnology, vol. 37, Feb. 2019, 186-12. (Year: 2019).*
Sah et al., "Complete Genome Sequence of a 2019 Novel Coronavirus (SARS-CoV-2) Strain Isolated in Nepal" Microbiology, vol. 9, Issue 11, Mar. 12, 2020. (Year: 2020).*
Gabbatiss et al., "New form of DNA discovered inside living human cells", The Independent, Apr. 24, 2018, pp. 1-3. (Year: 2018).*
Craw et al., "Isothermal nucleic acid amplification technologies for point-of-care diagnostics: a critical review," Lab Chip, 2012, vol. 12, No. 14, 18 pages.

* cited by examiner

Primary Examiner — Bradley L. Sisson
(74) Attorney, Agent, or Firm — Morgan, Lewis & Bockius LLP

(57) ABSTRACT

The present invention relates to methods for the detection of nucleic acids of defined sequence, and compositions and kits for use in said methods. The methods employ nicking agent(s) and a sequential series of oligonucleotide probes to produce probe fragments in the presence of a target nucleic acid.

20 Claims, 17 Drawing Sheets
Specification includes a Sequence Listing.

Target Nucleic Acid    −    +    −    +

← Probe Fragment

← Oligonucleotide Probe

Cleavage Products

Probe Fragment:
100pmol
10pmol
0.1pmol
0.01pmol
—

Target Nucleic Acid:
25fmol
2.5fmol
—

1. Nt.BstNBI
2. Nt.CviPII
3. Nt.BsmAI
4. Nb.BtsI
5. Nb.BsrDI

Bacterial Nucleic Acid Target:   −   −   +   +
Viral Nucleic Acid Target:          −   +   −   +

← Bacterial Positive Test Result
← Viral Positive Test Result

Viral Nucleic Acid Target:          −   +   −   +
Bacterial Nucleic Acid Target:   −   −   +   +

← Bacterial Positive Test Result
← Viral Positive Test Result

SEQUENCE LISTING

```
<160> NUMBER OF SEQ ID NOS: 31

<210> SEQ ID NO 1
<211> LENGTH: 47
<212> TYPE: DNA
<213> ORGANISM: Artificial Sequence
<220> FEATURE:
<223> OTHER INFORMATION: Oligonucleotide Probe 1

<400> SEQUENCE: 1
gcatctctat gactcaagag tctgtccatc acgatatata tatatat        47

<210> SEQ ID NO 2
<211> LENGTH: 15
<212> TYPE: DNA
<213> ORGANISM: Artificial Sequence
<220> FEATURE:
<223> OTHER INFORMATION: Oligonucleotide Probe 2

<400> SEQUENCE: 2
gtgatggaca gactc                                           15

<210> SEQ ID NO 3
<211> LENGTH: 43
<212> TYPE: DNA
<213> ORGANISM: Artificial Sequence
<220> FEATURE:
<223> OTHER INFORMATION: Oligonucleotide Probe 3

<400> SEQUENCE: 3
atatatatat atatatttga gtcatagaga tgccgagact cct            43

<210> SEQ ID NO 4
<211> LENGTH: 57
<212> TYPE: DNA
<213> ORGANISM: Artificial Sequence
<220> FEATURE:
<223> OTHER INFORMATION: Oligonucleotide Probe 4

<400> SEQUENCE: 4
atatatatat atatgtaaaa gagtctgtcc atcacttctg tatctgggac tctaaag    57

<210> SEQ ID NO 5
```

```
<211> LENGTH: 57
<212> TYPE: DNA
<213> ORGANISM: Artificial Sequence
<220> FEATURE:
<223> OTHER INFORMATION: Oligonucleotide Probe 5

<400> SEQUENCE: 5
atatatatat atatctttag agtcccagat acagattatg caagtgatga ctcatag        57

<210> SEQ ID NO 6
<211> LENGTH: 44
<212> TYPE: DNA
<213> ORGANISM: Artificial Sequence
<220> FEATURE:
<223> OTHER INFORMATION: Oligonucleotide Probe 6

<400> SEQUENCE: 6
gaatcgagac gaaaagagtc tgtccatcac atatatatat atat                      44

<210> SEQ ID NO 7
<211> LENGTH: 44
<212> TYPE: DNA
<213> ORGANISM: Artificial Sequence
<220> FEATURE:
<223> OTHER INFORMATION: Oligonucleotide Probe 7

<400> SEQUENCE: 7
atatatatat atattttcgt ctcgattcga tatcttgact cctt                      44

<210> SEQ ID NO 8
<211> LENGTH: 40
<212> TYPE: DNA
<213> ORGANISM: Artificial Sequence
<220> FEATURE:
<223> OTHER INFORMATION: Oligonucleotide Probe 8

<400> SEQUENCE: 8
atatatatat aggagtctcg gcatctatat atatatatat                           40

<210> SEQ ID NO 9
<211> LENGTH: 46
<212> TYPE: DNA
<213> ORGANISM: Artificial Sequence
<220> FEATURE:
<223> OTHER INFORMATION: Oligonucleotide Probe 9

<400> SEQUENCE: 9
atatatatat atatctatga gtcatcactt gcataaatat atatat                    46

<210> SEQ ID NO 10
<211> LENGTH: 40
<212> TYPE: DNA
<213> ORGANISM: Artificial Sequence
<220> FEATURE:
<223> OTHER INFORMATION: Oligonucleotide Probe 10

<400> SEQUENCE: 10
atatatatat attaaaccaa gtaccgcact atatatatat                           40

<210> SEQ ID NO 11
<211> LENGTH: 22
<212> TYPE: DNA
<213> ORGANISM: Artificial Sequence
<220> FEATURE:
<223> OTHER INFORMATION: Oligonucleotide Probe 11

<400> SEQUENCE: 11
```
tgccatccac cttatgtata ta                                              22

<210> SEQ ID NO 12
<211> LENGTH: 44
<212> TYPE: DNA
<213> ORGANISM: Artificial Sequence
<220> FEATURE:
<223> OTHER INFORMATION: Oligonucleotide Probe 12

<400> SEQUENCE: 12
atatatatat ataggagt ctcggcatct atatatatat atat                        44

<210> SEQ ID NO 13
<211> LENGTH: 41
<212> TYPE: DNA
<213> ORGANISM: Artificial Sequence
<220> FEATURE:
<223> OTHER INFORMATION: Oligonucleotide Probe 13

<400> SEQUENCE: 13
atatatatat gtaaaagagt ctgtccatca ctatatatat a                         41

<210> SEQ ID NO 14
<211> LENGTH: 37
<212> TYPE: DNA
<213> ORGANISM: Artificial Sequence
<220> FEATURE:
<223> OTHER INFORMATION: Oligonucleotide Probe 14

<400> SEQUENCE: 14
tttttttttt tttttgagag ccaggaccag gaacaca                              37

<210> SEQ ID NO 15
<211> LENGTH: 37
<212> TYPE: DNA
<213> ORGANISM: Artificial Sequence
<220> FEATURE:
<223> OTHER INFORMATION: Oligonucleotide Probe 15

<400> SEQUENCE: 15
tttttttttt tttttgtgt tcctggtcct ggctctc                               37

<210> SEQ ID NO 16
<211> LENGTH: 42
<212> TYPE: DNA
<213> ORGANISM: Artificial Sequence
<220> FEATURE:
<223> OTHER INFORMATION: Oligonucleotide Probe 16

<400> SEQUENCE: 16
atatatatat gtaaaagagt ctgtccatca ctatatatat at                        42

<210> SEQ ID NO 17
<211> LENGTH: 42
<212> TYPE: DNA
<213> ORGANISM: Artificial Sequence
<220> FEATURE:
<223> OTHER INFORMATION: Oligonucleotide Probe 17

<400> SEQUENCE: 17
aaaaaaaaaa gtaaaagagt ctgtccatca ctaaaaaaaa aa                        42

<210> SEQ ID NO 18
<211> LENGTH: 39
<212> TYPE: DNA

```
<213> ORGANISM: Artificial Sequence
<220> FEATURE:
<223> OTHER INFORMATION: Oligonucleotide Probe 18

<400> SEQUENCE: 18
aaaaaaaaaa aaaagagtct gtccatcaca aaaaaaaaa                    39

<210> SEQ ID NO 19
<211> LENGTH: 37
<212> TYPE: DNA
<213> ORGANISM: Artificial Sequence
<220> FEATURE:
<223> OTHER INFORMATION: Oligonucleotide Probe 19

<400> SEQUENCE: 19
aaaaaaaaaa aagagtctgt ccatcacaaa aaaaaaa                      37

<210> SEQ ID NO 20
<211> LENGTH: 35
<212> TYPE: DNA
<213> ORGANISM: Artificial Sequence
<220> FEATURE:
<223> OTHER INFORMATION: Oligonucleotide Probe 20

<400> SEQUENCE: 20
aaaaaaaaaa aagagtctgt ccatcaaaaa aaaaa                        35

<210> SEQ ID NO 21
<211> LENGTH: 25
<212> TYPE: DNA
<213> ORGANISM: Artificial Sequence
<220> FEATURE:
<223> OTHER INFORMATION: Oligonucleotide Probe 21

<400> SEQUENCE: 21
attaatacca tcaaaatgta tatat                                   25

<210> SEQ ID NO 22
<211> LENGTH: 21
<212> TYPE: DNA
<213> ORGANISM: Artificial Sequence
<220> FEATURE:
<223> OTHER INFORMATION: Oligonucleotide Probe 22

<400> SEQUENCE: 22
atatatacat tttgatggta t                                       21

<210> SEQ ID NO 23
<211> LENGTH: 21
<212> TYPE: DNA
<213> ORGANISM: Artificial Sequence
<220> FEATURE:
<223> OTHER INFORMATION: Oligonucleotide Probe 23

<400> SEQUENCE: 23
atatatacat tttgaaggta t                                       21

<210> SEQ ID NO 24
<211> LENGTH: 13
<212> TYPE: DNA
<213> ORGANISM: Artificial Sequence
<220> FEATURE:
<223> OTHER INFORMATION: Oligonucleotide Probe 24

<400> SEQUENCE: 24
attttgatgg tat                                                13
```

<210> SEQ ID NO 25
<211> LENGTH: 102
<212> TYPE: DNA
<213> ORGANISM: Artificial Sequence
<220> FEATURE:
<223> OTHER INFORMATION: Oligonucleotide Probe 25

<400> SEQUENCE: 25
ttactgagga tattgcttga agctggcagt gcctctcgat ccgaatgctc agagacagaa    60
gagcgcaatg gggactctta ctgaggatat tgcttgaagc tg                     102

<210> SEQ ID NO 26
<211> LENGTH: 34
<212> TYPE: DNA
<213> ORGANISM: Artificial Sequence
<220> FEATURE:
<223> OTHER INFORMATION: Oligonucleotide Probe 26

<400> SEQUENCE: 26
atatatatat cgcagtctct gaatatatat atat                               34

<210> SEQ ID NO 27
<211> LENGTH: 38
<212> TYPE: DNA
<213> ORGANISM: Artificial Sequence
<220> FEATURE:
<223> OTHER INFORMATION: Oligonucleotide Probe 27

<400> SEQUENCE: 27
aaaaaaaaaa gagaggcact gccagcttaa aaaaaaaa                           38

<210> SEQ ID NO 28
<211> LENGTH: 39
<212> TYPE: DNA
<213> ORGANISM: Artificial Sequence
<220> FEATURE:
<223> OTHER INFORMATION: Oligonucleotide Probe 28

<400> SEQUENCE: 28
atatatatac gccagccatt gcaacaggaa tatatatat                          39

<210> SEQ ID NO 29
<211> LENGTH: 45
<212> TYPE: DNA
<213> ORGANISM: Artificial Sequence
<220> FEATURE:
<223> OTHER INFORMATION: Oligonucleotide Probe 29

<400> SEQUENCE: 29
ttttatatat atatgtaaaa gagtctgtcc atcactatat atata                   45

<210> SEQ ID NO 30
<211> LENGTH: 49
<212> TYPE: DNA
<213> ORGANISM: Artificial Sequence
<220> FEATURE:
<223> OTHER INFORMATION: Oligonucleotide Probe 30

<400> SEQUENCE: 30
ttttttttat atatatatgt aaaagagtct gtccatcact atatata                 49

<210> SEQ ID NO 31
<211> LENGTH: 10
<212> TYPE: DNA

```
<213> ORGANISM: Artificial Sequence
<220> FEATURE:
<223> OTHER INFORMATION: Nt.AlwI Restriction Site
<220> FEATURE:
<221> NAME/KEY: misc_feature
<222> LOCATION: (6)..(10)
<223> OTHER INFORMATION: n is a, c, g, or t

<400> SEQUENCE: 31 ggatcnnnnn                                                                10
```

NUCLEIC ACID DETECTION METHOD

CROSS REFERENCE TO RELATED APPLICATIONS

The present application is a national phase entry of PCT/GB2016/052265 filed Jul. 22, 2016 which claims priority to UK application No. 1513128.7 filed on Jul. 24, 2015, the disclosures of which are incorporated by reference herein in their entireties. Applicants claim the benefit of these applications under 35 U.S.C. § 119 (a-d).

BACKGROUND

Technical Field

The present invention is directed to methods for the detection of nucleic acids of defined sequence, and compositions and kits for use in said methods.

Related Art

Methods of nucleic acid sequence amplification based on polymerases are widely used in a number of fields such as molecular biology research and the molecular diagnosis of disease. The most established method, polymerase chain reaction (PCR), typically involves two primers and uses temperature to achieve primer annealing, extension by DNA polymerase and denaturation of newly synthesised DNA in a cyclical exponential amplification process. The requirement for temperature cycling necessitates complex equipment which limits the use of PCR-based methods in certain applications.

As such a number of isothermal nucleic acid detection methods have been developed that do not require temperature cycling (Reviewed by Craw and Balachandran (2012) *Lab Chip* 12, 2469), such as Loop-mediated isothermal amplification (LAMP), Rolling Circle Amplification (RCA), Isothermal and Chimeric primer-initiated Amplification of Nucleic acids (ICAN), Strand Displacement Amplification (SDA), Helicase Dependent Amplification (HDA), Recombinase Polymerase Amplification (RPA), Nicking and Extension Amplification Reaction (NEAR), Nucleic Acid Sequence-Based Amplification (NASBA), EXPonential Amplification Reaction (EXPAR), SMart Amplification Process (SMAP2), Single Primer Isothermal Amplification (SPIA) and Beacon Assisted Detection AMPlification (BAD AMP). However, these methods all rely upon DNA polymerase(s) to achieve exponential amplification, which is essential for their utility in nucleic acid detection. Instead of using temperature to achieve the annealing and denaturation of double-stranded DNA during polymerase amplification, they use additional enzymes and probes, which increases complexity.

There is an important requirement for new methods for rapid, sensitive and specific nucleic acid sequence detection to overcome the requirement for temperature cycling of PCR and the complexity of existing isothermal methods. The present invention relates to a method of nucleic acid sequence detection which achieves exponential signal amplification using nicking agent(s) and oligonucleotide probe(s), without requirement for a DNA polymerase or temperature cycling.

Whilst one previous method has been described which uses nicking of a probe hybridised to the target nucleic acid as the basis for specific detection (U.S. Pat. No. 5,011,769), crucially, it does not encompass any intrinsic means of performing exponential amplification and thus its potential application is severely limited. Danielsen et al (WO2006/088910) subsequently employed this same method and found it necessary to combine it with a separate polymerase-based method, multiple displacement amplification (MDA), in order to achieve exponential amplification for the sensitive detection of target nucleic acids. Another method that employs nicking of a probe hybridised to the target nucleic acid (WO97/12062 and WO2003/054214) is focussed exclusively on amplifying a particular target, generating many copies of the original target sequence, analogous to most polymerase-based methods, such as PCR.

SUMMARY

The invention provides a method for detecting the presence of a target nucleic acid of defined sequence in a sample which method comprises the steps:
  a) contacting said sample with:
  i. a first oligonucleotide probe; and
  ii. a nicking agent;
  wherein the first oligonucleotide probe comprises a first complementarity region capable of sequence specific hybridisation to the target nucleic acid and a cleavage site for the nicking agent; and wherein the nicking agent specifically recognises double-stranded nucleic acid formed when the first oligonucleotide probe hybridises to the target nucleic acid in said sample and cleaves said first oligonucleotide probe to produce a first probe fragment;
  b) contacting said first probe fragment with:
  iii. a second oligonucleotide probe; and
  iv. a nicking agent;
  wherein the second oligonucleotide probe comprises a second complementarity region capable of sequence specific hybridisation to the first probe fragment and a cleavage site for the nicking agent; and wherein the nicking agent specifically recognises double-stranded nucleic acid formed when the second oligonucleotide probe hybridises to the first probe fragment and cleaves said second oligonucleotide probe to produce a second probe fragment;
  c) optionally contacting said second probe fragment with:
  v. a third oligonucleotide probe; and
  vi. a nicking agent;
  wherein the third oligonucleotide probe comprises a third complementarity region capable of sequence specific hybridisation to the second probe fragment and a cleavage site for the nicking agent; and wherein the nicking agent specifically recognises double-stranded nucleic acid formed when the third oligonucleotide probe hybridises to the second probe fragment and cleaves said third oligonucleotide probe to produce a third probe fragment;
  d) optionally repeating step c) n times, wherein n is a positive integer, using fourth and subsequent sequential (3+n)th oligonucleotide probe(s) to produce fourth and subsequent sequential (3+n)th probe fragment(s); and
  e) detecting the presence of the probe fragment produced at the end of step (b) and/or step (c) and/or step (d), wherein one or more of said detected probe fragment(s) is not capable of sequence specific hybridisation to the complementarity region of any of the oligonucleotide probes to form a site that is specifically recognised and cleaved by any of the said nicking agents and/or none of the probe fragments produced is capable of sequence specific hybridisation to the first complementarity region of the first oligonucleotide probe, and wherein the presence of said detected probe fragment(s) indicates the presence of the target nucleic acid in said sample.

An embodiment of the method is illustrated in FIG. 1.

In various embodiments, the method produces an exponentially increasing number of probe fragments in the presence of target nucleic acid without requirement for a DNA polymerase.

In another aspect, the invention provides a method as defined above wherein the probe fragments produced in steps (a), (b) and optional steps (c) and (d) are not capable of sequence specific hybridisation to the complementarity region of any one of the preceding oligonucleotide probes.

The present invention in various aspects is advantageous over the prior art because it encompasses intrinsic exponential amplification and thus it has greatly improved potential for application in the sensitive detection of target nucleic acids of defined sequence. The amplification effect of the method can also be controlled by selecting the number of oligonucleotide probes in the sequential series (see FIG. 2), this is important, for example, because it allows the appropriate amplification to be selected for a given target and enables quantification of the target.

The method is not focussed on amplifying a particular target, i.e. generating many copies of the original target sequence, which is the exclusive focus of most polymerase-based methods, such as PCR and another method that employs nicking of a probe hybridised to the target nucleic acid (WO2003/054214). The method of the invention employs a sequential series of probes and does not employ a closed loop system wherein, for example, the probe fragment produced following cleavage of the second oligonucleotide probe is a 'functional target equivalent'.

Because the focus is not to produce functional target equivalents, the method comprises either or both of the following features: (i) none of the probe fragments produced is capable of sequence specific hybridisation to the first complementarity region of the first oligonucleotide probe; and/or (ii) "end-point" detection, wherein one or more of the detected probe fragment(s) is not capable of sequence specific hybridisation to the complementarity region of any of the oligonucleotide probes to form a site that is specifically recognised and cleaved by any of the nicking agents.

The invention provides increased flexibility in probe design and nicking agent selection as there is no requirement for the probe fragment(s) to be a functional equivalent of the target sequence. This allows optimisation of sequences and nicking agents for efficient detection. Avoiding a closed-loop system, and removing the requirement for generation of functional equivalents of the target also provides the opportunity to develop a universal multi-probe amplification system whereby the same set of probes in step (b) and optional steps (c) and (d) and the detection system can be used from application to application without needing to be altered. This "universal" detection system can be coupled to an alternative probe in step (a), without the reaction components and detection system having to be altered each time.

The invention also provides a greater degree of versatility in multiplexing with multiple sequential series of probes readily combined for the detection of multiple targets than known detection methods. Multiple targets (e.g. different strains of a pathogen) can either be differentially detected or detected together through the same signal. For example, probe fragments generated from cleavage of multiple different variants of the first oligonucleotide probe, if desired, could be linked to the same second oligonucleotide probe. In a system which uses "functional target equivalents" there is an increased risk of cross-talk which reduces the multiplexing potential. Furthermore, multiplexing requires significant optimisation of probe sequences to ensure they function well together. As described above, in a universal amplification and detection system a number of sequential series of probes can be developed and optimised to be compatible together in advance and then repurposed for any given target solely by replacing the first oligonucleotide probe.

The invention utilises "end-point detection" which provides further advantages over "closed-loop" systems in which every probe fragment released has potential to hybridise to another (immobilised) probe present in the reaction. This causes a significant problem because such probes can act as a "sink" and require separation before they can be efficiently and quantitatively detected. In other words, there is no "end-point" probe fragment which accumulates without the ability to hybridise. Such an "end-point" probe is attractive to form the basis of the probe fragment which is detected. Detection of that probe fragment can be done efficiently by hybridisation to a complementary probe because it is single-stranded DNA. Detection by hybridisation is particularly amenable to multiplex detection, e.g. by nucleic acid lateral flow, because the complementary sequence of the probe fragment(s) from different series of the probes can be printed on a lateral flow strip. Various embodiments of the above mentioned aspects of the invention, and further aspects, are described in more detail below.

DETAILED DESCRIPTION

We have developed a method for detecting the presence of a target nucleic acid of defined sequence in a sample. The target nucleic acid may be single-stranded DNA, including single-stranded DNA derived from double-stranded DNA following disassociation of the two strands such as by heat denaturation or through strand displacement activity of a polymerase, or derived from RNA by the action of reverse transcriptase, or derived from double-stranded DNA by use of a nuclease, such as a restriction endonuclease or exonuclease III, or derived from a RNA/DNA hybrid through an enzyme such as Ribonuclease H. The target nucleic acid may be single-stranded RNA, including single-stranded RNA derived from double-stranded RNA following disassociation of the two strands such as by heat denaturation or derived from DNA by transcription. The target nucleic acid may be DNA derived from DNA by a DNA polymerase.

The method uses a nicking agent and a first oligonucleotide probe containing a first complementarity region capable of sequence specific hybridisation to the target nucleic acid and a cleavage site for a nicking agent; wherein the nicking agent specifically recognises the double-stranded nucleic acid formed when the oligonucleotide probe hybridises to the target nucleic acid to form a double stranded nucleic acid. Said double-stranded nucleic acid may be a double-stranded DNA, a double stranded RNA or a hybrid duplex comprising strands of both RNA and DNA. Typically, the oligonucleotide probes, and all probes used in the method, are DNA probes which form with the DNA or RNA target a double stranded DNA or a hybrid duplex comprising strands of both RNA and DNA. However, RNA probes or probes comprising other nucleic acids, such as non-natural bases and/or alternative backbone structures, may also be used.

Following specific recognition of the double stranded nucleic acid by the nicking agent, the nicking agent cleaves the first oligonucleotide probe to produce a first probe fragment leaving the target nucleic acid at least functionally intact, in that it is capable of target recycling. The first probe fragment is then contacted with a nicking agent and the second oligonucleotide probe containing a second complementarity region capable of sequence specific hybridisation to the first probe fragment and a cleavage site for a nicking agent; wherein the nicking agent specifically recognises the double-stranded nucleic acid formed when the oligonucleotide probe hybridises to the first probe fragment to form a double stranded nucleic acid and cleaves said second oligonucleotide probe to produce a second probe fragment.

Figure 1:
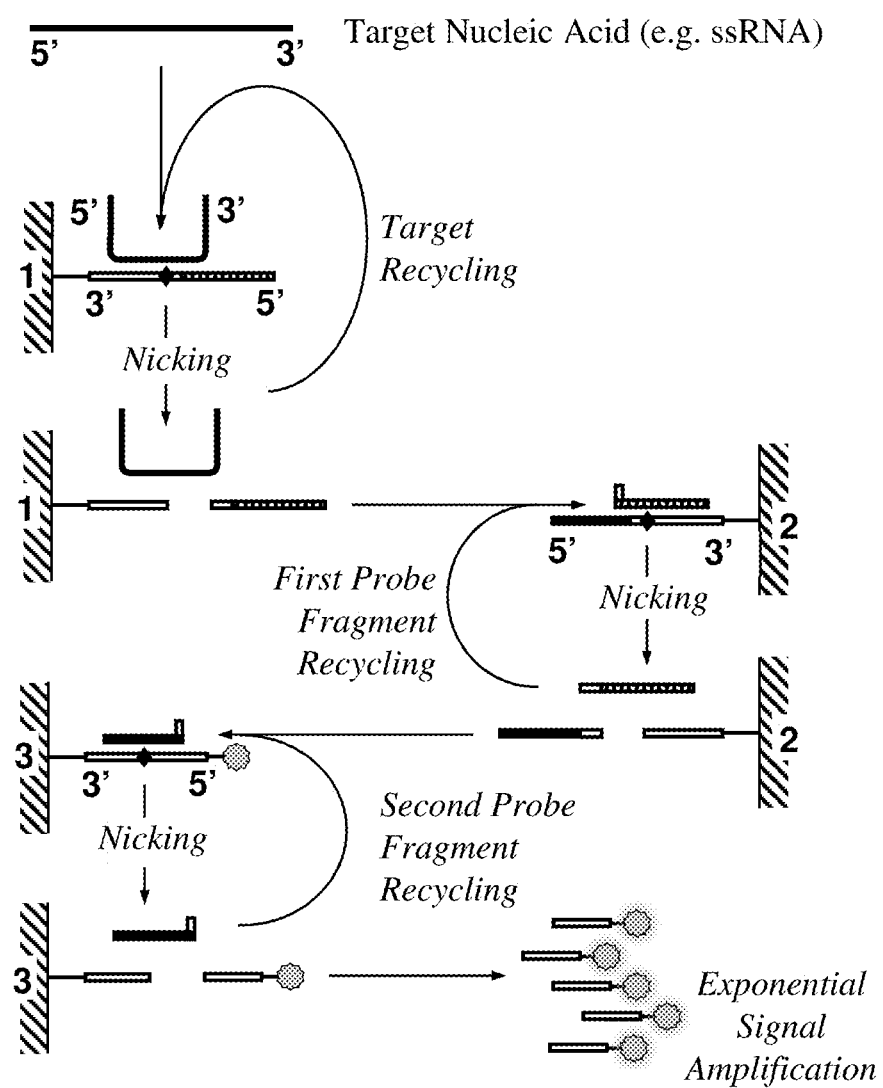
FIG. 1. Schematic representation of the method according to one aspect of the invention.

Optionally the second probe fragment is then contacted with a nicking agent and third oligonucleotide probe containing a third complementarity region capable of sequence specific hybridisation to the second probe fragment and a cleavage site for a nicking agent; wherein the nicking agent specifically recognises the double-stranded nucleic acid formed when the oligonucleotide probe hybridises to the second probe fragment to form a double stranded nucleic acid and cleaves said third oligonucleotide probe to produce a third probe fragment. Optionally any number of oligonucleotide probes could be used in sequential sequence as described, where the preceding step is repeated n times, wherein n is a positive integer, using a fourth and subsequent sequential (3+n)th oligonucleotide probe(s) to produce fourth and subsequent sequential (3+n)th probe fragment(s). One or more of the probe fragments produced following cleavage by the nicking agents is detected and the presence of said probe fragment(s) indicates the presence of the target nucleic acid in the sample. A schematic representation of one embodiment of the invention is depicted in FIG. 1.

The number n can, for example, be 1 (i.e. the total number of oligonucleotide probes is 4) or 2 or 3 or 4 or 5 or 6 or 7 or 8 or 9 or 10 or a greater number as described in further detail below.

In an embodiment steps (c) and (d) are omitted. In an embodiment step (c) is present and step (d) is omitted.

Suitably no DNA polymerase is used in the method of the invention. The method of the invention does not require any PCR or other polymerase-dependent amplification steps.

Thus, typically, an oligonucleotide probe, suitable for use in the above method, comprises:
a. a first complementarity region capable of sequence specific hybridisation to a target sequence to form double-stranded nucleic acid that is specifically recognised by a nicking agent and that contains the cleavage site for said nicking agent; and
b. a further complementarity region which is separated from the first complementarity region following cleavage at said cleavage site, and which is capable of sequence specific hybridisation to another oligonucleotide probe to form a double-stranded nucleic acid that is specifically recognised by a nicking agent, and that contains the anti-sense sequence of the cleavage site for said nicking agent.

The above probe is suitable for all steps of the method, however, the final probe in the sequential series of probes in the method needs not have b. the further complementarity region.

Such probe may be provided in the form of a kit, optionally together with instructions for performance of the method of the invention.

Thus a further aspect of the invention is a kit comprising the following:
a. a first oligonucleotide probe [X] comprising:
  i. a complementarity region [A] capable of sequence specific hybridisation to a target sequence to form double-stranded nucleic acid that is specifically recognised by a nicking agent and that contains the cleavage site for said nicking agent; and
  ii. a further complementarity region [B] which is separated from region [A] following cleavage at said cleavage site, and which is capable of sequence specific hybridisation to a second oligonucleotide probe [Y] to form a double-stranded nucleic acid that is specifically recognised by a nicking agent, and that contains the anti-sense sequence of the cleavage site for said nicking agent;
and
b. a second oligonucleotide probe [Y] comprising:
  i. a complementarity region [C] capable of sequence specific hybridisation to the complementarity region [B] in said first oligonucleotide probe [X] to form a double-stranded nucleic acid that is specifically recognised by a nicking agent and that contains the cleavage site for said nicking agent; and
  ii. a second region [D] which is separated from region [C] following cleavage at said cleavage site, and which is not capable of sequence specific hybridisation to the complementarity region [A] or [C] of the first or second oligonucleotide probes to form a site that is specifically recognised and cleaved by any of the said nicking agents.

It will be understood that X and Y can be the first and second oligonucleotide probes in the sequential series of oligonucleotide probes used in the method by reference to FIG. 1 or the second and third or indeed, if a greater number of oligonucleotide probes is used in an embodiment of the method, any pair of sequential probes used in the method. In an embodiment, the second region [D] of said second oligonucleotide probe may, following cleavage of the second oligonucleotide probe to separate [D] from [C], be detected as a probe fragment in step (e) of the method. In a further embodiment of the invention in the kit as defined above the second region [D] of said second oligonucleotide probe is a complementarity region which is capable of sequence specific hybridisation to a third oligonucleotide probe to form a double-stranded nucleic acid that is specifically recognised by a nicking agent, and that contains the anti-sense sequence of the cleavage site for said nicking agent; which kit further comprises:
c. a third oligonucleotide probe comprising:
  i. a complementarity region [E] capable of sequence specific hybridisation to the complementarity region [D] in said second oligonucleotide probe to form a double-stranded nucleic acid that is specifically recognised by a nicking agent and that contains the cleavage site for said nicking agent; and
  ii. a second region [F] which is separated from region [E] following cleavage at said cleavage site, and which is not capable of sequence specific hybridisation to the complementarity regions [A] and [C] of said first and second oligonucleotide probes;
and
d. optionally further (3+n)th oligonucleotide probes wherein the second region of said (2+n)th oligonucleotide probe is a complementarity region which is capable of sequence specific hybridisation to a (3+n)th oligonucleotide probe to form a double-stranded nucleic acid that is specifically recognised by a nicking agent, and that contains the anti-sense sequence of the cleavage site for said nicking agent, and the (3+n)th oligonucleotide probe comprises:
  i. a complementarity region capable of sequence specific hybridisation to the complementarity region in said (2+n)th oligonucleotide probe to form a double-stranded nucleic acid that is specifically recognised by a nicking agent and that contains the cleavage site for said nicking agent; and
  ii. a second region which is separated from the first complementarity region described in (i) following cleavage at said cleavage site, and which is not capable of sequence specific hybridisation to the complementarity regions of any of said preceding oligonucleotide probes to form a site that is specifically recognised and cleaved by any of the said nicking agents.

Such kits for performance of the method may also contain one or more nicking agent(s). A "nicking agent" refers to any means, chemical, biological or physical which cleaves the phosphodiester bond on a single strand of two duplexed or double-stranded nucleic acid molecules at an intended target site. A number of embodiments of the present invention employ a class of enzyme known as nicking endonucleases or nicking restriction endonucleases, which may be a naturally occurring enzyme or an engineered enzyme. Such enzymes specifically recognise a particular recognition sequence within a double-stranded nucleic acid and cleave only one strand of the nucleic acid duplex at a particular cleavage site leaving the other strand intact.

A "double-strand cleaving agent" refers to any means, chemical, biological or physical which cleaves the phosphodiester bond on both strands of two duplexed or double-stranded nucleic acid molecules at an intended target site. Double-strand cleaving agents include double strand cleaving restriction enzymes or restriction endonucleases, a broad class of enzyme capable of recognising a particular recognition sequence within a double-stranded nucleic acid and cleaving both strands of the nucleic acid duplex at particular cleavage sites. A large number of restriction enzymes are available covering a wide range of recognition sequences. Such restriction enzymes, despite being capable of cleaving both strands of a double-stranded nucleic acid, can in certain circumstances also function as nicking agents and be employed as nicking agents for the performance of the invention in a number of ways, including the following:

(a) Certain double-strand cleaving enzymes have a preference (increased rate) for the cleavage of one strand of a double-stranded nucleic acid over the other strand and therefore are capable of binding to a double-stranded nucleic acid and cleaving only one of the strands and thus acting as a nicking agent, at least for a certain proportion of binding/cleavage events. For example, the double-strand cleaving restriction endonuclease FokI has such a "strand preference" for cleavage of the bottom strand of its recognition site, whilst the double-strand cleaving restriction endonuclease BbsI has a strong preference for cleavage of the top strand of its recognition site (Example 3, FIG. 15A and FIG. 15B).

(b) One of the strands within the double-stranded nucleic acid at the recognition and cleavage site is not capable of being cleaved by said restriction enzyme. This can be accomplished in a number of ways, including the following.

i) One of the two nucleic acid strands in the duplexed nucleic acid target consists of a sequence that terminates prior to, and therefore does not contain, the phosphodiester bond that would be capable of being cleaved by the enzyme. Such nucleic acid strand whose sequence terminates one side of the known phosphodiester cleavage site for said enzyme may be referred to as a 'truncated template'. For example, Example 3 (FIG. 15C) demonstrates that the double-strand cleaving restriction endonuclease BccI can act as a nicking agent using a truncated template, as illustrated below:

BccI Restriction Site (recognition sequence in bold; cut sites shown by triangles):

BccI as a Nicking Agent (truncated template is not cleaved)

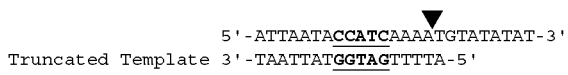

ii) Double-strand cleaving restriction enzymes are typically able to act as nicking agents if one strand of the double-stranded nucleic acid target site is modified such that the phosphodiester bond of the cleavage site on one of the strands is protected using a nuclease resistant modification, such as a phosphorothioate (PTO) internucleotide linkage. For example, Example 3 (FIG. 15) demonstrates the use of enzymes FokI, BbsI and BccI as nicking agents with PTO linkages.

As nicking agents cleave only one strand of the nucleic acid duplex, oligonucleotide probe cleavage mediated by nicking agents are non-destructive in respect of the target nucleic acid, allowing target recycling to occur.

"Target recycling" refers to a cyclical process whereby a target nucleic acid following sequence specific hybridisation to an oligonucleotide probe and cleavage of said probe by a nicking agent, is left intact and able to undergo sequence specific hybridisation to further oligonucleotide probes for the process to repeat. Following cleavage by a nicking agent, an oligonucleotide probe produces two shorter oligonucleotide fragments, which dissociate from the target nucleic acid in a process which is likely to be favoured by a significant decrease in melting temperature of the duplexes formed by said shorter oligonucleotide fragments compared to the original oligonucleotide probe. As it is unaffected by the cleavage and hybridisation process, the target nucleic acid is then subsequently available for sequence specific hybridisation to further oligonucleotide probes for repetition of the process. In the present invention a probe fragment produced from cleavage of an oligonucleotide probe also acts as a target nucleic acid for the subsequent oligonucleotide probe if one is present. As such the concept of target recycling should also be considered to encompass the recycling of probe fragments (see FIG. 1).

The nicking agent is typically employed in the relevant steps in an amount of 0.1-100 Units, where one unit is defined as the amount of agent required to digest 1 μg T7 DNA in 1 hour at a given temperature (e.g. 37° C.) in a total reaction volume of 50 μl. However, the amount depends on a number of factors such as the activity of the nicking agent selected, the concentration and form of the nicking agent, the anticipated concentration of the target nucleic acid, the volume of the reaction, the number and concentration of the oligonucleotide probes and the reaction temperature, and should not be considered limiting in any way.

According to an embodiment of the method, two or more of steps (a), (b) and (e) and optional steps (c) and (d) are performed simultaneously.

Steps (a), (b) and optional steps (c) and (d) may be performed over a wide range of temperatures. Whilst the optimal temperature for each step is determined by the temperature optimum of the relevant nicking agent and the melting temperature of the complementarity region of the oligonucleotide probe and the fragments produced following cleavage of said probe, the exponential amplification of the method allows the steps to be performed over a wide temperature range, e.g. 20-60° C.

According to an embodiment of the method, two or more of the nicking agents in different steps (a), (b) and optional steps (c) and (d) are the same. For example, the same nicking agent may be used in all of different steps (a), (b) and optional steps (c) and (d).

Our investigations have revealed that oligonucleotide probe cleavage by nicking agents occurs over a wide range of target nucleic acid levels from very low copy numbers up to equimolar amounts or even with excess target nucleic acid. Target recycling permits an amplification effect if oligonucleotide is provided in excess of target nucleic acid because many probe fragments can be produced by each target nucleic acid in a cleavage reaction. Various experiments have also revealed that the thermodynamic equilibrium of oligonucleotide probe cleavage lies substantially in favour of cleavage and in most cases will therefore proceed to completion if the rate is sufficient. Typically, the first oligonucleotide probe is present in molar ratio to target nucleic acid of $10^9$ to 1 to $10^3$ to 1, although such ranges should be regarded as non-limiting.

"Sequence specific hybridisation" refers to the ability of an oligonucleotide probe to bind to a target nucleic acid or a probe fragment by virtue of the hydrogen bond base pairing between complementary bases in the sequence of each nucleic acid. Typical base pairings are Adenine-Thymine (A-T), or Adenine-Uracil in the case of RNA or RNA/DNA hybrid duplexes, and Cytosine-Guanine (C-G), although a range of natural and non-natural analogues of nucleic acid bases are also known with particular binding preferences. In the present invention, the complementarity region of oligonucleotide probe does not necessarily need to comprise natural nucleic acid bases in a sequence with complete and exact complementarity to the target nucleic acid or relevant probe fragment; rather for the performance of the method the oligonucleotide probe only needs to be capable of sequence specific hybridisation to the target nucleic acid or probe fragment sequence sufficiently to form the double-stranded recognition sequence and the cleavage site of the relevant nicking agent to allow cleavage of the oligonucleotide probe. Such hybridisation may be possible without exact complementarity, and with non-natural bases or abasic sites. Sequence specific hybridisation is an important factor in the design of oligonucleotide probes to perform specific detection of target nucleic acids, which in certain applications may be present at low copy number and in the presence of a large excess of other nucleic acids. The design of oligonucleotide probes is described in more detail below.

Nevertheless, in an embodiment, the complementarity between the complementarity region of the first oligonucleotide probe and the target nucleic acid is 100%. In other embodiments there are one or more non-complementing base pairs. In some circumstances it may be advantageous to use a mixture of oligonucleotide probes in a given step of the method (or all of them). Thus, by way of example, in the case of a target nucleic acid comprising a single nucleotide polymorphism (SNP) site having two polymorphic positions, a 1:1 mixture of oligonucleotide probes differing in one position (each component having complementarity to the respective base of the SNP) may be employed. During manufacture of oligonucleotides it is routine practice to randomise one or more bases during the synthesis process. Similarly, in an embodiment, the complementarity between the complementarity region of a probe fragment and the complementarity region of another probe with which it is intended to hybridise in the sequence of steps of the method is 100%. In other embodiments there are 1 or 2 non-complementing base pairs.

The present invention yields exponential production of oligonucleotide probe fragment over time. Exponential signal amplification is an essential property of sensitive nucleic acid detection methods, such as PCR and isothermal methods that have been employed widely in various fields. In polymerase based methods, following separation of the DNA duplex both strands are available to be copied by DNA polymerase thus doubling the starting amount. This theoretical doubling of the signal after each cycle means the method can be employed in highly sensitive detection of very small quantities of nucleic acid material. In a nicking agent based cleavage reaction comprising a target nucleic acid and a single oligonucleotide probe (in excess) the reaction proceeds in a directly proportional (first order) fashion in the steady state wherein the amount of probe fragment formed accumulates in a directly proportional amount over time, until one or more reagent becomes limiting. Through use of a second oligonucleotide probe in this method, exponential production of the second probe fragment results. The basis of this is that as the amount of first probe fragment accumulates over time, the amount of target available for the cleavage of the second oligonucleotide probe is continually increasing. Due to target recycling of the first probe fragment, the result is an exponential (second order) reaction for production of the second probe fragment. In embodiments of the method employing a third oligonucleotide probe a further exponential effect is observed by virtue of the fact that the number of copies of the target for the third oligonucleotide probe, being the second probe fragment, is itself increasing exponentially, with each copy capable of acting as a site of target recycling for the third oligonucleotide probe. In embodiments of the invention with a greater number of oligonucleotide probes, a further enhanced exponential effect is observed.

For applications in which the invention will be used in order to detect a very low copy number of the target nucleic acid it is intended that oligonucleotide probes are provided in large excess of the target nucleic acid thereby providing the opportunity for signal amplification as the method proceeds. The oligonucleotide probe(s) that produces the probe fragment(s) to be detected in step (e) must at least be at a level wherein the probe fragment produced following cleavage of said oligonucleotide probe(s) is sufficiently above the limit of detection of the detection method employed to allow said probe fragment(s) to be readily detected. Typically using polyacrylamide gels with SYBR gold staining we have observed a limit of detection of 0.01 pmol of probe fragment (approximately 6 billion copies). A similar limit is observed using detection with a colorimetric moiety, such as gold nanoparticles, although the appropriate level would depend on the detection method to be employed. It would be advantageous to design the method such that none of the oligonucleotide probes in the sequential series would become exhausted (i.e. all copies cleaved) prior to the probe fragment(s) detected in step (e) reaching a detectable amount. Intuitively therefore one may expect to design the method such that each oligonucleotide probe in the sequential series is at a higher level that the preceding probe, due to the exponential cascade effect that occurs. However, this needs to be balanced with the possibility that increased concentration of oligonucleotide probe may increase the rate of its cleavage at a given level of target nucleic acid.

Figure 2:
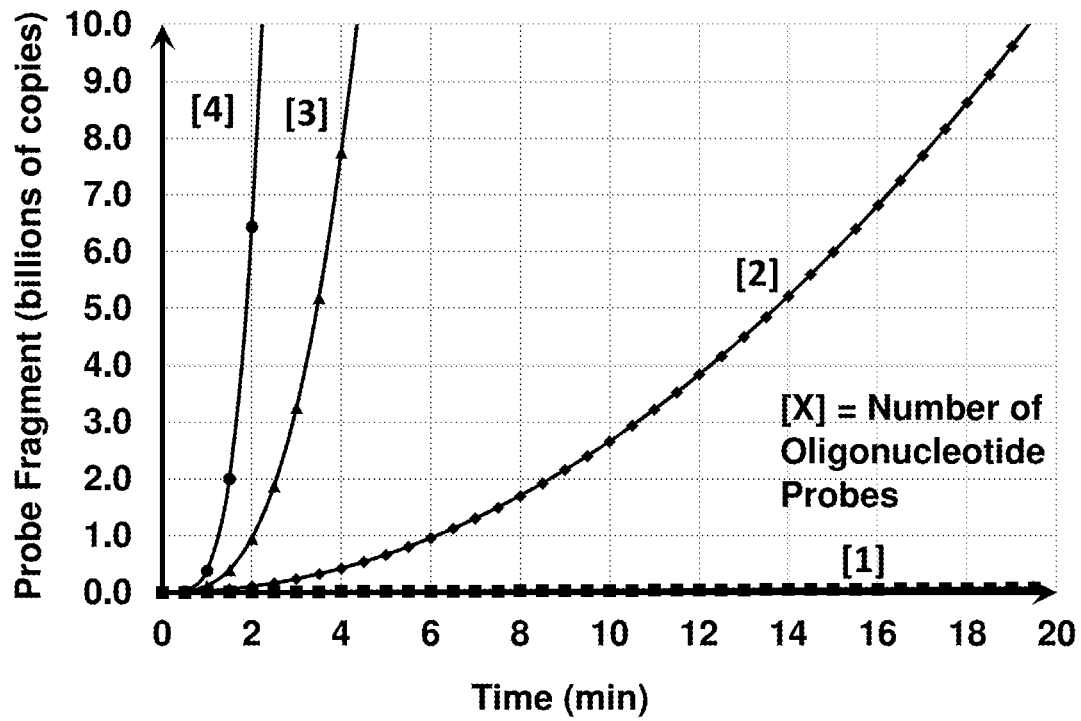
FIG. 2. Model demonstration of exponential signal produced with an increasing number of oligonucleotide probes.

We have constructed a quantitative model, displayed in FIG. 2, to demonstrate the exponential signal amplification enhancement effect observed when an increasing number of oligonucleotide probes in sequential series are used in the method. As the basis of this model, we used a typical rate of 13.8 oligonucleotide probe cleavage events per target molecule per minute, determined from a number of experiments using the nicking endonuclease Nt.BstNBI (NEB) with 5 pmol of oligonucleotide probe at various levels of a control target nucleic acid, analysed by polyacrylamide gels detected with SYBR gold (Life Technologies). The model demonstrates the detection of a typical target nucleic acid which is present at a copy number of approximately 280,000 copies. When detection is performed with only a single oligonucleotide probe, such as the method used by Duck et al (U.S. Pat. No. 5,011,769) and Danielson et al (WO2006/088910) in the prior art, cleavage of the oligonucleotide probe and accumulation of probe fragment would occur proportionally over time, with 280,000 copies of probe fragment accumulating every 4.35 seconds. In such a method, without the exponential signal amplification of the present invention, it would take a very long time (theoretically over 25 hours) for the number of copies of probe fragment to exceed 6 billion copies (a nominal limit of detection assumed) and it is likely that the nicking agent employed would lose activity during such a long incubation. In contrast, when the present invention is employed, with a sequential series of oligonucleotide probes, (two, three and four probe reactions are displayed on FIG. 2), an exponential amplification effect is observed allowing more rapid detection. For example, with two oligonucleotide probes 280,000 copies of the first probe fragment accumulate every 4.35 seconds. Therefore after 4.35 seconds there are 280,000 copies of the first probe fragment available to act as the target nucleic acid for the second oligonucleotide probe, and the second oligonucleotide probe is cleaved at the same rate as the first oligonucleotide probe. However, as the first probe fragment accumulates, the rate of cleavage of the second oligonucleotide probe increases leading to exponential accumulation of the second probe fragment. After 8.7 seconds there are 560,000 copies of the first probe fragment and the rate of cleavage of the second oligonucleotide probe occurs as twice the rate of the cleavage of the first oligonucleotide probe. The model predicts that the nominal detection limit of 6 billion copies of probe fragment would be reached within 15 minutes with use of two oligonucleotide probes and within 4 minutes or 2 minutes with use of three or four oligonucleotide probes, respectively. In this model we have not assumed any reduction in rate over time due to one or more reagent becoming limiting. We have assumed that only a single probe fragment, from the last oligonucleotide probe in the sequential series, is detected; although, it is noteworthy that a further signal amplification effect would result if more than one of the probe fragments is detected.

The present invention has the unusual property of allowing the sensitivity of detection of a target nucleic acid sequence to be increased or decreased as desired for particular applications by using a greater or lesser number of oligonucleotide probes in the sequential series. Such a feature is not possible with a "closed-loop" amplification system. We have used a theoretical model to consider the practical range of the number of oligonucleotide probes to be used in the method and to identify the range of numbers possible for 'n' in step (d) of the method. Whilst theoretically a very large number of sequential probes could be used, in practice the appropriate number would be defined by the rate of the cleavage reaction, the starting amount of target nucleic acid, the detection method employed and the practicality of manufacturing and using a greater number of reagents. In our theoretical model assuming a probe turnover rate of 13.8 per minute, six oligonucleotide probes (i.e. n=3) would be sufficient to detect a single copy of target nucleic acid within 10 minutes. It is possible, however, that the efficiency of turnover is lower for a particular nicking agent or target nucleic acid. In the event the turnover rate was reduced to 3 per minute, 12 oligonucleotide probes (i.e. n=9) would be sufficient to detect ten copies of target nucleic acid within 10 minutes. Whilst there is no theoretical limit on the number of 'n' in step (d), practical limitations mean that 'n' is likely to range between 0 and 15.

There are a number of considerations for the design of the oligonucleotide probes for performance of the method. The first oligonucleotide probe must comprise a first complementarity region capable of sequence specific hybridisation to the target nucleic acid to form the recognition sequence and cleavage site for a nicking agent and a further complementarity region capable of acting as the target nucleic acid for the second oligonucleotide probe and that contains the anti-sense of the recognition sequence and cleavage site for a nicking agent. During probe design it is necessary to define the sequence and length of each complementarity region in order to permit optimal sequence specific hybridisation and disassociation of the fragments produced following oligonucleotide probe cleavage. The target nucleic acid contains the antisense of a recognition sequence and cleavage site for a nicking agent that defines the minimal potential sequence of the first complementarity region of the first oligonucleotide probe. Typically this region would comprise at least 7 bases for a nicking endonuclease (Table 1). In the event that a double-strand cleaving restriction endonuclease is employed as nicking agent for the cleavage of the first oligonucleotide probe, the sequence of the first complementarity region of the first oligonucleotide probe would be designed to ensure that it is capable of sequence-specific hybridisation to a truncated template and/or that it contains the sequence that has the highest rate of cleavage in the event the chosen nicking agent exhibits a strand preference. The theoretical melting temperature of the total sequence and the two fragments that would be produced following cleavage are also considered in the context of the likely temperature of the reaction and the nicking agent selected, which is balanced with the improvement to specificity of binding and detection that results as sequence length is increased. Our various investigations have indicated considerable versatility in the design of the complementarity regions able to be used effectively in the method. We have performed reactions with complementarity regions of up to 102 bases in length, evidencing binding and cleavage of the oligonucleotide probe and target recycling with disassociation of the fragments produced during cleavage. Depending on the properties of the particular nicking agent (e.g. temperature activity range and sequence specificity) and target nucleic acid sequence (e.g. % of GC), we would typically expect an optimal complementarity region to be between 7 and 150 bases in length. The target nucleic acid is then defined as the functional sequence capable of sequence specific hybridisation to that first complementarity region to form the recognition sequence for the relevant nicking agent and to permit cleavage of the probe. Such a target may be smaller than the total length of the complementarity region, or very significantly larger, for example when a particular region of a large genome is targeted.

There is considerable flexibility in the design of the further complementarity region of the first probe and the complementarity region(s) of the second and any subsequent probes. This is because the nicking agent may be selected without any limitation of the target nucleic acid sequence. The constraints on the size and design of the complementarity regions are otherwise similar. The overall size of the probes and the size and sequence of any spacers and non-complementary sequences may be optimised to ensure the reaction proceeds efficiently. Crucially the second and subsequent oligonucleotide probes and relevant nicking agents that cleave said probes, once they have been optimised, can form a "universal amplification and detection system" which can be applied to the detection of any target by replacing only the first complementarity region of the first oligonucleotide probe. This is particularly advantageous for the application of the present invention as a sequential series of oligonucleotide probes and associated detection reagents only need to be optimised once and can then be manufactured in bulk for multiple applications. Oligonucleotide probes for use in the method would typically comprise nucleic acid (e.g. DNA) of standard base composition. However, use of non-natural bases or abasic sites may provide greater flexibility in probe design in certain embodiments. A number of alternative variants of the nucleic acid (e.g. DNA) backbone are also available for use in synthetic oligonucleotide probes, such as phosphorothioate oligos or peptide nucleic acids. Such modified backbones can be resistant to nuclease cleavage and therefore would allow double-strand cleaving agents to be employed as nicking agents in the method. The second and subsequent oligonucleotide probes may also comprise a truncated target sequence that permits the use of double strand cleaving agents (e.g. restriction endonucleases) as nicking agents. Alternatively, introduction of scissile linkage within the backbone at a particular cleavage site, may permit use of other enzymes, e.g. RNaseH, in the performance of the method.

During probe design in certain embodiments at least one oligonucleotide probe fragment in the sequential series of steps (a), (b), and optional steps (c) and (d) may be designed to be capable of sequence specific hybridisation to the complementarity region of one of the preceding oligonucleotide probes. Typically such an oligonucleotide probe fragment may both act as a target nucleic acid for a subsequent oligonucleotide probe to allow the sequential process to continue, and also cause additional amplification by increasing the rate of cleavage of one of the preceding oligonucleotide probes. Notwithstanding the foregoing, one or more of the detected probe fragment(s) is not capable of sequence specific hybridisation to the complementarity region of any of the oligonucleotide probes to form a site that is specifically recognised and cleaved by any of the nicking agent(s) and/or none of the probe fragments produced is capable of sequence specific hybridisation to the first complementarity region of the first oligonucleotide probe. Detection of an 'end-point' probe fragment which is not capable of sequence specific hybridisation to the complementarity region of any of the oligonucleotide probes to form a site that is specifically recognised by any of the nicking agent(s), offers advantages over a 'closed-loop' system wherein all of the detected probe fragments are capable of sequence specific hybridisation to one or more of the oligonucleotide probes, since it avoids competitive binding for that probe fragment, which reduces the efficiency of the method and hampers detection of that probe fragment. Furthermore, there is no requirement to generate "functional equivalents" of the target nucleic acid in the method, such as occurs in PCR and other methods, since the intended application is not to amplify the target, but rather to detect its presence in a sample.

In a particular embodiment of the method one or more of the oligonucleotide probes may contain multiple copies of the complementarity region(s) that are capable of functioning in the method. This enables enhanced amplification effect if, for example, oligonucleotide probes are attached to a solid material, as many copies of the minimal functional unit of an oligonucleotide probe can be released into the aqueous phase following a single cleavage event. In an alternative embodiment, one or more of the oligonucleotide probe(s) may be pre-hybridised to a complementary oligonucleotide which when hybridised alongside the probe fragment from the preceding probe, for example, then form a site that is specifically recognised by the nicking agent(s) for performance of the method. The advantage of such a "two fragment" embodiment is that the pre-hybridised complementary oligonucleotide can be designed to block sequence specific hybridisation of the preceding oligonucleotide probe, prior to its cleavage by a nicking agent, thus enabling the method of the invention to be performed in the aqueous phase, without requirement for the oligonucleotide probes to be attached to a solid material or otherwise separated.

For optimal practice of the invention the oligonucleotide probe fragment and not the uncleaved oligonucleotide probe should participate in hybridisation to and cleavage of the subsequent probe in the performance of the method. Therefore, when performing the invention it is advantageous to either remove or significantly limit the potential for uncleaved oligonucleotide probe to contact subsequent probes within the reaction. One of ordinary skill in the art will recognise that there are a number of ways in which this can be achieved through various means of separation of probe fragments from the respective oligonucleotide probe. In various embodiments of the method, therefore, one or more of the oligonucleotide probes is attached to a solid material. In other embodiments one or more of the oligonucleotide probes is attached to a moiety that permits attachment of said oligonucleotide probe to a solid material. In other embodiments, the probe fragment produced from the oligonucleotide probe in one or more of steps (a), (b), and optional steps (c) and (d), is separated from said oligonucleotide probe on the basis of its physicochemical properties, such as its size, sequence or charge, prior to the performance of the subsequent step.

In embodiments of the method wherein one or more of the oligonucleotide probes is attached to a solid material during the cleavage reaction, the solid material to which an oligonucleotide probe is attached can be readily separated from the aqueous phase and, if relevant, from the solid material to which another oligonucleotide probe is attached. Attachment may be performed such that, following cleavage of the oligonucleotide probe attached to the solid material by the relevant nicking agent in the presence of the relevant target, the probe fragment produced is released from the solid material into the aqueous phase and thus becomes available for sequence specific binding to the subsequent oligonucleotide probe in the sequential series. Uncleaved oligonucleotide probe and the other fragment produced following cleavage remain attached to the solid material and therefore not able to contact the subsequent oligonucleotide probe for sequence specific hybridisation. Release of probe fragment(s) into the aqueous phase also facilitates their detection in step (e) to determine the presence of target nucleic acid in a sample, because differential detection from other oligonucleotides, which remain attached to the solid material, is not required. In an embodiment of the method where separate cleavage reactions are performed for one or more of steps (a), (b) and optional steps (c) and (d), release of probe fragment into the aqueous phase ensures only the probe fragment, and not the respective uncleaved oligonucleotide probe which contains the same complementarity region, is transferred to the subsequent reaction if only the aqueous phase is transferred between reactions.

It is possible to covalently attach one or more of the oligonucleotide probes to a variety of solid materials for the performance of the method. A number of different solid materials are available which have or can be attached or functionalised with a sufficient density of functional groups in order to be useful for the purpose of attaching or reacting with appropriately modified oligonucleotide probes. Further, a wide range of shapes, sizes and forms of such solid materials are available, including beads, resins, surface-coated plates, slides and capillaries. Examples of such solid materials used for covalent attachment of oligonucleotides include, without limitation: glass slides, glass beads, ferrite core polymer-coated magnetic microbeads, silica micro-particles or magnetic silica micro-particles, silica-based capillary microtubes, 3D-reactive polymer slides, micro-plate wells, polystyrene beads, poly(lactic) acid (PLA) particles, poly(methyl methacrylate) (PMMA) micro-particles, controlled pore glass resins, graphene oxide surfaces, and functionalised agarose or polyacrylamide surfaces. Polymers such as polyacrylamide have the further advantage that a functionalised oligonucleotide can be covalently attached during the polymerisation reaction between monomers (e.g. acrylamide monomers) that is used to produce the polymer. A functionalised oligonucleotide is included in the polymerisation reaction to produce a solid polymer containing covalently attached oligonucleotide. Such polymerisation represents a highly efficient means of attaching oligonucleotide to a solid material with control over the size, shape and form of the oligonucleotide-attached solid material produced.

Typically in order to attach an oligonucleotide probe to any such solid materials, the oligonucleotide is synthesised with a functional group at either the 3' or 5' end; although functional groups may also be added during the oligonucleotide production process at almost any base position. A specific reaction may then be performed between the functional group(s) within an oligonucleotide and a functional group on the relevant solid material to form a stable covalent bond, resulting in an oligonucleotide attached to a solid material. Typically such an oligonucleotide would be attached to the solid material by either the 5' or 3' end. Two commonly used and reliable attachment chemistries utilise a thiol (SH), or amine ($NH_3$) group and the functional group in the oligonucleotide. A thiol group can react with a maleimide moiety on the solid support to form a thioester linkage, while an amine can react with a succinimidyl ester (NHS ester) modified carboxylic acid to form an amide linkage. A number of other chemistries can also be used, including, without limitation: (i) Reaction of an amine group with an epoxide group to form an epoxyamine bond; (ii) reaction of a terminal hydrazide group on an oligonucleotide with an aldehyde, epoxide or ketone group on the solid surface to form a hydrazone bond; (iii) reaction of a alkyne group with an azide moiety to form a 1,2,3-triazole linkage via a click reaction; (iv) reaction of a tosyl group with a thiol or amine group to form an amine bond, and (v) the Solulink proprietary reaction chemistry between an aromatic aldehyde (4 FB) and an aromatic hydrazine-modified (HyNic) amine group to form a bis aryl hydrazone covalent bond. Amine modified glass surfaces, either pre modified or induced by silanization, can be utilized by reaction of the amine group with a succinimidyl ester (NHS ester), isothiocynate, or sulfonyl chloride to form an amino reactive intermediate. This group can then react with a terminal amine group on an oligo, or a thiol group if using a succinimidyl ester with a maleimide moiety on the opposite end such as N-Succinimidyl 4-(maleimidomethyl)cyclohexanecarboxylate (SMCC) or 4-(4-Maleimidophenyl)butyric acid N-hydroxysuccinimide ester (SMPB), to form a stable covalent linkages.

As well as chemical conjugation of an oligonucleotide probe to a solid material, it is possible and potentially advantageous to directly synthesise oligonucleotide probes on a solid material for use in the performance of the method. This again can be achieved by a number of methods including but not limited to techniques such as standard phosphoramidite chemistry for oligonucleotide synthesis on a solid material with a chemical linker attached to the solid material that is not broken by standard deprotection steps used in this methodology of oligonucleotide synthesis. Alternatively photolithography, a process commonly applied in microarray fabrication, can also be used to synthesise oligonucleotides directly onto a solid material.

In other embodiments one or more of the oligonucleotide probes is attached to a moiety that permits attachment of said oligonucleotide probe to a solid material. One strategy is to employ a method of affinity binding whereby a moiety that permits specific binding may be attached to the oligonucleotide probe such that the probe fragment either contains or does not contain said moiety, which thus enables differential separation of the probe fragment from the respective oligonucleotide probe to be performed. This may be performed, for example, using antibody-antigen binding or an affinity tag, such as a poly-histidine tag, or by using nucleic acid based hybridisation. An exemplary such moiety is biotin, which is capable of high affinity binding to streptavidin or avidin which itself is attached to beads or another solid surface. In one embodiment of the invention, the first oligonucleotide probe is incubated with the target nucleic acid in a nicking endonuclease cleavage reaction. Following an adequate time for the reaction to take place, an excess of streptavidin coated beads is added to the reaction. A biotin moiety present on the oligonucleotide probe but not probe fragment causes the full length oligonucleotide probe and remaining fragment to become attached to the beads. The beads are subsequently removed from the reaction, using centrifugation, or a magnet in the case of magnetic beads, and the supernatant is transferred to a subsequent reaction containing the second oligonucleotide probe.

In other embodiments, the probe fragment produced from the oligonucleotide probe in one or more of steps (a), (b), and optional steps (c) and (d), is separated from said oligonucleotide probe on the basis of its physicochemical properties, such as its size, sequence or charge, prior to the performance of the subsequent step. For example, any form of separation based on physicochemical properties such as size, sequence or charge of the smaller probe fragment from the larger oligonucleotide probe may be employed. Examples of techniques capable of separation of unmodified nucleic acids include, without limitation, capillary electrophoresis, gel electrophoresis, ion exchange, gel filtration, high performance liquid chromatography, dialysis and membrane filtration. Further the sequence difference between the probe fragment and the respective oligonucleotide probe, may be exploited for separation using differential hybridisation of the two species to complementary probes.

While it is envisaged that any nicking agent capable of cleaving the phosphodiester bond on a single strand of two duplexed nucleic acid molecules at an intended target site could feasibly be used in the performance of the method, nicking endonucleases are particularly well suited to the task. Nicking endonucleases are a subtype of type II restriction endonuclease enzymes that can catalyse the hydrolysis of the phosphodiester bond in the backbone of DNA molecules in a sequence specific manner. Table 1 provides a list of commercially available nicking endonucleases along with their known recognition sequence and cleavage site. Double-strand cleaving restriction endonucleases, of which a large number are available, can also be readily employed as nicking agents for use in the performance of the method, as described herein, providing a large number of enzymes from which to select the optimal nicking agent for a given target site and to optimise the parameters of the method (e.g. temperature and time). A number of other alternative types of enzyme could potentially be used or engineered to be suitable for performance of the method, such as, for example, a programmable nicking enzyme. One skilled in the art will recognise that a number of such programmable enzymes that are encoded by bacterial CRISPR-associated genes or 'Cas genes' and could potentially be exploited to specifically target any desired sequence through the use of a guide RNA sequence (Hsu et al. (2014) *Cell* 157, 1262). The CRISPR\Cas system, originally discovered as a conserved form of a prokaryotic immunity, is currently being employed in a number of areas of biotechnology for the purpose of precisely targeting DNA and RNA nucleic acid sequences for site specific cleavage, usually but not exclusively for the purpose of gene editing (Sander et al. (2014) *Nature Biotechnology* 32, 347). The programmable nature of these enzymes, make them ideal candidate enzymes to increase the repertoire of recognition sites available for oligonucleotide probe cleavage for use in the method. One advantage would be to provide a more convenient option than isolating or engineering a nicking agent for a particular target nucleic acid for which a nicking agent is not yet readily available. The extensive published work on programmable nicking enzymes, provides a proof of concept for the potential for them to be adopted directly as a nicking agent for the performance of the method.

Additionally, it is also envisaged that other enzymes may be used as nicking agents. A non-limiting list of examples would include enzymes such as RNaseH, DNAzymes, current or newly discovered, mutant or engineered versions of known restriction enzymes and newly discovered nicking endonucleases. Enzymes may be engineered by both rational design and/or directed evolution, which mimics the process of natural evolution to engineer new enzymes and functionalities in a controlled laboratory experiment. A number of nicking endonucleases from those currently commercially available have been engineered by rational modification of existing double-strand cleaving endonucleases of which a larger number are currently commercially available. Additionally, another potentially interesting nicking agent for the performance of the method could be the CEL I nuclease or 'surveyor enzyme'. This endonuclease has a novel ability to cleave mismatched base pairings, and cleave duplexed nucleic acid molecules when it recognises small insertions or deletions present between the two hybridised nucleic acid sequences. This could be of potential benefit in targeting certain probe for detection in which the sequence of interest is not precisely known, for example, targeting a region of unknown mutational status.

Thus, in one embodiment one or more of the nicking agents in steps (a), (b), and optional steps (c) and (d) is a naturally occurring enzyme, such as a nicking restriction endonuclease. Alternatively, one or more of the nicking agents in steps (a), (b), and optional steps (c) and (d) is an engineered enzyme, such as a mutated form of a naturally occurring enzyme or a DNAzyme. Alternatively, one or more of the nicking agents in steps (a), (b), and optional steps (c) and (d) is a programmable nicking enzyme.

TABLE 1

A list of commercially available nicking endonucleases.

| Nicking Enzyme | Recognition Sequence and Cleavage Site (5'-3') | Manufacturer Recommended Temp °C. | Engineered (Y/N) | Vendor |
| --- | --- | --- | --- | --- |
| Nt.BstNBI | GAGTCNNNN CTCAGNNNN | 55 | N | NEB |
| Nb.BsrDI | GCAATGNN CGTTACNN | 65 | N | NEB |
| Nb.BtsI | GCAGTGNN CGTCACNN | 37 | N | NEB |
| Nt.AlwI | GGATCNNNNN CCTAGNNNNN | 37 | Y | NEB |
| Nb.BbvCI | CCTCAGC GGAGTCG | 37 | Y | NEB |
| Nt.BbvCI | CCTCAGC GGAGTCG | 37 | Y | NEB |
| Nb.BsmI | GAATGCN CTTACGN | 65 | N | NEB |
| Nt.BsmAI | GTCTCNN CAGAGNN | 37 | Y | NEB |
| Nt.CviPII | CCD GGH | 37 | Y | NEB |
| Nt.BspQI | GCTCTTCN CGAGAAGN | 50 | Y | NEB |
| Nt.Bpu10I | CCTNAGC GGANTCG | 37 | Y | Life Technologies |
| Nb.Bpu10I | CCTNAGC GGANTCG | 37 | Y | Life Technologies |

In order to determine the presence of target nucleic acid, the probe fragment(s) produced is detected either during or at the end of a reaction, which can be accomplished by any technique which can detect the presence of the probe fragments produced following cleavage of the respective oligonucleotide probes. Alternatively the presence or level of the probe fragment can be inferred by detection of the presence or quantity of uncleaved oligonucleotide probe during or after a cleavage reaction. Simple embodiments of the invention may achieve such detection through the use of intercalating nucleic acid dyes, such as for example, SYBR gold, in conjunction with a size separation technique such as agarose gel electrophoresis, polyacrylamide gel electrophoresis (PAGE) or capillary electrophoresis. A large number of such intercalating dyes are available, such as, for example Ethidium bromide, SYBR green, picogreen, GelRed, GelStar etc. Other techniques that may be employed for the detection of nucleic acids such as probe fragment(s) which could be employed in embodiments of the method include: mass spectrometry (such as MALDI or LC-TOF), luminescence spectroscopy or spectrometry, fluorescence spectroscopy or spectrometry, liquid chromatography or fluorescence polarization.

For practical application of the invention, it may be advantageous to couple the performance of the method with a technique capable of quantitative and real-time detection of the formation of one or more probe fragment. A number of approaches which can achieve this are envisaged.

The components required for performance of the method, including nicking agent and oligonucleotide probes may be lyophilised for stable storage and the reaction may then be triggered by rehydration, such as upon addition of the sample.

In the simplest form colorimetric and fluorometric methods can be used to detect probe fragment(s) in step (e), without any modification to the oligonucleotide probes used in the method, by, for example, specifically binding or attaching dyes to the probe fragment(s) during or after the method.

Alternatively, one or more of the probe fragments produced in different steps (b), and optional steps (c) and (d) is attached to a moiety that permits its detection, such as a colorimetric or fluorometric dye or a moiety that is capable of attachment to a colorimetric dye e.g. biotin.

In an alternative approach, one or more of the probe fragments produced in step (b) and/or step (c) and/or step (d) is attached to an enzyme and the presence of said probe fragment is detected by contacting said enzyme with a substrate that yields a signal, such as a colorimetric or fluorometric signal, following action of the enzyme, wherein the presence of signal indicates the presence of the target nucleic acid in said sample. In an embodiment said substrate may be insoluble in water under the conditions employed in the cleavage reactions.

In one embodiment the detected probe fragments are detected using nucleic acid lateral flow. Nucleic acid lateral flow, wherein nucleic acids are separated from other reaction components by their diffusion through a membrane, typically made of nitrocellulose, is a rapid and low-cost method of detection capable of coupling with a range of signal read-outs, including colorimetric, fluorometric and electrical signals. The present invention is particularly amenable to use with nucleic acid lateral flow because the single-stranded probe fragments generated through the performance of the method readily flow along the membrane and are available for sequence specific detection via hybridisation. Thus in some embodiments the nucleic acid lateral flow detection utilises one or more oligonucleotide(s) that is capable of sequence specific hybridisation to one or more of the probe fragments. Alternative methods, such as PCR or polymerase based isothermal amplification methods, typically generate double-stranded DNA products, which are not available for detection based upon sequence specific hybridisation. Furthermore, the probe fragments to be detected are particularly amenable to multiplex detection, by virtue of the use of location specific hybridisation based detection.

In another approach, the presence of probe fragment(s) in step (e) is detected electrically, such as by a change in impedance resulting from the cleavage of one or more of the oligonucleotide probe(s).

Fluorometric detection can be achieved through the performance of any method which is based on the incorporation of an intercalating dye which binds to either single or double stranded nucleic acids. These types of dye, under appropriate excitation stimulus, emit fluorescent signal leading to subsequent detection of the target nucleic acid. Examples of such methods would include; quantitative PCR and in situ hybridisation methodologies. Other dyes for direct fluorescence detection include, without limitation: quantum dots, ALEXA dyes, fluorescein, ATTO dyes, rhodamine and Texas red. In embodiments of the method that employ a fluorescent dye moiety attached to an oligonucleotide probe or probe fragment, it is also possible to perform detection based on fluorescence resonance energy transfer (FRET), such as employed in Taqman quantitative PCR or Molecular Beacon based strategies for nucleic acid detection, whereby the signal would increase upon cleavage of an oligonucleotide probe to produce a probe fragment. Generally, when a fluorometric approach is used a number of different detectors devices can be used to record the generation of fluorescent signal, such as for example CCD cameras, fluorescence scanners, fluorescence based microplate readers or fluorescence microscopes.

Other embodiments of the invention use colorimetric signal to detect the presence of probe fragments. Such methods would have the advantage of not requiring an instrument to perform fluorescence excitation and detection and potentially of allowing the presence of target nucleic acid to be determined by eye. Colorimetric detection can be achieved by directly attaching a colorimetric dye or moiety to the oligonucleotide probe of interest prior to its use in the method, or alternatively specifically attaching or binding the dye or moiety to the probe fragment following cleavage. For example, a probe fragment(s) to be detected may contain a biotin moiety that permits its binding to a streptavidin conjugated colorimetric dye for its subsequent detection. One such example of a colorimetric dye that is widely used in detection assays is gold nanoparticles. Similar methods can be employed with a variety of other intrinsically colorimetric moieties, of which a very large number are known and widely used in biochemical research (such as carbon nanoparticles, silver nanoparticles, iron oxide nanoparticles, quantum dots etc.). Gold nanoparticles or other dyes could, for example, exist in the solid phase when attached to oligonucleotide probes that are attached to a solid surface, leading to a colourless aqueous phase. Cleavage of the oligonucleotide probe would then release the probe fragment and consequently the colorimetric dye into solution, which disperse and cause the appearance of colour in solution. A high extinction coefficient dye also provides potential for sensitive real-time quantification during the reaction.

In some embodiments of the invention, colorimetric dyes such as carbon or gold nanoparticles may also be detected using lateral flow, for example, on a nitrocellulose strip. As in aqueous embodiments, such carbon or gold nanoparticles may be released as a result of probe cleavage, but would migrate on the nitrocellulose strip. The released nanoparticles may still be attached to a fragment of oligonucleotide probe. A nitrocellulose strip would contain a probe complementary to the relevant probe fragment attached to the carbon or gold nanoparticles. Interaction between complementary probe on the nitrocellulose and gold particles causes local concentration of carbon or gold, causing appearance of a black or red colour, respectively. Alternatively the probe fragments to be detected would contain a moiety, such as a biotin, that permits their binding to a colorimetric dye prior to detection following the sequence specific hybridisation of the relevant probe fragment to a complementary oligonucleotide probe on a nucleic acid lateral flow strip, or a sandwich assay may be performed where the probe fragment produced hybridises to a dye-conjugated complementary oligonucleotide and also binds to a complementary third oligonucleotide immobilised on a lateral flow strip.

A number of considerations are taken into account when choosing an appropriate dye for a given application. For example, in embodiments where it is intended to perform visible colorimetric detection in solution, it would generally be advantageous to choose larger size particles and/or those with a higher extinction coefficient for ease of detection, whereas for embodiments incorporating a lateral flow membrane intended for visible detection, might benefit from the ability of smaller sized particles to more rapid diffuse along a membrane. While various sizes and shapes of gold nanoparticles are available, a number of other colorimetric moieties of interest are also available which include polystyrene or latex based microspheres/nanoparticles. Particles of this nature are also available in a number of colours, which can be useful in order to tag and differentially detect different oligonucleotide probe fragments during the performance of the method, or "multiplex" the colorimetric signal produced in a detection reaction.

Certain embodiments of the method involve one or more of the probe fragments being attached to an enzyme capable of generating a colorimetric or fluorometric signal after contacting said enzyme with a substrate. In this way the presence of the colorimetric or fluorometric signal corresponds to the presence of the probe fragment and therefore to the presence of the target nucleic acid in the sample. Some embodiments of the method use horseradish peroxidase (HRP) as the enzyme, which has been widely used as a reporter for ELISA, Western blot and immunohistochemistry applications. Its exceptionally high substrate turnover rate, and stability under relevant assay conditions (temperature, buffer and pH) make it particularly amenable to colorimetric reporting and signal amplification. Another reporter system involves the use of glycosyl hydrolase enzymes. This class of enzyme catalyses the hydrolysis of a polymeric sugar molecules, which can be synthesized with internal AZCL dye molecules. The sugar resides in the solid phase until enzymatic hydrolysis liberates dye molecules, which diffuse into solution. One example is endo-1,4-β-galactanase from *Clostridium thermocellum* which exhibits high specific activity and stability under assay conditions. Importantly, horseradish peroxidase and endo-1,4-β-galactanase can be conjugated efficiently to an oligonucleotide probe. Both enzymes also have relatively low molecular weight (40 kDa and 36 kDa respectively) which minimizes steric hindrance of probe cleavage event. Certain embodiments of the method could rely on alternative enzymes for generating a colorimetric signal. In theory, any enzyme which can be conjugated to an oligonucleotide probe and which can convert a substrate to a coloured product may be appropriate for use in the performance of the method. Suitable colorimetric enzymes might include: peptidases or amylases, esterases (e.g. carboxyesterase), glycosidases (e.g. galactosidase), and phosphatases (e.g. alkaline phosphatase). This list should not be considered in any way limiting.

The substrate for an enzyme used in detection may be insoluble in water, if such a substrate (e.g. AZCL Galactan in the case of Galactase or o-Dianisidine in the case of HRP) is insoluble in water under the aqueous conditions of the probe cleavage reaction, probe fragment conjugated to enzyme released into the aqueous phase following cleavage of an oligonucleotide probe attached to a solid material, would be able to access and digest the substrate to produce a colour change. In this way said enzyme may be used to produce a colorimetric signal in the presence of target nucleic acid in single pot reaction.

If a single oligonucleotide probe is used in the reaction and that probe is attached to an enzyme, during the reaction a directly proportional accumulation of probe fragment occurs in a first order reaction. However, if each molecule of probe fragment produced is attached to an enzyme then the signal is converted to a second order reaction; exponential accumulation of the colorimetric product of the relevant enzyme would occur during the reaction to indicate the presence of the target nucleic acid. In such an embodiment exponential signal amplification is achieved in the presence of target nucleic acid even if only a single oligonucleotide probe is employed in the method.

In a number of embodiments detection may be performed in a quantitative manner. Thus, the level of target nucleic acid in the sample may be quantified in step (e).

Further specific embodiments of the invention include the following:

A method for detecting the presence of a target nucleic acid of defined sequence in a sample which method comprises the steps:

a) contacting said sample with:
i. a first oligonucleotide probe attached to a solid material; and
ii. a nicking agent;
wherein the first oligonucleotide probe comprises a first complementarity region capable of sequence specific hybridisation to the target nucleic acid and a cleavage site for the nicking agent; and wherein the nicking agent specifically recognises double-stranded nucleic acid formed when the first oligonucleotide probe hybridises to the target nucleic acid in said sample and cleaves said first oligonucleotide probe to release a first probe fragment from said solid material;

b) contacting said first probe fragment with:
iii. a second oligonucleotide probe attached to a solid material; and
iv. a nicking agent;
wherein the second oligonucleotide probe comprises a second complementarity region capable of sequence specific hybridisation to the first probe fragment and a cleavage site for the nicking agent; and wherein the nicking agent specifically recognises double-stranded nucleic acid formed when the second oligonucleotide probe hybridises to the first probe fragment and cleaves said second oligonucleotide probe to release a second probe fragment from said solid material;

c) contacting said second probe fragment with:
v. a third oligonucleotide probe attached to a solid material and attached to a colorimetric dye or a moiety capable of attachment to a colorimetric dye; and
vi. a nicking agent;
wherein the third oligonucleotide probe comprises a third complementarity region capable of sequence specific hybridisation to the second probe fragment and a cleavage site for the nicking agent; and wherein the nicking agent specifically recognises double-stranded nucleic acid formed when the third oligonucleotide probe hybridises to the second probe fragment and cleaves said third oligonucleotide probe to release a third probe fragment attached to said colorimetric dye or moiety capable of attachment to a colorimetric dye from said solid material, wherein said third probe fragment is not capable of sequence specific hybridisation to the complementarity region of any one of the preceding oligonucleotide probes to form a site that is specifically recognised and cleaved by any of the said nicking agents; and d) detecting the presence of said third probe fragment produced at the end of step c) by colorimetric detection wherein the presence of a colorimetric signal indicates the presence of the target nucleic acid in said sample.

A kit comprising the following:
a. a first oligonucleotide probe attached to a solid material wherein said first oligonucleotide probe comprises:
i. a complementarity region [A] capable of sequence specific hybridisation to a target nucleic acid to form double-stranded nucleic acid that is specifically recognised by a nicking agent and that contains the cleavage site for said nicking agent; and
ii. a further complementarity region [B] which is separated from region [A] following cleavage at said cleavage site, and which is capable of sequence specific hybridisation to a second oligonucleotide probe to form a double-stranded nucleic acid that is specifically recognised by a nicking agent, and that contains the anti-sense sequence of the cleavage site for said nicking agent;

b. a second oligonucleotide probe attached to a solid material wherein said second oligonucleotide probe comprises:
i. a complementarity region [C] capable of sequence specific hybridisation to the complementarity region [B] in said first oligonucleotide probe to form a double-stranded nucleic acid that is specifically recognised by a nicking agent and that contains the cleavage site for said nicking agent; and
ii. a further complementarity region [D] which is separated from region [C] following cleavage at said cleavage site, and which is capable of sequence specific hybridisation to a third oligonucleotide probe to form a double-stranded nucleic acid that is specifically recognised by a nicking agent, and that contains the antisense sequence of the cleavage site for said nicking agent;

c. a third oligonucleotide probe attached to a solid material and attached to a colorimetric dye or a moiety capable of attachment to a colorimetric dye wherein said third oligonucleotide probe comprises:
  i. a complementarity region [E] capable of sequence specific hybridisation to the complementarity region in said second oligonucleotide probe to form a double-stranded nucleic acid that is specifically recognised by a nicking agent and that contains the cleavage site for said nicking agent; and
  ii. a second region attached to the colorimetric dye or moiety capable of attachment to a colorimetric dye, which is separated from region [E] following cleavage at said cleavage site, and which is not capable of sequence specific hybridisation to the complementarity regions of any of said preceding oligonucleotide probes to form a site that is specifically recognised and cleaved by any of the said nicking agents; and d. nicking agent(s) capable of cleaving the first oligonucleotide probe, second oligonucleotide probe and third oligonucleotide probe.

The method of the invention may also be used independently from the detection step (e) for amplifying a nucleic acid signal from a target nucleic acid of defined sequence, such a method may be used, for example, if the amplified signal is to be stored and/or transported for detection of the target nucleic acid at a future date and/or alternative location if required. The amplified signal comprises probe fragments of defined sequences produced through performance of the method. Thus in a further embodiment the invention provides a method of amplifying a nucleic acid signal from a target nucleic acid of defined sequence in a sample comprising steps (a), (b) and optional steps (c) and (d) of the method of the invention, wherein amplified nucleic acid is a probe fragment produced at the end of step (b) and/or step (c) and/or step (d) and wherein one or more of said amplified signal probe fragment(s) is not capable of sequence specific hybridisation to the complementarity region of any one of the preceding oligonucleotide probes to form a site that is specifically recognised and cleaved by any of the said nicking agents.

The current invention is of broad utility to various fields and applications which require detection of nucleic acid of defined sequence in a sample. It represents a fast, cheap and convenient means of determination of the presence of a target nucleic acid sequence within a sample. By way of a list of applications that is in no way limiting, we envisage that the invention could be of value in fields such as; diagnostics, forensics, agriculture, animal health, environment, defense, human genetic testing, prenatal testing, blood contamination screening, pharmacogenomics or pharmacokinetics and microbiological, clinical and biomedical research. Suitably the sample is a biological sample such as a human sample. The sample may be a human sample, a forensic sample, an agricultural sample, a veterinary sample, an environmental sample or a biodefence sample. It is envisaged that the invention would be amenable for use with a broad array of sample types, such as, for example: Nasal swabs or aspirates, nasopharyngeal swabs or aspirates, throat swabs or aspirates, cheek swabs or aspirate, blood or a sample derived from blood, urine or a sample derived from urine, sputum or a sample derived from sputum, stool or a sample derived from stool, cerebrospinal fluid (CSF) or a sample derived from CSF, and gastric fluids or a sample derived from gastric fluids, human or animal samples derived from any form of tissue biopsy or bodily fluid. The target nucleic acid may be (a) viral or derived from viral nucleic acid material (b) bacterial or derived from bacterial nucleic acid material (c) circulating cell-free DNA released from cancer cells (d) circulating cell-free DNA released from foetal cells or (e) micro RNA or derived from micro RNA inter alia.

The target nucleic acid may also be the product of reverse transcriptase, an RNA polymerase or a DNA polymerase. The target nucleic acid sequence may be naturally occurring or non-naturally occurring. The target nucleic acid may be generated in situ or produced from a naturally occurring nucleic acid prior to performance of the method. The target nucleic acid may, for example, be a probe fragment produced following cleavage of an oligonucleotide probe by a restriction enzyme other than a nicking agent, such as a double strand cleaving restriction endonuclease, of which a large number are available covering a broad range of recognition sequences. Said probe fragment may be produced by contacting a naturally occurring nucleic acid in a sample with such a double strand cleaving restriction endonuclease and an oligonucleotide comprising a first complementarity region capable of sequence specific hybridisation to said naturally occurring nucleic acid and a cleavage site for said restriction endonuclease; and wherein the restriction endonuclease specifically recognises double-stranded nucleic acid formed when said oligonucleotide probe hybridises to said naturally occurring nucleic acid in said sample and cleaves said oligonucleotide probe to produce the target nucleic acid for the method.

Generating the target nucleic acid for the method in this way has a number of potential advantages. For example, if a nicking agent could not be identified for a particular nucleic acid, a double strand cleaving restriction endonuclease, of which a greater number are currently known, could be employed to produce a target nucleic acid probe fragment containing a sequence that contains the antisense of a recognition sequence and cleavage site for a nicking agent to allow the method to be performed. Provided that the "real" nucleic acid in the sample to be detected is converted into the "surrogate" target nucleic acid for performance of the method with reliable conversion (which may be <1:1, 1:1 or 1:>1 i.e. possibly with some element of amplification) then detection of the "surrogate" target nucleic acid will allow the "real" nucleic acid to be detected and/or quantified.

It is also envisaged that the current invention has the potential to be of utility in screening samples for cell free DNA and epigenetic modifications such as, for example, CpG methylation of DNA sequences. Such epigenetic modification of particular cancer associated target genes can serve as useful biomarkers in a number of diseases and disease states. Methylation of nucleic acid recognition sequence is known to form part of the recognition site for certain nicking endonucleases, for example, Nt.BsmAI, Nt.CviPII and Nt.BbvCI are sensitive to CpG methylation at their recognition sequence. Given the growing appreciation of the importance of epigenetic modification in human disease, there is potential for the present invention to be used to specifically assess the epigenetic modification of particular target nucleic acid biomarkers. Therefore, in an embodiment, the region of the target nucleic acid capable of sequence specific hybridisation to the first complementarity region contains a site of epigenetic modification, such as methylation. Alternative the "real" nucleic acid used to produce a "surrogate" target nucleic acid for the performance of the method, as described above, contains a site of epigenetic modification.

Detection of target nucleic acid may be used for the diagnosis, prognosis or monitoring of disease or a diseased state such as an infectious disease, including but not limited to HIV, influenza, RSV, Rhinovirus, norovirus, tuberculosis, HPV, meningitis, hepatitis, MRSA, Ebola, *Clostridium difficile*, Epstein-Barr virus, malaria, plague, polio, *Chlamydia*, herpes, gonorrhoea, measles, mumps, rubella, cholera or smallpox, or cancer, including but not limited to colorectal cancer, lung cancer, breast cancer, pancreatic cancer, prostate cancer, liver cancer, bladder cancer, leukaemia, esophageal cancer, ovarian cancer, kidney cancer, stomach cancer or melanoma, or in the fields of human genetic testing, prenatal testing, blood contamination screening, pharmacogenetics or pharmacokinetics.

The presence of two or more different target nucleic acids of defined sequence may be detected in the same sample. In an embodiment of the method, two or more separate sequential series of oligonucleotide probes may be employed on the same sample and/or used simultaneously. For example, in an embodiment, one set of oligonucleotide probes would be used for the detection of one target nucleic acid in a sample and another set of oligonucleotide probes would be used for the detection of another target nucleic acid in the same sample. The detection of the probe fragment(s) produced from the two or more different sets of probes could each be coupled to a particular signal, such as different colorimetric or fluorometric dyes or enzymes, to allow multiplex detection. The fact that the probe fragment(s) to be detected are single-stranded nucleic acids, typically released into the aqueous phase from a solid material, enables their subsequent differential detection based upon sequence specific hybridisation, which means the present invention possesses a powerful advantage over other methods in terms of its multiplexing capability (see Example 3). For example, most polymerase-based methods produce a double-stranded nucleic acid product, which would not be suitable for subsequent detection based upon sequence-specific hybridisation. Furthermore, typically one or more of the detected probe fragment(s) produced is not capable of sequence specific hybridisation to the complementarity region of any of the oligonucleotide probes used in the performance of the method to form a site that is specifically recognised by a nicking agent, thereby avoiding competition for binding to said probe fragment(s) wherein such oligonucleotide probes would act as a 'sink' thus hampering the ability to detect said probe fragment(s). Instead, in certain embodiments of the present invention an 'end-point' detection system is employed wherein said probe fragment(s) accumulate without such competitive binding, enabling its efficient subsequent detection. In certain embodiments, multiple different probe fragments produced from different series of oligonucleotide probes can be differentially detected using nucleic acid lateral flow, wherein multiple oligonucleotides comprising complementary sequence to each of the probe fragment(s) are each immobilised on the nitrocellulose membrane in a discrete location; thus a single colorimetric dye can be used for simultaneous detection of many different target nucleic acids in the same sample.

In alternative embodiments two or more variants of the first oligonucleotide probe could be used to detect different target nucleic acids; whilst the probe fragment from both probes would hybridise to the same second oligonucleotide probe and therefore link to the same sequential series of probes and, ultimately, the same detection signal. More generally, any probe fragment may be designed to hybridise to almost any other oligonucleotide probe employed in the method, by virtue of the flexibility in the design of the complementarity regions of the oligonucleotide probes. In some embodiments it is considered to be advantageous for none of the probe fragments to be capable of sequence specific hybridisation to the first complementarity region of the first oligonucleotide probe. There is typically no requirement for the oligonucleotide probes of the present method to produce functional equivalents of the target nucleic acid for its use in the detection of said target nucleic acid, as is the case for methods such as PCR. By avoiding a "closed loop" amplification cycle in this way, considerably increased versatility in multiplexing is conferred. Furthermore, the sequence of all of the oligonucleotide probes apart from the first oligonucleotide probe can be defined, enabling the same reagents to be employed for the amplification and detection of many different target nucleic acids by replacing only the first oligonucleotide probe; a 'universal amplification and detection system'.

The following examples serve to further illustrate various aspects and embodiments of the methods described herein. These examples should not be considered limiting in any way.

EXAMPLES

Materials and Methods

The following materials and methods are used in the examples below unless otherwise indicated. Oligonucleotides: Except as otherwise indicated custom oligonucleotides were manufactured using phosphoramidite method by Eurofins Genomics or Integrated DNA Technologies.

Custom oligonucleotide probes synthesised for use in situ on polystyrene resin were manufactured by ATDBio Ltd. Oligonucleotide probes were sequentially manufactured on the polystyrene matrix using an irreversible linker before de-protection by alkaline treatment. To prepare oligonucleotide attached polystyrene resin prior to use in reactions, approximately 1 mg of resin was extensively washed over a 0.45 µm PVDF filter membrane (Millipore) with 150 ml, 1×PBS (pH 7.5) and subsequently recovered in an appropriate volume, typically 300 µl of the digestion buffer for the relevant nicking enzyme (e.g. 1× Buffer 3.1 or 1× CutSmart buffer (New England Biolabs)). Attachment of oligonucleotide probe to streptavidin magnetic beads: Streptavidin-coupled beads are super paramagnetic beads used for attaching biotin containing biomolecules to a solid matrix in a variety of applications. They can be efficiently bound to biotinylated oligonucleotides probes. To ensure complete absorption of biotinylated oligonucleotides and avoid the presence of unbound oligonucleotide in solution when generating reagents for performance of the method, beads were typically saturated to approximately 50% of their binding capacity. In a standard coupling reaction streptavidin magnetic beads (C1 Dynabeads, Life technologies) were prepared by washing by incubation at 2 mg/ml (w/v) in 2×BW buffer (10 mM Tris HCl (pH 7.5), 1 mM EDTA, 2M NaCl) at room temperature for one minute. Beads were then recovered using a magnet and washed at 2 mg/ml in 1×BW buffer at room temperature for one minute. For coupling, beads were resuspended in at 2 mg/ml in 1×BW buffer with 25 pmol of biotinylated oligonucleotide per 100 µg of streptavidin beads. This mixture was incubated for 30 minutes at room temperature, shaking vigorously. After conjugation, the beads were thoroughly washed according to the manufacturer's protocol and resuspended in appropriate buffer for immediate use or storage.

Attachment of oligonucleotide to carboxylic acid beads: Carboxylic acid beads (MyOne, Life Technologies) are 1 µm, mono-sized super paramagnetic beads with a highly cross-linked polystyrene surface functionalised with carboxylic acid groups. Amine modified oligonucleotide probes can be reacted with the beads in the presence of a suitable carbodiimide cross-linking reagent, such as 1-ethyl-3-(3-dimethylaminopropyl) carbodiimide (EDC). The reaction forms an amide bond rendering the amine modified oligonucleotide probe immobilised on the bead surface. In a standard coupling reaction protocol 1.2 mg of Dynabeads MyOne Carboxylic acid beads were prepared by washing twice at room temperature in 1×PBS for 5 minutes. Following each wash the beads were recovered by magnet pull-down and the supernatant was discarded. Beads were then added to conjugation reactions in 100 µl of 100 mM MES buffer (pH 4.8), containing 200 mM EDC (added from freshly prepared 1M EDC stock) and 4.8 nmol of amine modified oligonucleotide and incubated at room temperature for 2 hours with vigorous shaking. Following the reaction, beads were recovered using a magnet, the supernatant was discarded and the beads were quenched by addition of 500 of 50 mM ethanolamine solution in 1×PBS (pH 8.0) for 60 minutes at room temperature with shaking. The beads were then washed three times in 1 ml PBS (pH 7.4)+0.1% TWEEN® 20 (polyoxyethylenesorbitan monolaurate) for 2 minutes with mixing and re-suspended in appropriate buffer for immediate use or storage.

Traut's reagent conversion of Amine modified oligonucleotide to sulfhydryl: A reaction was prepared containing 100 pmol/µl amine modified oligonucleotides, 2 nmol/µl Traut's reagent (2-iminothiolane) and 1 mM EDTA in 1×PBS (pH 8.0) and incubated at room temperature for one hour with shaking. Subsequently, removal of excess Traut's reagent and clean-up was performed using a 7 kDa MWCO desalting column (Zeba Spin Desalting Column, Life Technologies) equilibrated with 1×PBS (pH 7.2)+1 mM EDTA, following the manufacturer's protocol. The thiol modified oligo produced was used directly for maleimide bead coupling as described below. In order to prepare sulfhydryl oligonucleotide for conjugation to maleimide-activated proteins the protocol was performed as described above but at 200 pmol/µl amine modified oligonucleotides and 4 nmol/µl Traut's reagent.

Attachment of oligonucleotide probe to maleimide beads: Maleimide beads (Cube Biotech GmbH) are spherical 25 µm diameter magnetic beads coated with 6% cross-linked agarose. The maleimide moiety is coupled to the magnetic agarose via an epoxide function and C40 spacer to obtain a high binding capacity for conjugation to thiol groups and reduced non-specific binding. Thiol modified oligonucleotide probes can be conjugated to the beads in order to create a stable covalent thioether bond. In a standard coupling reaction 30 mg (120 µl of 25% w/v suspension) of maleimide activated beads were prepared by washing four times in 1×PBS (pH 7.2)+1 mM EDTA. Following each wash the beads were recovered by magnet pull-down and the supernatant was discarded. 4 nmol of thiol modified oligonucleotide was incubated for one hour at room temperature with shaking in 40 µl of 1×PBS (pH 7.2) containing 10 mM TCEP and 1 mM EDTA. The oligonucleotide was then desalted using a 7 kDa MWCO desalting column (Zeba Spin Desalting Column, Life Technologies) equilibrated with 1×PBS (pH 7.2)+1 mM EDTA and added to the 30 mg beads. For thiol oligo prepared by Traut's treatment, TCEP treatment of the oligo is omitted and 4 nmol oligo was added directly to 30 mg beads in 40 µl of 1×PBS (pH 7.2)+1 mM EDTA. In each case the conjugation reaction was incubated for two hours at room temperature with shaking. The beads are then washed six times in 1×PBS (pH 7.4) with 0.1% TWEEN® 20 (polyoxyethylenesorbitan monolaurate) and twice in 1×PBS (pH 7.4), before resuspension in an appropriate buffer for storage or use.

Polyethylenimine (PEI) precipitation protocol: PEI precipitation was performed to remove excess free oligonucleotide from oligonucleotide conjugated protein. 0.125 mg/ml oligonucleotide-conjugated enzyme in 0.5×PBS (pH 7.0), 0.375M NaCl and 0.02% (w/v) polyethylenimine (PEI) (Sigma Aldrich) was vortexed vigorously for 1 minute and incubated on ice for 5 minutes. Reactions were then centrifuged at 7,500×g for five minutes. Supernatant was recovered and 5 µl was run on 15% TBE-Urea polyacrylamide gel, stained using SYBR Gold (Life Technologies) to verify oligo removal. If oligonucleotide was still visible on gel, the process was repeated until complete removal was achieved.

Polyacrylamide Gel electrophoresis (PAGE): Samples were separated using 15% polyacrylamide, 7M urea gels using standard procedures described in detail elsewhere (Sambrook, J., and Russell, D. 2001) Molecular Cloning a laboratory manual, Third Ed. Cold Spring Harbor Press).

Carbon Nucleic Acid Lateral Flow Assay: Carbon nanoparticles were conjugated via non-covalent adsorption to various biotin-binding proteins, e.g. streptavidin. Typically, a colloidal carbon suspension was prepared in Borate Buffer followed by sonication using a probe sonicator. Carbon was subsequently adsorbed to biotin-binding protein by incubation at room temperature before being extensively washed. Carbon was applied to glass fibre conjugate pad before being air dried. Typically, additives, e.g. BSA, were added to the buffer used for washing and drying the carbon. Lateral flow strips were constructed by combining a dried carbon conjugate pad, with a sample pad, nicrocellulose membrane and adsorbent pad (Merck Millipore) following the manufacturer's guidelines. Prior to its use in lateral flow strips, the relevant oligonucleotide(s) containing the reverse complement of the sequence of the probe fragment(s) to be detected in the method were printed onto the nitrocellulose membrane at a defined location and attached to the membrane via UV cross-linking.

TABLE 2

| Oligonucleotide probe sequences used in the examples (* = phosphorothioate internucleotide linkage). | |
|---|---|
| ID | Oligonucleotide Sequences (5'-3') |
| P1 | GCATCTCTATGACTCAAGAGTCTGTCCATCACGATATATATATATAT |
| P2 | GTGATGGACAGACTC |
| P3 | ATATATATATATATATTTGAGTCATAGAGATGCCGAGACTCCT |

TABLE 2-continued

Oligonucleotide probe sequences used in the examples
(* = phosphorothioate internucleotide linkage).

| ID | Oligonucleotide Sequences (5'-3') |
|---|---|
| P4 | ATATATATATATATGTAAAAGAGTCTGTCCATCACTTCTGTATCTGGGACTCTAAAG |
| P5 | ATATATATATATATCTTTAGAGTCCCAGATACAGATTATGCAAGTGATGACTCATAG |
| P6 | GAATCGAGACGAAAAGAGTCTGTCCATCACATATATATATAT |
| P7 | ATATATATATATATTTTCGTCTCGATTCGATATCTTGACTCCTT |
| P8 | ATATATATATAGGAGTCTCGGCATCTATATATATATAT |
| P9 | ATATATATATATCTATGAGTCATCACTTGCATAAATATATATAT |
| P10 | ATATATATATATTAAACCAAGTACCGCACTATATATATAT |
| P11 | TGCCATCCACCTTATGTATATA |
| P12 | ATATATATATATATAGGAGTCTCGGCATCTATATATATATATAT |
| P13 | ATATATATATGTAAAAGAGTCTGTCCATCACTATATATATA |
| P14 | TTTTTTTTTTTTTTGAGAGCCAGGACCAGGAACACA |
| P15 | TTTTTTTTTTTTTTTGTGTTCCTGGTCCTGGCTCTC |
| P16 | ATATATATATGTAAAAGAGTCTGTCCATCACTATATATAT |
| P17 | AAAAAAAAAAGTAAAAGAGTCTGTCCATCACTAAAAAAAAAA |
| P18 | AAAAAAAAAAAAAAGAGTCTGTCCATCACAAAAAAAAAAA |
| P19 | AAAAAAAAAAAAGAGTCTGTCCATCACAAAAAAAAAAA |
| P20 | AAAAAAAAAAAAGAGTCTGTCCATCAAAAAAAAAA |
| P21 | ATTAATACCATCAAAATGTATATAT |
| P22 | ATATATAC*ATTTTGATGGTAT |
| P23 | ATATATAC*ATTTTGAAGGTAT |
| P24 | ATTTTGATGGTAT |
| P25 | TTACTGAGGATATTGCTTGAAGCTGGCAGTGCCTCTCGATCCGAATGCTCAGAGACAGAAGAGCGCAATGGGGACTCTTACTGAGGATATTGCTTGAAGCTG |
| P26 | ATATATATATCGCAGTCTCTGAATATATATATAT |
| P27 | AAAAAAAAAGAGAGGCACTGCCAGCTTAAAAAAAAAA |
| P28 | ATATATATACGCCAGCCATTGCAACAGGAATATATATAT |
| P29 | TTTTATATATATATGTAAAAGAGTCTGTCCATCACTATATATATA |
| P30 | TTTTTTTTATATATATATGTAAAAGAGTCTGTCCATCACTATATATATA |

Example 1

Detection of Target Nucleic Acids Using Polyacrylamide Gel Electrophoresis to Detect Probe Fragments In this example we performed detection of control target nucleic acids using different embodiments of the method to demonstrate key aspects, such as sensitivity resulting from the intrinsic exponential amplification. We used the M13mp18 bacteriophage (NEB), a single-stranded viral DNA, or synthetic DNA oligonucleotides as control target nucleic acids. In each case, detection of probe fragments was performed using polyacrylamide gel electrophoresis, stained with SYBR Gold.

Two Oligonucleotide Probes in Sequential Aqueous Reactions

We first performed the method using two oligonucleotide probes in sequential aqueous reactions to detect M13mp18. A first oligonucleotide probe (P1), was designed with a 5' region complementary to a region within M13mp18 and that also contained the recognition sequence and cleavage site for the nicking endonuclease Nt.BstNBI. The probe was manufactured with a 3' Biotin TEG modification. Digestion reactions were assembled with 5 pmol of the oligonucleotide probe (P1), 5 U Nt.BstNBI (NEB), 5 μl of 10×NEB buffer 3.1 (NEB), either 10 ng or 0 ng M13mp18 and dH$_2$0 to a final reaction volume of 50 μl. Reactions were mixed using a pipette and incubated at 55° C. for 20 minutes. Following incubation reactions were added to 0.1 mg of Dynabeads (C1 streptavidin magnetic beads, Life Technologies), washed twice in 1 ml of 1×BW buffer, and subsequently once with 100 μl of 1× buffer 3.1 (NEB), in a fresh tube and incubated for ten minutes at room temperature. The beads were removed using a magnet and the supernatant transferred to a fresh tube containing 0.1 mg Dynabeads (T1, streptavidin magnetic beads, Life Technologies) which had been coupled to a 3' biotin TEG modified oligonucleotide probe (P2), as described in the general methods section. The purpose of this step was to hybridise any remaining full length oligonucleotide probe P1 to a complementary oligonucleotide probe, P2, and subsequently remove it but not cleaved probe fragments, from the reaction. The tube was incubated for 10 minutes at 35° C., slowly cooled to room temperature and then incubated for twenty minutes at 4° C. The beads were removed using a magnet and the supernatant removed and passed through a 0.45 μm mixed cellulose filter (Alpha Laboratories).

Figure 3A:
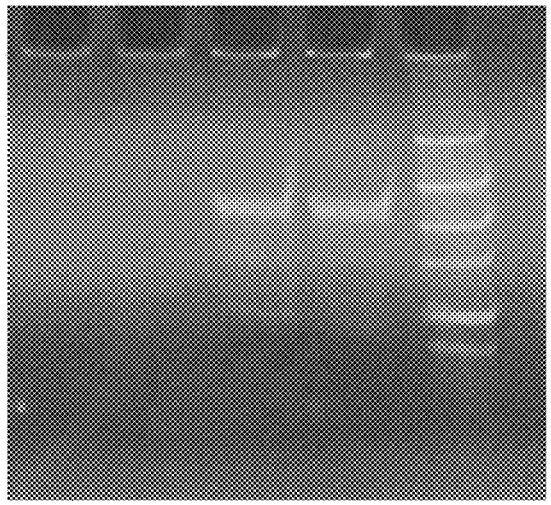
FIG. 3A. Two oligonucleotide probes in sequential aqueous reactions (see Example 1).

5 μl of the recovered filtrate was used to assemble a second probe digestion reaction with the following additional components: 5 pmol of the second oligonucleotide probe (P3) 5 U Nt.BstNBI (NEB), 1 μl 10×NEB buffer 3.1 (NEB) and dH$_2$O to a final reaction volume of 10 μl. The second oligonucleotide probe was manufactured with a 5' biotin TEG modification. The second probe digestion reaction was incubated for twenty minutes at 55° C. Following this, the entirety of each reaction and 10 μl of the purified first probe digestion reactions were analysed by TBE-Urea polyacrylamide gel electrophoresis (PAGE) using a 15% w/v gel stained with SYBR Gold (Life Technologies) and visualised using a UV transilluminator (FIG. 3A). No full length oligonucleotide probe or probe fragments were visible in the initial probe digestion reactions (FIG. 3A; lanes 1 and 2). In contrast, after the second step substantial cleavage of the second oligonucleotide probe evidenced by the presence of the second probe fragment was observed only in the presence of target (FIG. 3A; lanes 3 and 4). This example demonstrates the detection of target nucleic acid using a two probe embodiment of the method where the oligonucleotide probe digestion reactions was performed in aqueous.

Two Oligonucleotide Probes in Sequential Reactions with Both Probes Attached to Solid Material (Streptavidin Magnetic Beads)

Figure 3B:
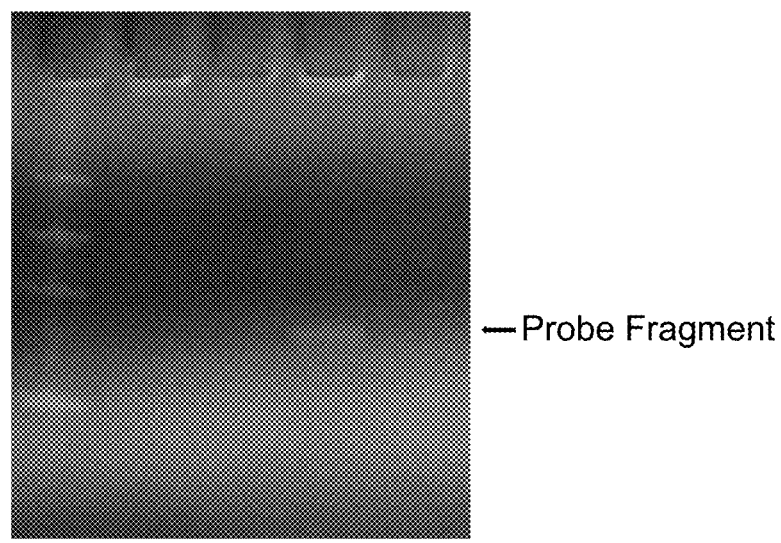
FIG. 3B. Two oligonucleotide probes in sequential reactions with both probes attached to a solid material (streptavidin magnetic beads) (see Example 1).

We next performed the method to detect a target nucleic acid (M13mp18) using two oligonucleotide probes attached to streptavidin beads in sequential reactions. To do this, Dynabeads (C1 streptavidin magnetic beads, Life Technologies) were coupled to a 5' biotin TEG modified first oligonucleotide probe (P4) and a 5' biotin TEG modified second oligonucleotide probe (P5), as described in the general methods section. Cleavage reactions were prepared containing 0.05 mg P3 beads (approximately 25 pmol of probe P4), 5 U Nt.BstNBI (NEB), 1 μl of 10×NEB buffer 3.1 (NEB), either 100 ng or 0 ng of M13mp18 and dH$_2$0 to a final reaction volume of 10 μl. The reaction was incubated for twenty minutes at 55° C. Following incubation, beads were magnetically pelleted and the supernatant transferred to a fresh tube containing 0.1 mg of uncoupled Dynabeads (C1 streptavidin magnetic beads, Life Technologies), which had been washed twice in 1 ml of 1×BW buffer, and once with 100 μl of 1×NEB buffer 3.1. The tubes were incubated for ten minutes at room temperature, and the beads were removed using a magnet. The supernatant was transferred to a fresh tube containing 0.05 mg of P5 beads (approximately 25 pmol of probe P5). The reaction was incubated for twenty minutes at 55° C. Following this, the entirety of each second probe cleavage reaction and 10 μl of the purified first probe cleavage reactions were analysed by TBE-Urea polyacrylamide gel electrophoresis (PAGE) using a 15% w/v gel stained with SYBR Gold (Life Technologies) and visualised using a UV transilluminator (FIG. 3B). No cleavage bands were visible after the first step (lanes 1 and 2). A band corresponding to the size of the second probe fragment was visible only in the presence of target nucleic acid (lane 4) and not in the absence of target nucleic acid (lane 3). This example demonstrates detection of a target nucleic acid using a two probe embodiment of the method with two sequential steps and oligonucleotide probes attached to a solid material (streptavidin beads).

Two Oligonucleotide Probes in Sequential Reactions with the First Probe Attached to Solid Material (Maleimide Beads).

First, the method was performed using two oligonucleotide probes with covalent attachment of the first oligonucleotide probe to a solid material, maleimide beads. A first oligonucleotide probe (P1) was designed with a 3' region that is complementary to a region within M13mp18 and that contains the recognition sequence and cleavage site for the nicking endonuclease Nt.BstNBI, and a 5' region that includes the anti-sense of the recognition sequence and cleavage site for Nt.BstNBI. The probe was manufactured with a 3' amine modification. A second 5' amine modified oligonucleotide probe (P3) was designed that contains the reverse complementary sequence to the 5' region of the first oligonucleotide probe, which therefore contains the recognition sequence and cleavage site for Nt.BstNBI.

The first oligonucleotide probe was converted to a sulfhydryl group and used to conjugate the oligonucleotide to maleimide beads as described. The beads were then extensively washed to remove any unbound probe remaining following the conjugation procedure. Four digestion reactions were assembled with the maleimide bead-oligonucleotide conjugate. A quantity of the bead-oligonucleotide conjugate containing approximately 15 pmol of oligonucleotide probe was added to each of four cleavage reactions containing 5 U Nt.BstNBI (NEB), 1 μl of 10×NEB buffer 3.1 (NEB), 1 μl of M13mp18 and dH$_2$0 to a final reaction volume of 10 μl. M13mp18 was added at four levels: 10 ng, 100 pg, 1 pg and 0. Reactions were mixed using a pipette and incubated at 55° C. for 1 hour.

Figure 4A:
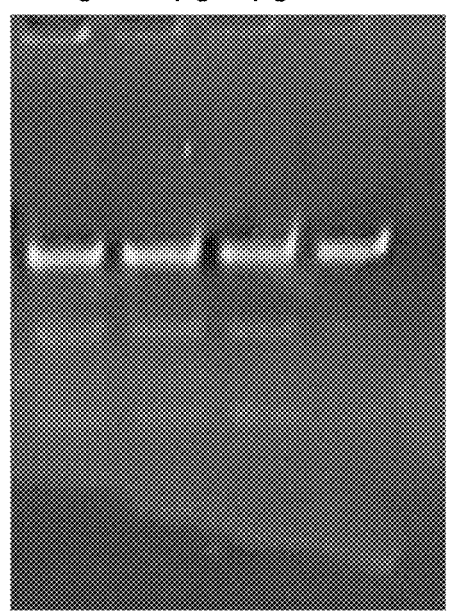
FIG. 4A. Two oligonucleotide probes in sequential reactions with first probe attached to a solid material (maleimide beads) (see Example 1).

Following incubation, the beads were removed from each reaction using a magnet and the supernatants were recovered and heated to 85° C. for 5 minutes to denature the enzyme and prevent further cleavage. 1 μl of each supernatant was transferred into a subsequent reaction containing 5 pmol of the second oligonucleotide probe (P3), 5 U Nt.BstNBI (NEB), 1 μl 10×NEB buffer 3.1 (NEB) and dH$_2$O to a final reaction volume of 10 μl. Reactions were mixed by pipette and incubated at 55° C. for 30 minutes and then at 85° C. for 5 minutes. The entirety of each reaction was then analysed by TBE-Urea polyacrylamide gel electrophoresis (PAGE) using a 15% w/v gel stained with SYBR Gold (Life Technologies) and visualised using a transilluminator. Results are displayed FIG. 4A. The product(s) of cleavage of the second oligonucleotide (P3) were observed at all levels of M13mp18 tested (lanes 1-3) and not observed in the absence of target (lane 4). The example demonstrates the ability of a two probe embodiment of the method to detect 1 pg of target nucleic acid (lane 3), which evidences sensitive detection resulting from the exponential amplification effect achieved through the use of sequential probes in the method. The ability to detect 1 pg of M13mp18 using two oligonucleotide probes in the timeframe tested is consistent with the sensitivity of detection predicted in our model of the reaction displayed in FIG. 2. Using a single oligonucleotide probe, without exponential signal amplification, it would take over 25 hours for 1 pg to be detected, assuming that the enzyme retained stability and that the reaction rate remained unchanged during that time.

Two Oligonucleotide Probes in Sequential Reactions with the First Probe Attached to Solid Material (Polystyrene Beads)

We next performed the method using two distinct oligonucleotide probes, the first of which was synthesised and prepared for use directly on a polystyrene resin. The aim of this example was to demonstrate the sensitivity of the method using different probe sequences, alternating nicking endonucleases between steps and using an alternative solid material. To do this, a first oligonucleotide probe (P6) was designed with a 3' region complementary to a region within M13mp18 that contains the recognition sequence and cleavage site for the nicking endonuclease Nt.BstNBI, and a 5' region that includes the anti-sense of the recognition sequence and cleavage site for Nt.BsmAI. A second probe (P7) was designed that contains the reverse complementary sequence to the 5' region of the first oligonucleotide probe, containing the recognition sequence and cleavage site for Nt.BsmAI.

Polystrene resin attached to the first oligonucleotide probe (P6) was manufactured by ATDBio Ltd and prepared as described. An amount of polystyrene resin containing approximately 15 pmol of the first oligonucleotide probe was added to each of four cleavage reactions containing 5 U Nt.BstNBI (NEB), 1 µl of 10×NEB buffer 3.1 (NEB), 1 µl of M13mp18 and dH$_2$0 to a final reaction volume of 10 µl. M13mp18 was added at four levels: 10 ng, 100 pg, 1 pg or 0. Reactions were mixed using a pipette and incubated at 55° C. for 1 hour.

Following incubation, the polystyrene resin was removed from each sample by centrifugation at 7,500×g for 2 minutes. In order to remove any remaining polystyrene particles the samples were subjected to a filtration step, by first diluting the sample in Cutsmart buffer (NEB) to a total volume of 30 µl and then passing it through a 13 mm, 0.45 µm mixed cellulose ester syringe filter (Alpha Labs).

Figure 4B:
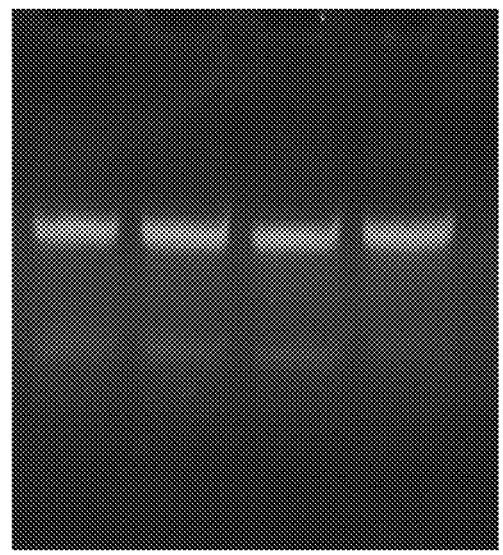
FIG. 4B. Two oligonucleotide probes in sequential reactions with first probe attached to a solid material (polystyrene beads) (see Example 1).

1 µl of each recovered filtrate was transferred into a subsequent reaction containing 5 pmol of the second oligonucleotide probe, 2.5 U Nt.BsmAI (NEB), 1 µl 10×NEB CutSmart (NEB) and dH$_2$O to a final reaction volume of 10 µl. Reactions were mixed by pipette and incubated at 45° C. for 30 minutes and then 85° C. for 5 minutes. The entire reactions were then analysed by TBE-Urea polyacrylamide gel electrophoresis (PAGE) using a 15% w/v gel stained with SYBR Gold (Life Technologies) and visualised using a transilluminator. Results are displayed in FIG. 4B. The product(s) of cleavage of the second oligonucleotide (P7) were observed at all levels of M13mp18 tested (lanes 1-3) and not observed in the absence of target (lane 4). The example demonstrates the ability of a two probe embodiment of the method with polystyrene as the solid material and different nicking agents is also capable of detecting 1 pg of target nucleic acid (lane 3), evidencing sensitive detection resulting from the exponential amplification effect achieved through the use of sequential probes in the method.

Three Oligonucleotide Probes in Sequential Reactions with First Two Probes Attached to Solid Material (Streptavidin Magnetic Beads)

We next performed the detection of M13mp18 using three oligonucleotide probes. To do this, oligonucleotide probes P1 and P3 were attached to streptavidin beads using a standard protocol as previously described. The streptavidin beads attached to oligonucleotides were washed extensively to remove unbound probe. An amount of streptavidin beads containing approximately 25 pmol of the first oligonucleotide probe was added to each of two cleavage reactions containing 5 U Nt.BstNBI (NEB), 1 µl of 10×NEB buffer 3.1 (NEB), 1 pg or 0 pg of M13mp18 and dH$_2$0 to a final reaction volume of 10 µl. Reactions were mixed using a pipette and incubated at 55° C. for 1 hour.

Following incubation, the beads were removed from each sample using a magnet. 4 µl of each supernatant was transferred into a second oligonucleotide digestion reaction containing an amount of streptavidin beads attached to approximately 25 pmol of the second oligonucleotide probe (P3), 5 U Nt.BstNBI (NEB), 1 µl 10×NEB buffer 3.1 (NEB) and dH$_2$O to a final reaction volume of 10 µl. Reactions were mixed by pipette and incubated at 55° C. for 1 hour.

Figure 5:
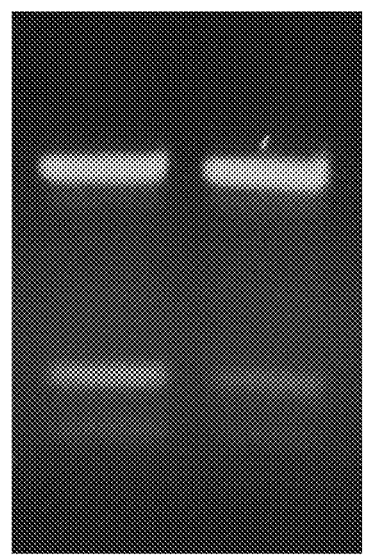
FIG. 5. Three oligonucleotide probes in sequential reactions with first two probes attached to a solid material (streptavidin magnetic beads) (see Example 1).

Following incubation, the beads were removed from each sample using a magnet. 3.4 µl of each supernatant was transferred into a third oligonucleotide digestion reaction containing 5 pmol of a third oligonucleotide probe (P8), 5 U Nt.BstNBI (NEB), 1 µl 10×NEB buffer 3.1 (NEB) and dH$_2$O to a final reaction volume of 10 µl. Reactions were mixed by pipette and incubated at 55° C. for 30 min. The third oligonucleotide probe was designed to contain a region complementary to the probe fragment released following cleavage of the second probe that also contains the recognition sequence and cleavage site for the nicking endonuclease Nt.BstNBI. Following incubation, the entirety of each reaction was analysed by TBE-Urea polyacrylamide gel electrophoresis (PAGE) using a 15% w/v gel stained with SYBR Gold (Life Technologies) and visualised using a transilluminator. Results are displayed in FIG. 5. The cleavage products of the third oligonucleotide probe are markedly more visible in the presence of target nucleic acid (lane 1) although a low level of background signal was observed (lane 2). The example demonstrates the ability of a three probe embodiment of the method to detect target nucleic acid and the use of the streptavidin biotin interaction to readily separate oligonucleotide probe from the probe fragment produced following cleavage.

Two Oligonucleotide Probes in a Single-Pot Reaction with Both Probes Attached to Solid Material (Streptavidin Magnetic Beads)

Figure 6:
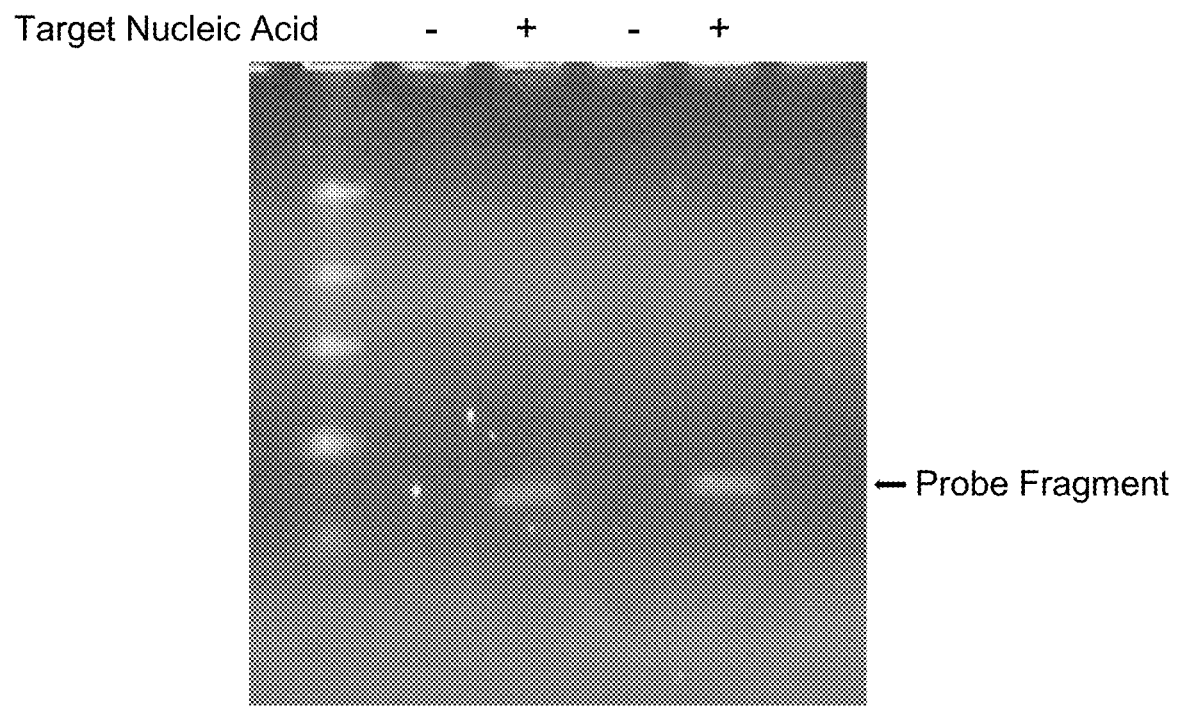
FIG. 6. Two oligonucleotide probes in a single-pot reaction with both probes attached to a solid material (streptavidin magnetic beads) (see Example 1).

Various embodiments of the invention encompass multiple probe cleavage reactions being performed simultaneously in a single reaction. In the present example we have demonstrated this with two oligonucleotide probes (P5 and P9) for the detection of an oligonucleotide target nucleic acid (P4). Oligonucleotide probes P5 and P9 each manufactured with biotin modification on their 5' end were coupled to Dynabeads as described in the general method section. Next, two sets of detection reactions were prepared with varying ratios of the first to the second oligonucleotide probe. The first set of reactions were prepared using a 1:150 ratio of the first to the second oligonucleotide. Reactions were prepared containing 5 U Nt.BstNBI (NEB), 1 µl of 10×NEB buffer 3.1 (NEB), 0.05 pmol of target nucleic acid (P4 oligonucleotide), 0.167 pmol of a streptavidin bead-oligonucleotide conjugate (P5) and 25 pmol of Streptavidin bead-oligonucleotide conjugate (P9) in dH$_2$0 to a final reaction volume of 10 µl. The second set of reactions were prepared with a 1:200 ratio of the first to the second oligonucleotide probe. Reactions were prepared containing 5 U Nt.BstNBI (NEB), 1 µl of 10×NEB buffer 3.1 (NEB), 0.05 pmol of target nucleic acid (P4), 0.125 pmol of a streptavidin bead-oligonucleotide conjugate (P5) and 25 pmol of Streptavidin bead-oligonucleotide conjugate (P9) in dH$_2$0 to a final reaction volume of 10 µl. Reactions were then incubated for one hour at 55° C. Following incubation, beads were removed using a magnet and subsequently each reaction was analysed by TBE-Urea polyacrylamide gel electrophoresis (PAGE) using a 15% w/v gel stained with SYBR Gold (Life Technologies) and visualised using a UV transilluminator (FIG. 6). For each set of reactions at both probe ratios, a clear visible signal in the presence of the target nucleic acid was observed (FIG. 6; lanes 3 and 5) but in the control reactions without target no reaction was observed (FIG. 6; lanes 2 and 4). These data demonstrate the performance of the method using multiple probes within a single reaction for the detection of a target nucleic acid. The lack of any detectable signal in the absence of target nucleic acid (lanes 2 and 4) indicates that the full length oligonucleotide probes remain in the solid phase and that probe P5 is unable to act as target for the probe P9 unless and until it is cleaved to release a fragment into the aqueous phase. In contrast a signal corresponding to the size of the second probe fragment was observed in the presence of target nucleic acid (lanes 3 and 5). The demonstrated ability to be able to perform the method in a single pot reaction with multiple oligonucleotide probes immobilised on a solid material represents a highly usable and simple embodiment of the method where multiple separate cleavage reactions and separation steps are not required.

Example 1.1

Double Stranded DNA as the Source of Target Nucleic Acid

In this example we demonstrate that the method can be used to detect target nucleic acid derived directly from double-stranded DNA (dsDNA). Three different dsDNA targets were employed: (i) M13mp18 RF I (NEB), which is the double-stranded, covalently closed, circular form of DNA derived from bacteriophage M13, (ii) Lambda DNA, a linear double stranded chromosomal DNA isolated from bacteriophage Lambda; and (iii) a double stranded PCR product of approximately 2 kb amplified from a bacterial genome extract.

Detection of Target Nucleic Acid Derived from Double Stranded DNA Following Treatment with Restriction Endonuclease(s)

Use of one of more restriction endonuclease(s), which may be double-strand cleaving agents and/or nicking agents can be employed to digest double-stranded DNA at defined locations to expose a single-stranded DNA target for a particular nicking agent for use in the method. Through careful selection of restriction enzymes with one or more cleavage site(s) in the proximity of the intended target sequence the double stranded DNA is cleaved into fragments, which following dissociation of the two strands expose a relevant target site.

Figure 7A:
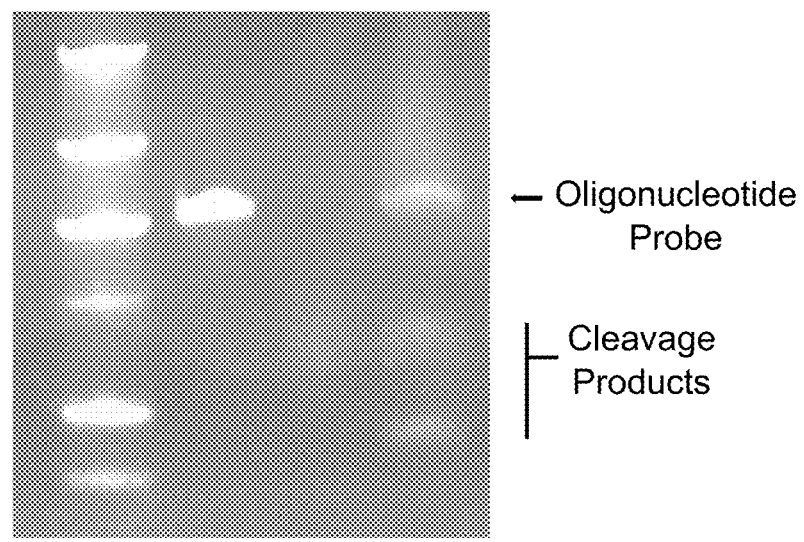
FIG. 7A. Detection of target nucleic acid derived from double stranded DNA following treatment with restriction endonuclease(s) (see Example 1.1).

We prepared a nicking endonuclease cleavage reaction containing 5 pmol of an oligonucleotide probe (P10) comprising a sequence complementary to the target and containing the recognition and cleavage site for the nicking endonuclease Nt.CviPII, in addition to 100 ng of M13mp18 RF I, 2.5 U Nt.CviPII, 1 µlof 10× CutSmart buffer (NEB) and dH$_2$O to a final volume of 10 µl. The reaction was mixed by pipette and incubated at 45° C. for 1 hour. Following incubation, the entire reaction was analysed by TBE-Urea polyacrylamide gel electrophoresis (PAGE) using a 15% w/v gel stained with SYBR Gold (Life Technologies) and visualised using a UV transilluminator. Results are displayed on FIG. 7A. The first lane was loaded with size marker. The second with 5 pmol of the oligonucleotide probe, P10. The third lane was loaded with 100 ng of dsDNA M13mp18 RF I template and the fourth lane with the oligonucleotide probe digestion. Oligonucleotide probe cleavage bands are clearly visible in the fourth lane, indicating efficient detection of a target nucleic acid derived from double stranded DNA.

Figure 7B:
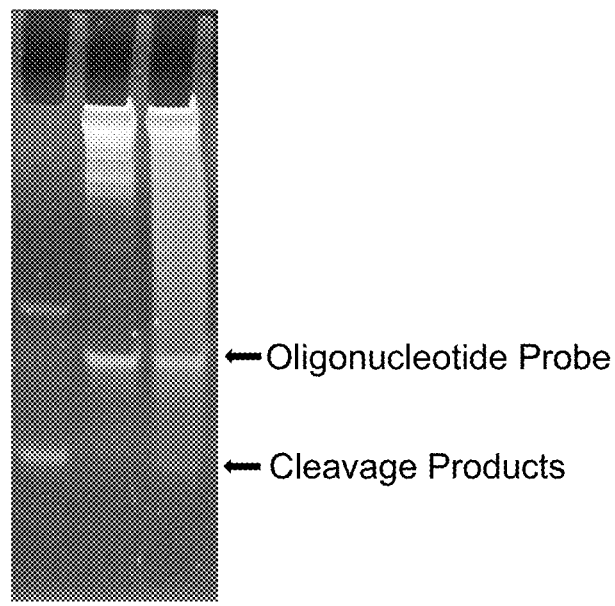
FIG. 7B. Detection of target nucleic acid derived from double stranded DNA following heat denaturation (see Example 1.1).

Detection of Target Nucleic Acid Derived from Double Stranded DNA Following Heat Denaturation In this example we prepared a restriction endonuclease cleavage reaction containing 5 pmol of an oligonucleotide comprising a sequence complementary to a target within the Lambda genome and containing the recognition and cleavage site for the restriction endonuclease BccI, P11, 1 µg of Lambda DNA, 2.5 U BccI, 1 µl of 10× CutSmart buffer (NEB) and dH$_2$O to a final volume of 10 µl The reaction was mixed by pipette and incubated at 37° C. for 1 hour. Lambda DNA was either added untreated or was mixed with the oligonucleotide probe and heated at 95° C. for 10 min in dH$_2$O prior to the digestion reaction. Following incubation, the entire reactions were analysed by TBE-Urea polyacrylamide gel electrophoresis (PAGE) using a 15% w/v gel stained with SYBR Gold (Life Technologies) and visualised using a UV transilluminator. Results are shown in FIG. 7B. The first lane was loaded with a control probe cleavage to demonstrate the size of the oligonucleotide probe and cleavage products. The second lane was loaded with a digestion reaction containing untreated Lambda DNA and the third lane was loaded with a digestion reaction containing Lambda DNA that has been subjected to heat treatment. Cleavage products of the oligonucleotide probe are clearly visible in lane 3 demonstrating that heat denaturation of double stranded DNA may be used to derive target nucleic acid for performance of the method.

Figure 7C:
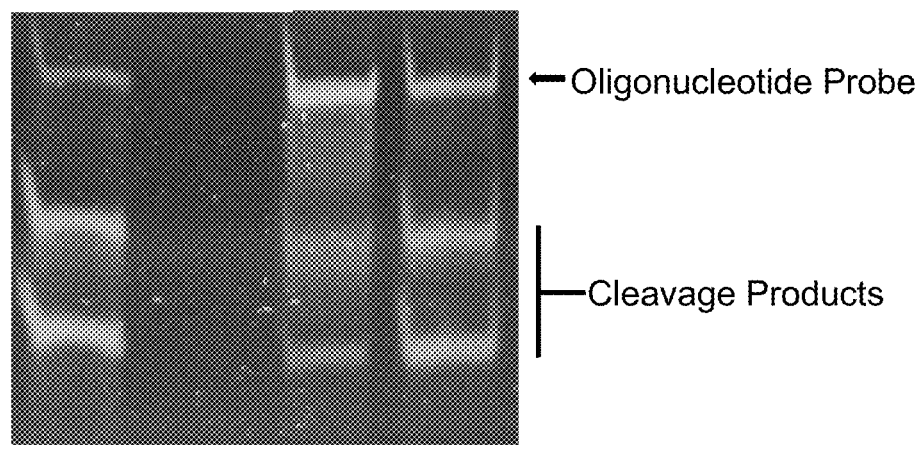
FIG. 7C. Detection of target nucleic acid derived from double stranded DNA by use of exonuclease III (see Example 1.1).

Detection of Target Nucleic Acid Derived from Double Stranded DNA by Use of Exonuclease III We have performed a probe cleavage reaction in the presence of Exonuclease III, an enzyme known to catalyse the sequential removal of mononucleotides from the 3' end of double stranded DNA at a gap or nick site, which therefore exposes single stranded regions of a double stranded DNA, which may contain a target nucleic acid for use in the method. In this example detection of a double stranded PCR product of approximately 2 kb amplified from a bacterial genome extract was performed using an oligonucleotide probe comprising a sequence complementary to the target and containing the recognition and cleavage site for the nicking endonuclease Nt.BstNBI in addition to two phosphorothioate linkages at the 3' end to protect the oligonucleotide from Exonuclease III digestion. A reaction was performed containing 5 pmol of the oligonucleotide probe, 100 ng of purified double stranded DNA target, 1 µl of 10×NEB buffer 3.1 (NEB), 5 U Nt.BstNBI, 100 U of Exonuclease III and dH$_2$O to a final volume of 10 µl. A control reaction was also prepared without addition of Exonuclease III. The reactions were mixed by pipette and incubated at 55° C. for 1 hour. Following incubation, entire reactions were analysed by TBE-Urea polyacrylamide gel electrophoresis (PAGE) using a 15% w/v gel stained with SYBR Gold (Life Technologies) and visualised using a UV transilluminator. The results of this experiment are shown in FIG. 7C. The first lane was loaded with a control probe cleavage to demonstrate the size of the oligonucleotide probe and cleavage products. The second lane was loaded with a digestion reaction performed without Exonuclease III and the third lane was loaded with a digestion reaction wherein Exonuclease III was added. A clear increase in probe cleavage was observed in the reaction containing Exonuclease III demonstrating that Exonuclease III may be used to derive single-stranded target nucleic acid for use in the method of the invention from double-stranded DNA.

This Example 1.1 clearly demonstrates that the target nucleic acid for use in the method of the invention can be derived from double stranded DNA using a variety of approaches, including enzymatic and physicochemical approaches, which can be performed alone or in combination either prior to or during the performance of the method. The oligonucleotide probe cleavage performed in this example may be readily performed wherein the oligonucleotide is the first of a sequential series of oligonucleotides according to the present invention for sensitive detection of target nucleic acids derived directly from double stranded DNA. Strikingly, there was evidence of efficient probe cleavage without the need to heat the sample and denature it. This example demonstrates the versatility of the method to detect target nucleic acids from a variety of different sources.

Example 1.2

Single Stranded RNA as Target Nucleic Acid

In some embodiments of the invention, a single-stranded RNA (ssRNA) molecule may be the target nucleic acid in the performance of the method. Alternatively, ssRNA may be used to produce a complementary DNA sequence which then becomes the target nucleic acid for the performance of the method. Either of these approaches may be employed in certain embodiments of the method, such as the detection of organisms (e.g. viruses) which contain an RNA genome or the detection of transcribed genes from any organism.

Direct Detection of Single Stranded RNA

Figure 8A:
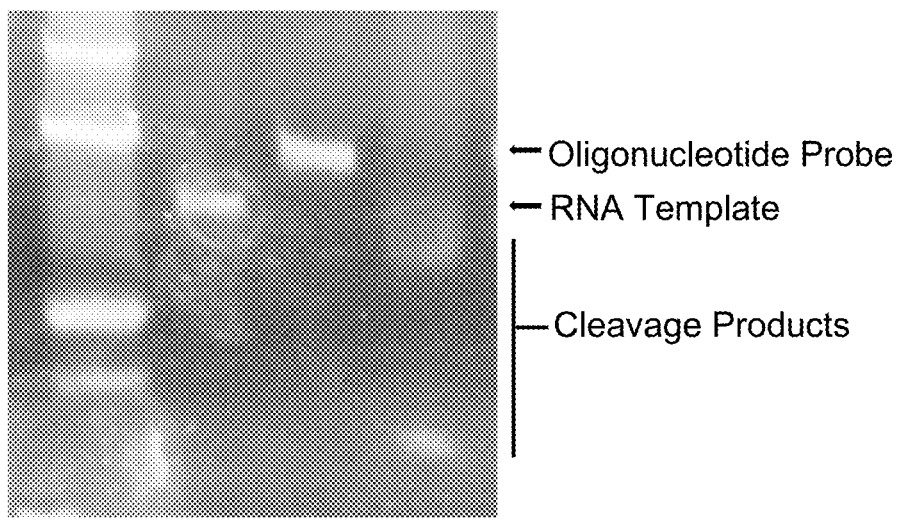
FIG. 8A and FIG. 8B. Single stranded RNA as target nucleic acid (see Example 1.2).

In order to demonstrate that probe cleavage reactions can occur using single stranded RNA as template, we performed oligonucleotide probe cleavage reactions with ssRNA as a target nucleic acid. Firstly, an oligonucleotide probe was designed to contain the recognition sequence and cleavage site for the nicking endonuclease Nt.CviPII. A complementary short RNA was also synthesised by the manufacturer (Eurofins Genomics). A reaction was then prepared containing 5 pmol of RNA oligonucleotide target, 5 pmol oligonucleotide probe, 2.5 U of Nt.CviPII, 1 µl of 10× CutSmart buffer (NEB) and dH$_2$O to a final reaction volume of 10 µl. The reaction was mixed by pipette and incubated at 45° C. for 1 hr. Following incubation, the entire reaction was analysed by TBE-Urea polyacrylamide gel electrophoresis (PAGE) using a 15% w/v gel stained with SYBR Gold (Life Technologies) and visualised using a UV transilluminator. Results are displayed in FIG. 8A. The first lane was loaded with a size marker. The second lane with the RNA template, the third lane with the oligonucleotide probe and the fourth with the digestion reaction. Efficient oligonucleotide probe cleavage was demonstrated in the oligonucleotide probe digestion reaction.

Figure 8B:
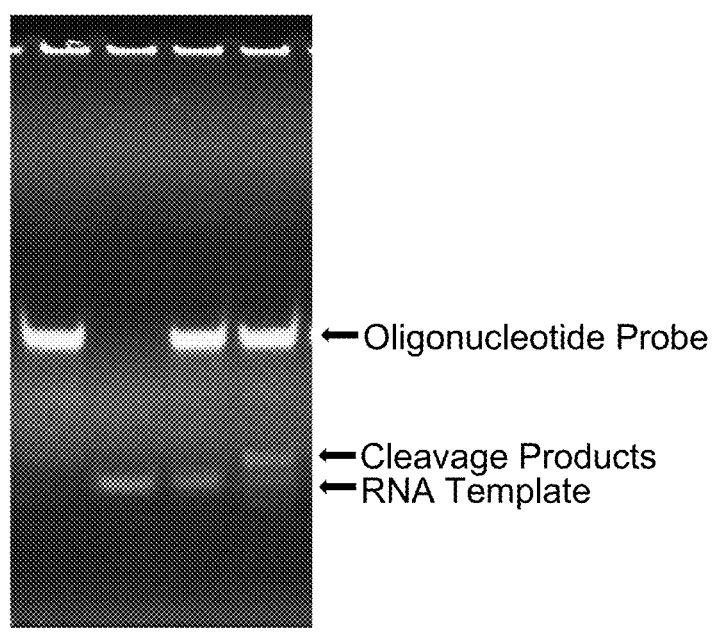

Secondly, an oligonucleotide probe was designed to contain the recognition sequence and cleavage site for the restriction endonuclease AvaII. A complementary RNA was also synthesised and employed as target nucleic acid. A reaction was then prepared containing 5 pmol of the RNA oligonucleotide target, 5 pmol oligonucleotide probe, 2.5 U of AvaII, 1 µl of 10× CutSmart buffer (NEB) and dH$_2$O to a final reaction volume of 10 µl. The reactions were mixed by pipette and incubated at 37° C. for 1 hr. Following incubation, the entire reaction was analysed by TBE-Urea polyacrylamide gel electrophoresis (PAGE) using a 15% w/v gel stained with SYBR Gold (Life Technologies) and visualised using a UV transilluminator. Results are displayed in FIG. 8B. The first lane was loaded with the oligonucleotide probe, the second with the RNA target, the third lane with both the oligonucleotide probe and the RNA target and the fourth lane with the digestion reaction. Efficient oligonucleotide probe cleavage was demonstrated in the oligonucleotide probe digestion reaction.

Figure 8C:
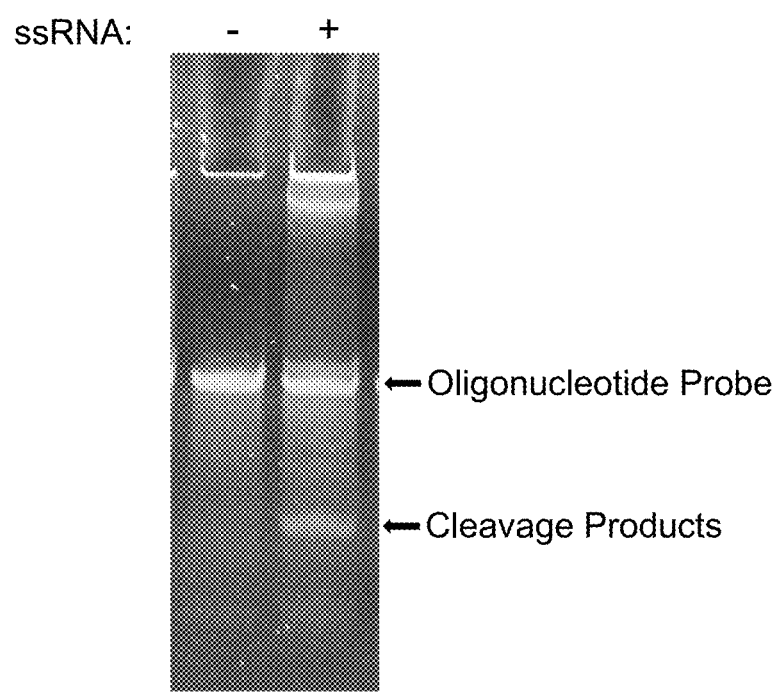
FIG. 8C. Detection of target nucleic acid generated from single stranded RNA by the action of reverse transcriptase.

The above experiments demonstrate that direct detection of a ssRNA target nucleic acid is possible and can be used in the performance of the method. The efficient oligonucleotide probe cleavage observed, evidences the ability to perform the method with ssRNA as target nucleic acid with different restriction enzymes, including nicking agents and double-strand cleaving agents. The oligonucleotide probe cleavage reactions performed in these experiments may be readily extended by designing the oligonucleotide probe to be the first of a sequential series of oligonucleotides according to the present invention for sensitive detection of ssRNA target nucleic acids. Crucially, we have demonstrated that a DNA/RNA hybrid duplex forms and can be readily cleaved by nicking agents. This evidences that the method can be used directly for detection of ssRNA targets without a requirement to generate DNA using a reverse transcriptase Detection of Target Nucleic Acid Generated from Single Stranded RNA by the Action of Reverse Transcriptase In this example we demonstrate that reverse transcriptase can be employed to generate target nucleic acid for use in the method. Furthermore, the reverse transcription reaction can be performed simultaneously with the oligonucleotide probe cleavage of the method. Firstly, a ~1,600 nucleotide single-stranded RNA was prepared from synthetic DNA by in vitro transcription using the TranscriptAid T7 High Yield Transcription Kit (Life Technologies). An oligonucleotide probe was designed with the same sequence as a 16 nucleotide region of this ssRNA containing the recognition sequence and cleavage site for a double-strand cleaving restriction endonuclease. A reaction was prepared containing 0.75 ng of the ssRNA, 5 pmol of oligonucleotide probe, 5 pmol of a reverse transcriptase primer complementary to a 14 nucleotide region within the ssRNA, 2.5 U of Ban I, 2.5 U of MMuLV reverse transcriptase, 500 nM of dNTP (final concentration), 1 µl of 10×AMV buffer (NEB) and dH$_2$O to a final reaction volume of 10 µl. The reaction was mixed by pipette and incubated at 45° C. for 1 hour. Following incubation, the entire reaction was analysed by TBE-Urea polyacrylamide gel electrophoresis (PAGE) using a 15% w/v gel stained with SYBR Gold (Life Technologies) and visualised using a UV transilluminator. The results are shown in FIG. 8C. The first lane displays a control reaction wherein the ssRNA was omitted, whilst the second lane contains the complete reaction. Cleavage products of the oligonucleotide probe are visible only in the presence of the target RNA molecule, demonstrating that DNA target derived from ssRNA can be employed as a target for use in the method. By employing reverse transcriptase either prior to or simultaneously with the oligonucleotide probe cleavage reaction(s) of the method, DNA target nucleic acid can be readily generated from ssRNA for detection using the method.

Example 2

Detection of Target Nucleic Acids Using Colorimetric Signal to Detect Probe Fragments A number of embodiments of the invention encompass colorimetric methods for detection of probe fragments to indicate the presence of target nucleic acid. To achieve this, one approach is to conjugate a probe with gold nanoparticles. The gold-conjugated oligonucleotide probes can then also be attached through another moiety to a solid support. During the performance of the method, as gold conjugated probe is cleaved in the presence of target nucleic acid, the gold nanoparticles are released from the solid into the aqueous phase and an associated colorimetric signal can consequently be detected and easily quantified, either at single time-points or in real-time. Alternatively, carbon can be employed instead of gold for colorimetric signal detection. Rather than direct attachment of a colorimetric dye to one or more of the oligonucleotide probes during the performance of the method, a moiety that is capable of attachment to a colorimetric dye, e.g. biotin, can be attached and probe fragments may then be subsequently detected following attachment of the relevant colorimetric dye to that moiety.

Colorimetric Detection with One Oligonucleotide Probe Attached to a Solid Material (Streptavidin Magnetic Beads) and to a Colorimetric Dye (Gold Nanoparticles)

We performed an experiment in order to demonstrate the accumulation of colorimetric signal during the performance of the method with an oligonucleotide probe conjugated to gold nanoparticles. In order to do this, an oligonucleotide probe, P12, containing a 3' thiol modification and a 5' biotin moiety was first reduced using TCEP, as described in the general methods section. The oligonucleotide was then conjugated to maleimide activated 40 nm diameter gold nanoparticles (Innova Biosciences) by reacting 2 mg of gold nanoparticles with 1.6 nmol of thiol activated oligonucleotide in 45 µl of reaction buffer for ninety minutes at room temperature, according to the manufacturer's instructions. The reaction was then quenched by the addition of the quenching reagent provided and subsequently incubated for twenty minutes at room temperature with gentle agitation. Next, the conjugate gold solution was centrifuged at 7,500×g for five minutes. Supernatant was removed from the conjugated nanoparticles, which were subsequently re-suspended in 200 µl of 1×BW buffer, vortexed for ten seconds and centrifuged at 7,500×g for five minutes. This wash procedure was repeated a total of three times at which point the gold was re-suspended in 50 µl of BW buffer.

Figure 9A:
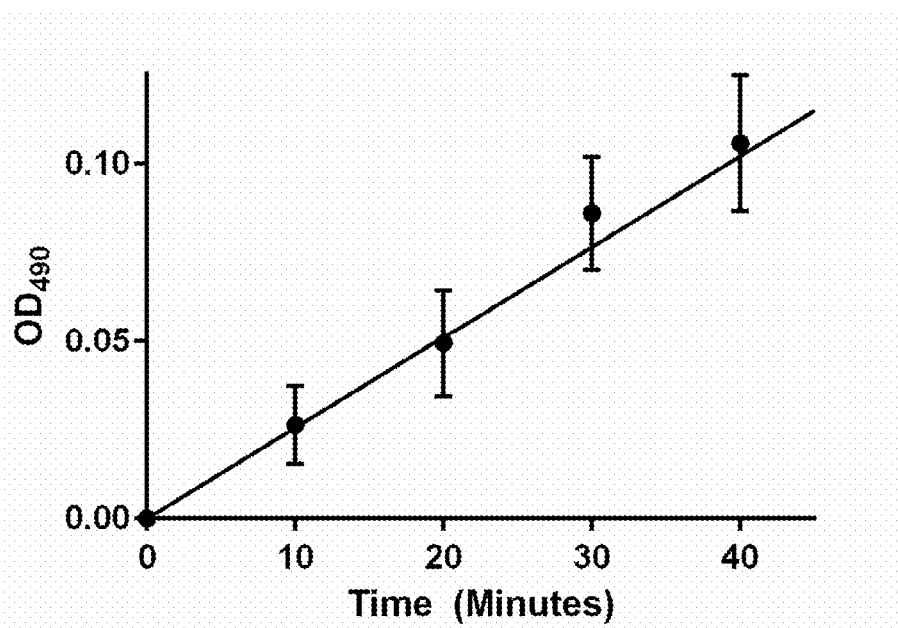
FIG. 9A. One oligonucleotide probe attached to a solid material (streptavidin magnetic beads) and to a colorimetric moiety (gold nanoparticles) (see Example 2).
Figure 12A:
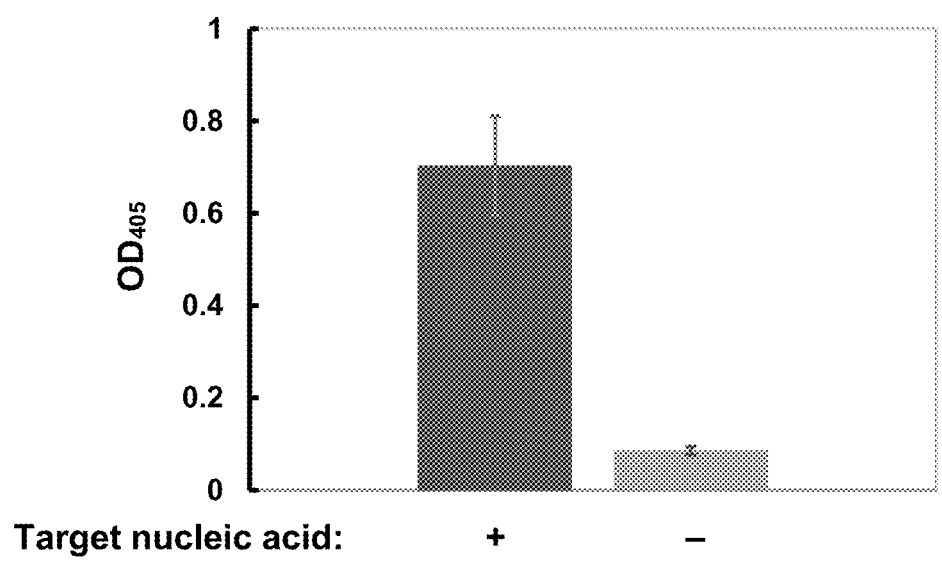
FIG. 12A. Colorimetric detection using enzyme attached oligonucleotide probe (see Example 2.1).
Figure 12B:
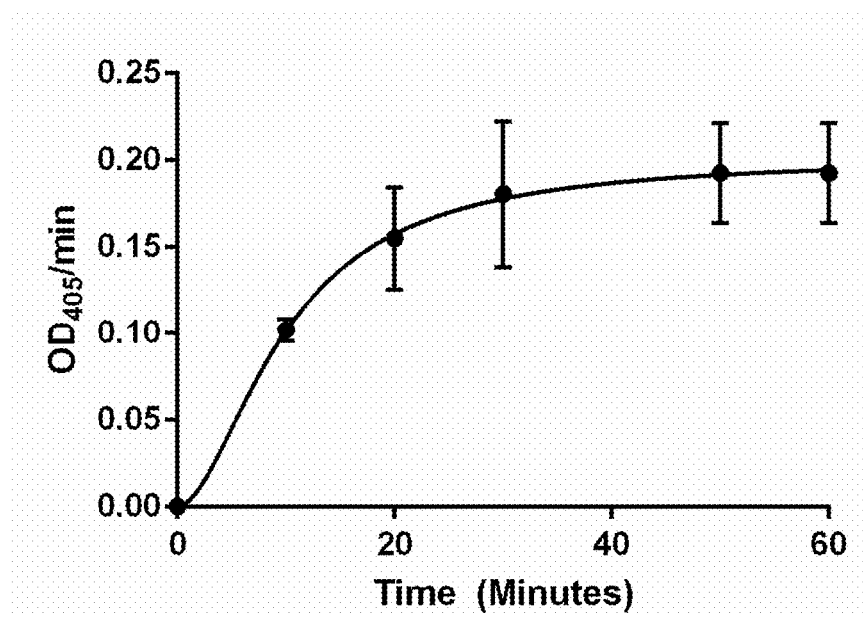
FIG. 12B. Time course of colorimetric detection using enzyme attached oligonucleotide probe (see Example 2.1).

In order to couple the oligonucleotide to a solid material and consequently remove the nanoparticles from the aqueous solution, 30 µl of the conjugate containing approximately 4×10$^{14}$ nanoparticles, was incubated with 1.8 mg of Dynabeads (C1, streptavidin magnetic beads, Life Technologies) in a final volume of 300 µl of BW buffer at room temperature for ten minutes with gentle agitation. Conjugated beads were then transferred to 1× buffer 3.1 (NEB). Triplicate oligonucleotide probe cleavage reactions were prepared containing 0.6 mg of conjugated beads, 50 U Nt.BstNBI (NEB), 10 µl 10× buffer 3.1 (NEB), 0.125 pmol of target nucleic acid (P3) and dH$_2$O to a final reaction volume of 100 µl. Oligonucleotide probe cleavage reactions were incubated at 55° C. for 50 minutes. During the incubation reaction, absorbance readings at 490 nm were measured at ten minute intervals over the course of the reaction, following removal of beads from the reaction using a magnet. The results (displayed in FIG. 9A, demonstrate a linear progression of colorimetric signal during the course of the oligonucleotide probe cleavage reaction ($R^2$=0.9851). Importantly, this evidences the ability to generate a visible colorimetric signal for detection of probe fragments produced in the performance of the method. Notably, the linear accumulation of signal observed is consistent with the kinetics of a first order reaction predicted and noticeably different to the exponential signal observed in the performance of the method with multiple oligonucleotide probes (FIG. 2) or use of a single probe conjugated to an enzyme (FIG. 12B).

Colorimetric Detection with Two Oligonucleotide Probes in a Single-Pot Reaction with Both Probes Attached to a Solid Material (Streptavidin Magnetic Beads) and the Second Probe Also Attached to a Colorimetric Dye (Gold Nanoparticles)

In this example an embodiment of the method using two oligonucleotide probes with one coupled to a colorimetric dye was performed in a single-pot reaction. Gold nanoparticle conjugated to an oligonucleotide probe (P12) as described previously. In order to couple the oligonucleotide to a solid material and consequently remove the nanoparticles from the aqueous solution, 30 µl of the conjugate was incubated with 1.8 mg of Dynabeads (C1, streptavidin magnetic beads, Life Technologies) in a final volume of 300 µl of BW buffer at room temperature for ten minutes with gentle agitation. Conjugated beads were then transferred to 1× buffer 3.1 (NEB). A 5' amine modified oligonucleotide probe, P3, was conjugated to maleimide beads as described in the general methods section. Next two probe, one pot reactions, were assembled with the gold conjugated oligonucleotide probe in large excess in order to be able to readily detect a colorimetric signal. Reactions were assembled each containing; 0.6 mg of P12 beads, a quantity of the P3 beads corresponding to 0.25 pmol of total oligonucleotide, 50 U Nt.BstNBI (NEB), 10 µl 10× buffer 3.1 (NEB), 0.125 pmol or 0 pmol of target nucleic acid (P1) and dH$_2$O to a final reaction volume of 100 µl.

Figure 9B:
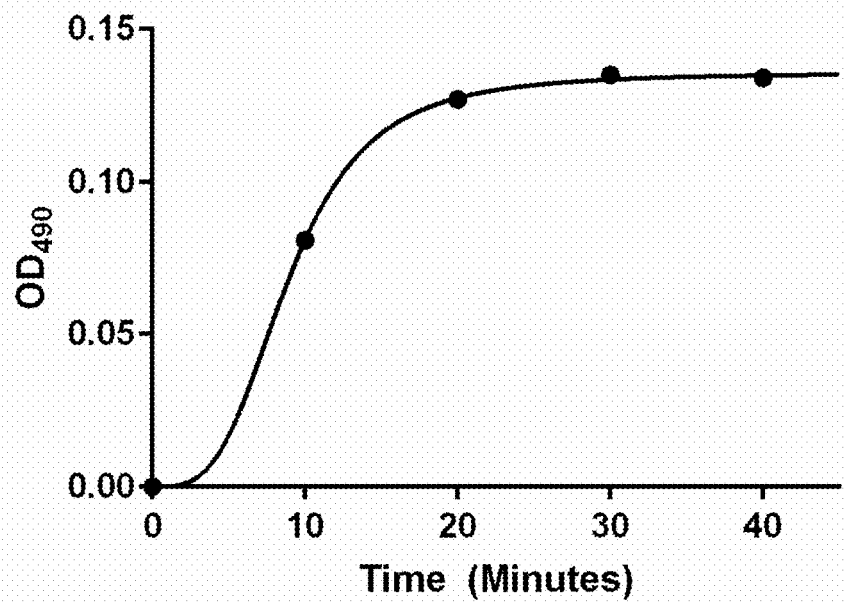
FIG. 9B. Two oligonucleotide probes in a single-pot reaction with both probes attached to a solid material (streptavidin magnetic beads) and the second probe also attached to a colorimetric moiety (gold nanoparticles) (see Example 2).

Oligonucleotide probe cleavage reactions were incubated at 55° C. for fifty minutes. During the incubation reaction, absorbance readings at 490 nm were measured at ten minute intervals over the course of the reaction, following removal of beads from the reaction using a magnet. The results displayed in FIG. 9B, demonstrate an exponential accumulation of colorimetric signal during the initial course of the oligonucleotide probe cleavage reaction. A sigmoidal curve fit model was used to fit the data ($R^2$=0.9998). Importantly, this exponential signal generation in the early stages of the reaction is consistent with the kinetics of a second order reaction predicted in the performance of the method with two oligonucleotide probes (FIG. 2) and allows more rapid determination of the presence of target nucleic acid than observed with a single oligonucleotide probe.

Example 2.1

Detection of Target Nucleic Acids using Oligonucleotide Probe Attached to an Enzyme to Produce Colorimetric Signal Certain embodiments of the invention comprise a method for simple detection of probe fragments by attaching an oligonucleotide probe to an enzyme capable of generating a colorimetric signal when contacted with a substrate. Following cleavage of the oligonucleotide probe, the enzyme-attached probe fragment produced can be readily detected and quantified by detecting the colorimetric signal produced when it is contacted with an appropriate substrate. The signal can be quantified either at a defined end point or during a timecourse. In this example, we have demonstrated attachment of oligonucleotide probes to enzymes capable of generating a colorimetric signal.

Covalent Attachment of Oligonucleotide Probe to Maleimide Activated Horseradish Peroxidase (HRP)

Figure 10A:
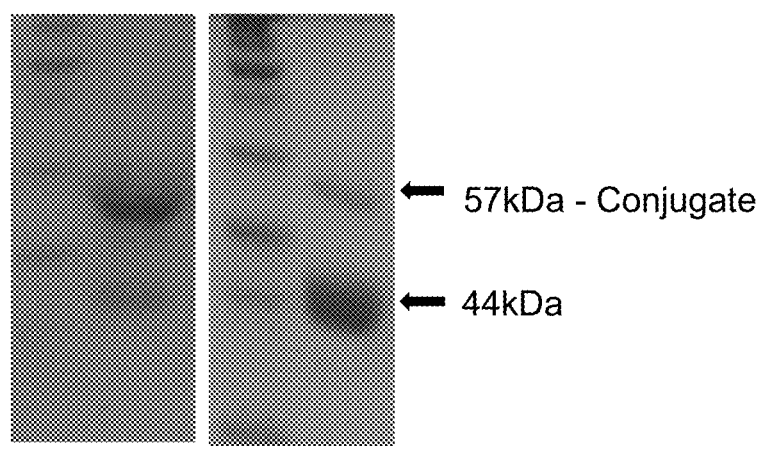
FIG. 10A. Covalent attachment of oligonucleotide probe to horseradish peroxidase (see Example 2.1).

Oligonucleotide probe P13 was synthesised with a C18 spacer and biotin TEG modification on the 5' end and sulfhydryl modification on the 3'. In order to reduce disulphide bonds between oligonucleotides, 2 nmol oligonucleotide was incubated for forty minutes at room temperature with shaking in 10 µl of 1×PBS (pH 7.2) containing 10 mM TCEP and 2 mM EDTA. The oligonucleotide was then desalted using a 7 kDa MWCO desalting column (Zeba Spin Desalting Column, Life Technologies) equilibrated with 1×PBS (pH 7.2)+1 mM EDTA. A conjugation reaction was then prepared containing desalted oligonucleotide probe at a concentration of 100 pmol/µl and maleimide-activated HRP (Sigma Aldrich) at a concentration of 0.25 pmol/µl in 1×PBS (pH 7.2)+1 mM EDTA. The reaction was incubated at room temperature for two hours with shaking. Approx. 2 µg of conjugated protein was analysed by a 10% (w/v) SDS polyacrylamide gel electrophoresis gel in order to determine conjugation efficiency. The gel, displayed in FIG. 10A (Left panel), demonstrated efficient production of HRP conjugated oligonucleotide probe. Such a reagent may be used in the method for colorimetric detection of probe fragments following cleavage.

Covalent Attachment of Oligonucleotide Probe to Horseradish Peroxidase (HRP) with a Polyethylene Glycol (PEG) Spacer In order to introduce an additional spacer between the oligonucleotide and the HRP to overcome any potential steric hindrance of the nicking endonuclease cleavage of the HRP conjugated probe we have performed conjugation reactions using a linker comprising a polyethylene glycol (PEG) spacer. Pierce HRP (Life Technologies) was attached to an amine-to-sulfhydryl crosslinking reagent, SM(PEG)12 (Life Technologies). A reaction was prepared containing HRP at 1.5 mg/ml and SM(PEG)12 at 3.75 mM (diluted from a 250 mM stock in DMSO) in 1×PBS (pH 7.2)+2 mM EDTA and incubated at room temperature for one hour with shaking. In order to remove unreacted SM(PEG)12, the reaction was then passed through two desalting columns (Zeba Spin Desalting Columns, 7 KDa MWCO, Life Technologies) equilibrated with 1×PBS (pH 7.2)+1 mM EDTA. A conjugation reaction was then prepared containing the recovered HRP at 0.8 mg/ml reacted with a 5' C18 spacer and biotin TEG modified and a 3' sulfhydryl modified oligonucleotide (P13) following TCEP treatment (as previously described) at 100 pmol/µl in 1×PBS (pH 7.2)+1 mM EDTA. The reaction was incubated at room temperature for two hours with shaking. Approx. 2 µg of conjugated protein was analysed by a 10% (w/v) SDS polyacrylamide gel electrophoresis gel in order to determine conjugation efficiency. The gel, displayed in FIG. 10A (Right panel), demonstrated production of HRP conjugated to oligonucleotide probe with a PEG spacer. Bands were observed at the expected size of the conjugated enzyme (57 kDa) and not at the size of the unconjugated enzyme (44 kDa). Such a reagent may be used in the method for colorimetric detection of probe fragments following cleavage.

Purification of Horseradish Peroxidase Attached Oligonucleotide Probe

In order to remove unconjugated oligonucleotide and HRP from the conjugation reactions described we have developed a hybridisation based process of affinity enrichment.

Figure 10B:
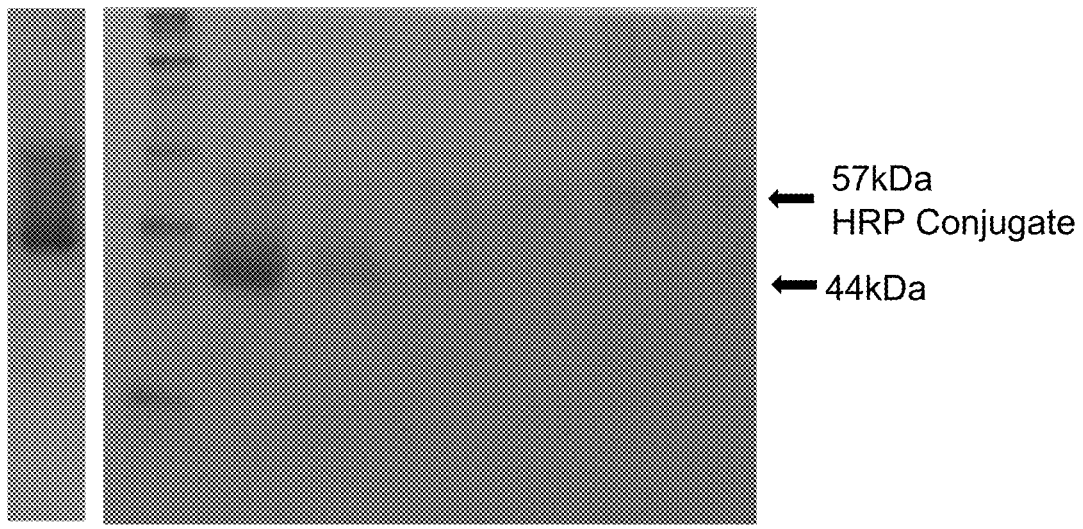
FIG. 10B. Purification of horseradish peroxidase attached oligonucleotide probe (see Example 2.1).

First, polyethylenimine (PEI) precipitation is performed to remove unconjugated oligonucleotide probe, as described in the general methods. In order to perform affinity enrichment a 3' biotin TEG modified oligonucleotide probe, P2, designed to contain a region of complementarity to the 5' biotin and 3' sulfhydryl modified oligonucleotide probe, P13 conjugated to the enzyme, was coupled to streptavidin beads using the standard coupling protocol (general methods). The HRP conjugate sample recovered from the PEI precipitation (~0.125 mg/ml total protein) was incubated with 1 mg of the streptavidin coupled beads in a volume of 40 ul in 1×PBS (pH 7.0) for 10 minutes at room temperature followed by 20 minutes at 4° C. The beads were removed by centrifugation and magnet pull-down on ice and the supernatant was removed and stored. Beads were resuspended in 40 µl phosphate buffer (pH 7.0) and agitated using a vortex mixer at 4° C. for 10 minutes. This 'wash' process was repeated once more at 4° C. and then twice at 40° C. Between each wash, beads were removed by centrifugation and magnet pull-down as described. The final elution step was performed at 55° C. for 10 minutes. 35 µl of each recovered wash was concentrated by evaporation and analysed by SDS PAGE (10% w/v gel). The gel, displayed in FIG. 10B, demonstrates purification of HRP-oligonucleotide conjugate from unconjugated HRP, as in the right hand lane only a band corresponded to the size of the conjugate is visible and the band for unconjugated HRP is not visible. This method evidences purification of enzyme conjugated oligonucleotide, which is an important requirement to ensure that reagents of sufficient purity for use in detection of target nucleic acids can be prepared.

Covalent Attachment of Oligonucleotide Probe to β-Galactanase

Figure 11:
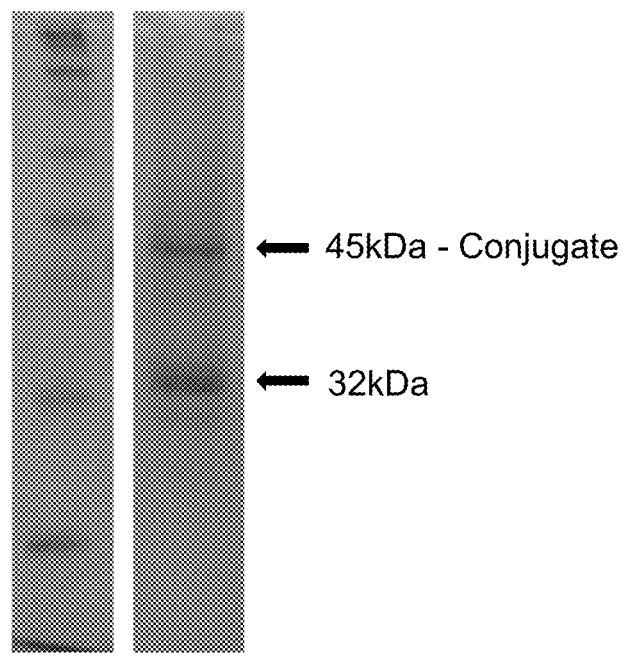
FIG. 11. Covalent attachment of oligonucleotide probe to β-Galactanase (see Example 2.1).

Additional alternative enzymes can also be conjugated to oligonucleotide probes for use in the method. For example, one of a number of glycosyl hydrolases may be used in order to perform the detection using colorimetric substrates, such as β-Galactanase which is active with both soluble and insoluble colorimetric substrates (e.g. AZCL-Galactan).

β-Galactanase (Prozomix) was prepared at 0.8 mg/ml with 1 mg/ml Sulfo-SMCC (Sigma Aldrich) in 1×PBS (pH 7.0). The reaction was incubated at room temperature for one hour with agitation. An oligonucleotide probe with a 5' C18 spacer and a biotin TEG modification, and with a 3' sulfhydryl modification (P13) was subjected to TCEP treatment, as described in Example 2.1 and added to the activated enzyme to yield a solution with a final concentration of 0.4 mg/ml β-Galactanase and 100 pmol/µl oligonucleotide probe. The conjugation mixture was further incubated at room temperature for two hours with agitation. The reaction was then analysed by SDS PAGE (10% w/v gel), which is displayed in FIG. 11. This result (right hand panel) demonstrates the presence of a band corresponding to the size of conjugated enzyme, evidencing that a selection of enzymes is available for conjugation to oligonucleotide probes for use in colorimetric detection of target nucleic acids.

Attachment of Enzyme-Conjugated Oligonucleotide Probes to a Solid Material

Dual conjugated oligonucleotides attached to an enzyme at one end and attached to a solid material at the other end have been prepared. Firstly, oligonucleotide conjugated to HRP or another enzyme such as β-Galactanase, prepared as described above, was attached to streptavidin beads by manufacturing the relevant oligonucleotide with a biotin (or biotin-TEG) group present on the opposite end of the oligonucleotide to the functional group used for enzyme attachment. Enzyme conjugated oligonucleotide probe was attached to streptavidin magnetic beads as described in the general methods section. Secondly, we prepared oligonucleotide conjugated maleimide beads, as described in the general methods section, and thereafter conjugated them to excess Pierce Streptavidin HRP (Life Technologies) in BW Buffer (pH 7.4) with incubation at room temperature for 45 minutes. Beads attached to oligonucleotide HRP prepared with the latter method were washed six times in 1 ml of 1×PBS (pH 7.4) for one minute with shaking. Immediately prior to use in a cleavage reaction, the beads were washed a further 5 times in this manner and once in 100 µl of relevant buffer for 1 minute with shaking, before resuspension in the relevant reaction buffer.

Colorimetric Detection Using Enzyme-Attached Oligonucleotide Probe

In order to exemplify the quantitative colorimetric detection of target nucleic acid using oligonucleotide probe attached to enzyme we prepared a batch of dual conjugated oligonucleotide probe (P12). Firstly, probe was conjugated via a thiol group to maleimide beads as described in the general methods section before conjugation to Streptavidin HRP as described above. Cleavage reactions were prepared containing an amount of beads corresponding to approximately 7.5 pmol oligonucleotide, 5 U Nt.BstNBI, 1 µl 10× Buffer 3.1 (NEB), 0.05 pmol oligonucleotide target nucleic acid and dH$_2$O to a total volume of 10 µl. Reactions were incubated at 55° C. for sixty minutes. Samples were taken at ten minute time intervals with prompt removal of beads by centrifugation and magnet pull-down. 6 µl of supernatant was then added to 94 µl of Pyrogallol reaction mix (5 mg/ml Pyrogallol (Sigma Aldrich) and 0.0025% (v/v) H$_2$O$_2$ in phosphate buffer (pH 6.0). Absorbance readings at 405 nm were then measured at 10 second intervals over the course of a 5 minute reaction using an absorbance spectrophotometer. Multiple repeat experiments were performed in the presence of target nucleic acid at each of the time points, and for the final time point multiple repeats were also performed in the absence of target nucleic acid, as displayed on FIG. 12A. The absorbance readings in the presence and absence of target nucleic acid during a sixty minute cleavage reaction and subsequent five minute HRP pyrogallol reaction are displayed in FIG. 12B. This example demonstrates that the presence of target nucleic acid can be determined using oligonucleotide probes attached to enzymes that give a colorimetric signal in the presence of a substrate. The colorimetric signal resulting from conjugated oligonucleotide accumulates exponentially even without a sequential series of oligonucleotide probes, i.e. with use of a single oligonucleotide probe.

Example 2.2

Detection of Target Nucleic Acids Using Nucleic Acid Lateral Flow

Oligonucleotide probe fragments resulting from performance of the method may be readily detected by colorimetric signal using nucleic acid lateral flow wherein they are separated from other reaction components using a membrane, typically made of nitrocellulose. This example demonstrates a number of alternative approaches to detection of the probe fragments in the method by colorimetric signal detection using lateral flow.

Colorimetric Detection by Nucleic Acid Lateral Flow with Gold Nanoparticles

Figure 13A:
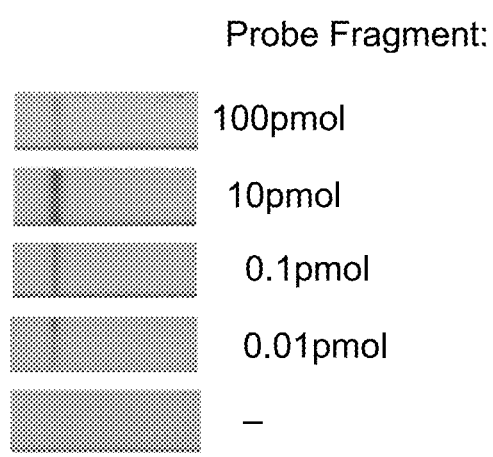
FIG. 13A. Colorimetric detection by nucleic acid lateral flow with gold nanoparticles (see Example 2.2).

In order to demonstrate one approach for integration of the method with colorimetric lateral flow read-out, we have prepared gold nanoparticles conjugated to an oligonucleotide probe. 20 nm gold nanoparticles (BioAssay Works) were conjugated to oligonucleotide probe P14 with a thiol modification on the 5' end, using sodium chloride salt-aging. After washing into PBS containing 0.01% (w/v) TWEEN® 20 (polyoxyethylenesorbitan monolaurate), the gold nanoparticles were pipetted onto the conjugate pad of gRAD lateral flow strips (BioPorto) and air-dried. Various quantities of complementary oligonucleotide, P15, synthesised with biotin on the 5' end, were applied to the lateral flow strips in the manufacturer's recommended running buffer and results were recorded by photography following signal development. Results are displayed in FIG. 13A. A clear visible band appeared on the lateral flow strips only in the presence of the oligonucleotide P15, which hybridises to the P14-conjugated gold nanoparticles deposited on the conjugate pad and flows along the strip before localising at the biotin-binding protein band printed on the nitrocellulose. This example clearly demonstrates one approach to using colorimetric lateral flow for the detection of probe fragments produced in the method. Oligonucleotide P15 represents a biotinylated probe fragment that would be generated during the performance of the method and can be rapidly detected by colorimetric signal at low concentration.

Colorimetric Detection by Nucleic Acid Lateral Flow with Carbon Nanoparticles

Figure 13B:
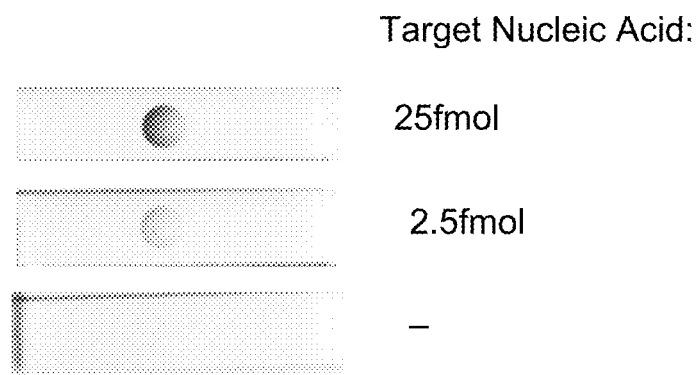
FIG. 13B. Colorimetric detection by nucleic acid lateral flow with carbon nanoparticles (see Example 2.2).

In order to demonstrate another approach for integration of the method with a colorimetric lateral flow read-out, we used carbon lateral flow strips prepared as described in the general methods section for sensitive colorimetric detection of probe fragments. An oligonucleotide probe containing the recognition sequence and cleavage site for a double-strand cleaving restriction endonuclease and synthesised with a biotin group on the 5' end was covalently attached to beads following standard protocols. 50 µg beads were incubated at 37° C. for 10 min in a 10 µl reaction containing 20 U of the relevant restriction enzyme, 1 µl of 10× reaction buffer and various concentrations of an oligonucleotide representing the probe fragment that would be produced from the preceding oligonucleotide probe in the method. Following incubation, 60 µl running buffer was added and each reaction was analysed by applying the entire contents of the reaction onto the sample pad of a lateral flow strip. The nitrocellulose membrane of the lateral flow strip was printed with an oligonucleotide containing the reverse complement to the probe fragment released from the bead following cleavage. A photograph of the nitrocellulose membrane following development of the lateral flow strips is displayed in FIG. 13B. Colorimetric signal was only observed in the presence of target nucleic acid and with increasing intensity as the level of target nucleic acid increases. This example demonstrates that carbon-based colorimetric nucleic acid lateral flow detection can be readily integrated for detection of the probe fragments produced in the method, in a simple, low-cost, rapid and sensitive assay format with no requirement for downstream extraction and processing of the reaction.

Example 3

Investigation of Reaction Parameters

We have explored a number of parameters of an oligonucleotide probe cleavage reaction. Whilst the reactions were not performed in the context of a sequential series of oligonucleotide probes, the observations are directly applicable to the present invention.

Oligonucleotide Probe Cleavage in the Presence of Excess Nucleic Acid Material

Figure 14A:
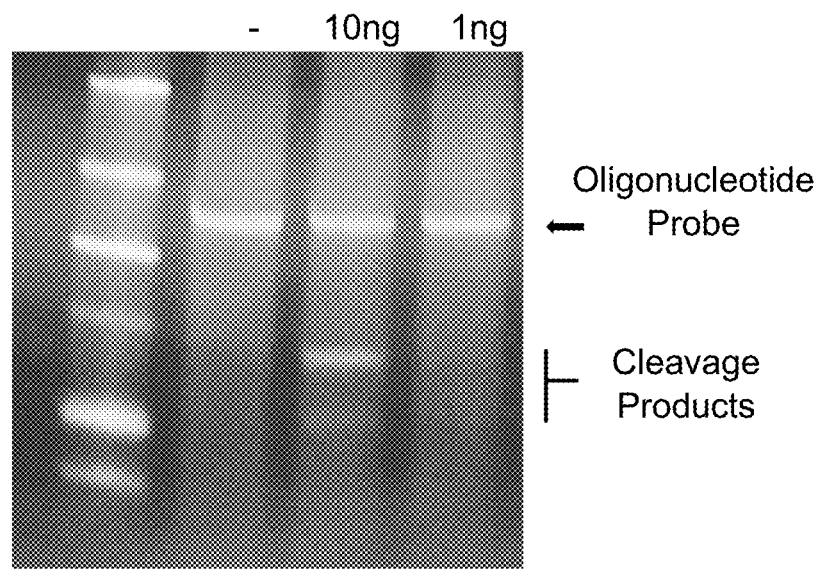
FIG. 14A. Oligonucleotide probe cleavage in the presence of excess nucleic acid material (see Example 3).

A number of intended applications for the invention require the detection of a target nucleic acid sequence within a sample which is or may be contaminated with an excess of other nucleic acid(s). For example, large excesses of DNA or RNA may be present within the sample from organisms other than the intended target organism. In order to test whether such non-specific nucleic acid might lead to complications in probe cleavage reactions (e.g. interference of the intended oligonucleotide probe cleavage or aberrant probe cleavage), we performed a number of probe cleavage reactions in the presence of a large excess of herring sperm DNA. Reactions were prepared containing 200 ng Herring sperm DNA (Sigma Aldrich), 5 U Nt.BstNBI, 1 µl of 10× Buffer 3.1 (NEB), 5 pmol oligonucleotide probe (P16), M13mp18 single-stranded DNA template at various levels as indicated and dH$_2$O to a total volume of 10 µl. Reactions were incubated at 55° C. for one hour and analysed by TBE-Urea polyacrylamide gel electrophoresis (15% w/v gel). Results are displayed in FIG. 14A. No visible probe cleavage was observed in the absence of template (lane 2), even in the presence of high levels of Herring Sperm DNA. Moreover, oligonucleotide probe cleavage was unaffected and cleavage products were apparent in both samples containing both 10 ng (lane 3) and 1ng (lane 4) of the target nucleic acid. This example evidences the high specificity of the method.

Figure 14B:
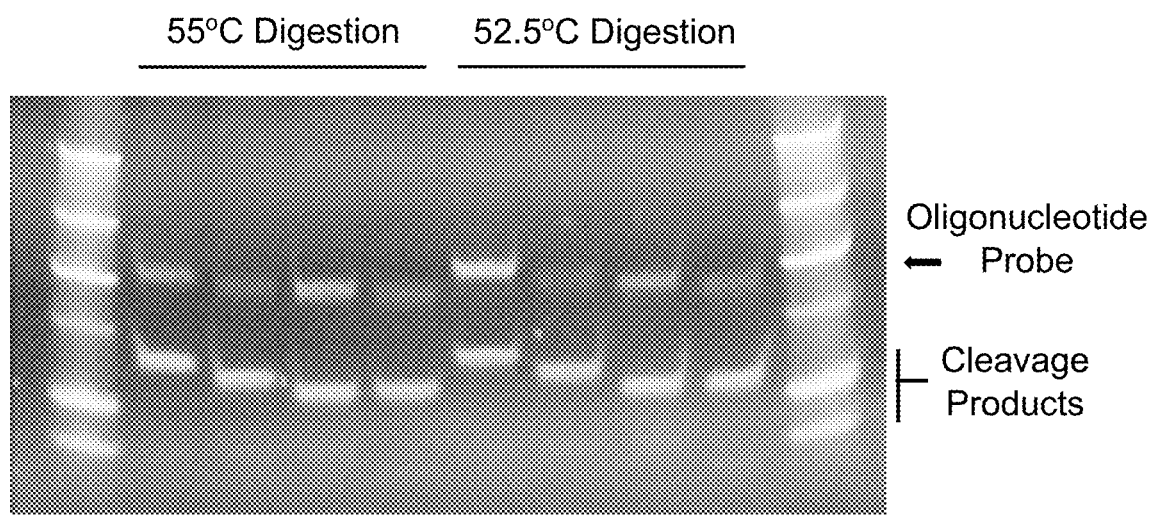
FIG. 14B. Investigation of length of complementarity region on oligonucleotide probe cleavage (see Example 3).

Investigation of Length of Complementarity Region on Oligonucleotide Probe Cleavage In order to investigate how oligonucleotide probe length may influence the method, we performed a number of probe cleavage reactions with variants of the same probe of different length. A number of probes containing a region complimentary to an Nt.BstNBI recognition site in the M13mp18 genome were designed. Whilst these probes shared high homology they varied in total length, namely by shortened sequence complimentary to the M13 target site. Cleavage reactions were prepared containing 5 pmol oligonucleotide probe (P17, P18, P19 or P20), 5 U Nt.BstNBI (NEB), 1 µl 10× Buffer 3.1 (NEB), 100 ng of M13mp18 DNA and dH20 to a total volume of 10 µl. Duplicate sets of the reactions were incubated at either 55° C. or 52.5° C. for 1 hour and the entirety of each sample was analysed by TBE-Urea PAGE (15% w/v gel), FIG. 14B. Efficient cleavage of oligonucleotide probes was observed across the range of probe lengths tested. The example suggests the present invention is versatile regarding the length of complementarity regions used within the oligonucleotide probes.

Use of Double-Strand Cleaving Agents in the Performance of the Method

In this example we have performed a series of experiments to demonstrate the use of double-strand cleaving agents for the performance of the method using a variety of different enzymes and approaches. We have demonstrated that restriction endonucleases that are capable of cleaving both strands of double-stranded DNA can exhibit a strand preference that permits them to function as nicking agents. We have also demonstrated that such restriction endonucleases can also function as nicking agents when one of the two cleavage sites within the double-stranded nucleic acid is not capable of being cleaved by use of a truncated template or a modification to protect it from nuclease cleavage, e.g. by use of a phosphorothioate (PTO) internucleotide bond.

In order to demonstrate the use of double-strand cleaving agents as nicking agents we have performed a series of probe cleavage reactions with oligonucleotide probes containing various permutations of the restriction recognition sequence and cleavage site(s) of three double-strand cleaving restriction endonucleases: FokI (NEB), BbsI (NEB) and BccI (NEB).

Firstly, we designed oligonucleotide probes for FokI and BbsI wherein the cleavage site of either the top or the bottom strand was protected by use of a PTO. We also synthesised the truncated template variant and the full-length unmodified form of each oligonucleotide probe. Cleavage reactions were assembled with 5 pmol of each oligonucleotide probe, 5 U of the relevant enzyme, 1 µl of 10× Cutsmart buffer (NEB), 0.05 pmol of a reverse complement oligonucleotide as the target (PTO modified, or truncated template (TT)

variant as appropriate) and dH$_2$O to a final reaction volume of 10 µl. A control with no target was also performed. Reactions were incubated for 1 hour at the recommended assay temperature.

Figure 15A:
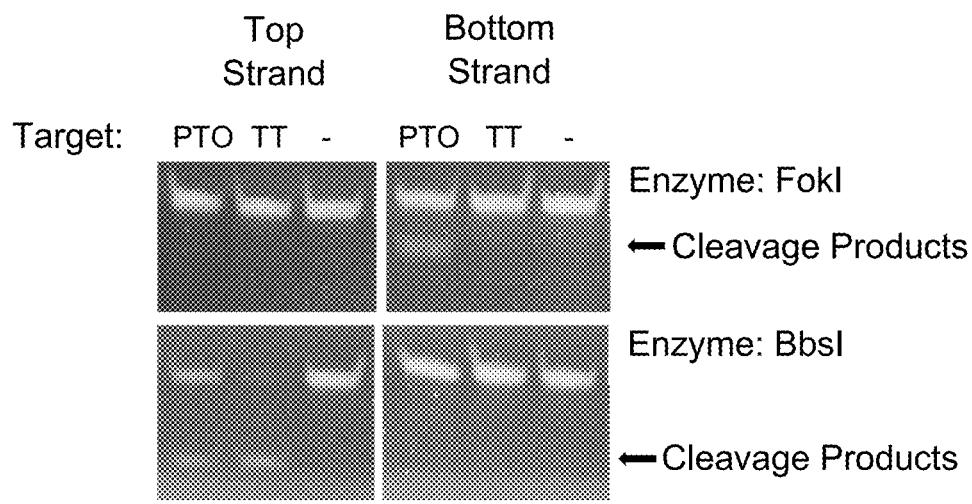
FIG. 15A, FIGS. 15B and 15C. Use of double-strand cleaving agents in the performance of the method (see Example 3).

The results are shown in FIG. 15A, with lanes loaded as indicated. In the case of FokI, oligonucleotide probe cleavage was only observed with the bottom strand, demonstrating the strand preference of the FokI enzyme. In contrast BbsI demonstrated a 'top' strand preference. Strikingly in the case of BbsI, almost complete digestion of the oligonucleotide probe was observed in the reaction in which the top strand truncated template was used. Further cleavage reactions were performed for FokI bottom strand cleavage at 0.5 pmol and 0.05 pmol of template following the same protocol. The results are displayed on FIG. 15B and demonstrate that, whilst the enzyme does yield detectable signal solely as a result of strand preference, the sensitivity of the reaction is further enhanced by use of the PTO template. Taken together, these experiments demonstrate that double strand cleaving agents such as FokI and BbsI can be employed as nicking agents for the performance of the method as a result of their strand preference, by use of PTO and/or a truncated template.

Figure 15B:
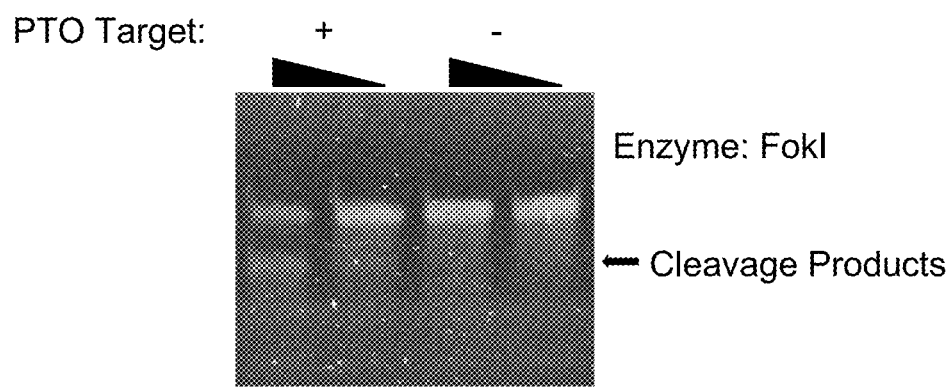
Figure 15C:
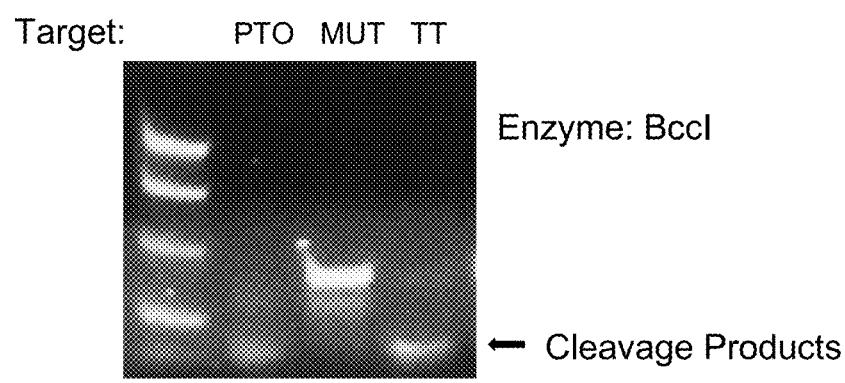

In a similar experiment we have also demonstrated that BccI can also be employed as a nicking agent using either a truncated template or a template which has been PTO modified. Digestion reactions were performed containing 5 pmol an oligonucleotide probe, P21, containing the top strand of the BccI restriction recognition and cleavage site, 0.05 pmol of either a PTO protected template (P22), a mutated form of the PTO protected template (P23) or a truncated template variant of the template (P24), 5 U BccI (NEB), 1 µl of 10× Cutsmart buffer (NEB) and dH$_2$O to a reaction volume of 10 µl. Results are shown in FIG. 15B. The first lane was loaded with a size marker. The second lane was loaded with the reaction containing the full length PTO modified template, the third with the equivalent template containing a single base mismatch in the recognition sequence and the fourth lane with the reaction where a truncated template was used. Oligonucleotide probe cleavage bands were clearly visible in the first and fourth lanes but not the third lane, demonstrating that BccI can also efficiently utilise a truncated template or a PTO modified template and function as a nicking agent for use in the method.

This example demonstrates that double strand cleaving restriction endonucleases can function efficiently as nicking agents for use in the method, using strand preference, a truncated template and/or modification of the oligonucleotide backbone to make it resistant to nuclease cleavage, e.g. by use of phosphorthioate internucleotide linkage(s). The impact of these results is highly significant in that many double-strand cleaving restriction endonucleases, of which a much greater number are characterised and/or commercially available compared to nicking endonucleases, can thus be readily employed as nicking agents for use in the method. Therefore a much wider range of enzymes can be considered during assay development, which assists the targeting of particular target sequences and selection of enzymes with appropriate properties (e.g. rate, temperature optimum) for a particular purpose.

Oligonucleotide Probe Cleavage by Five Distinct Nicking Endonucleases

Figure 16A:
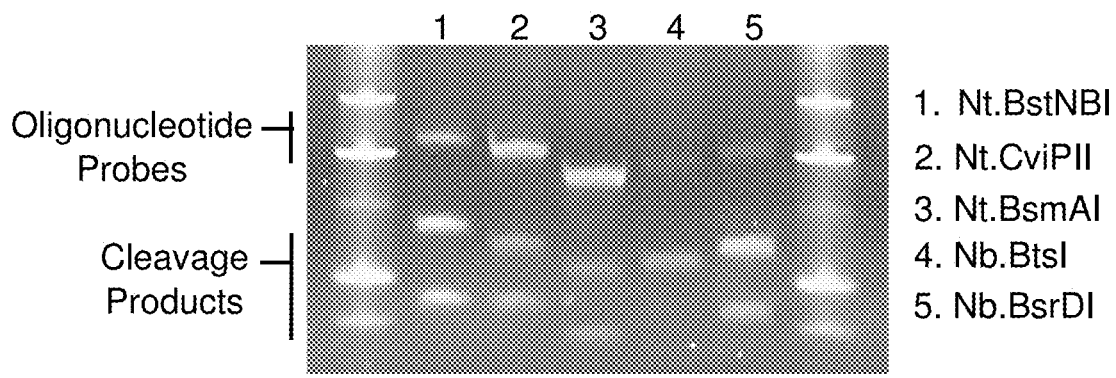
FIG. 16A. Oligonucleotide probe cleavage by five distinct nicking endonucleases (see Example 3).

In order to investigate the suitability of various nicking agents for the performance of the method, we carried out oligonucleotide probe cleavages with a panel of five commercially available nicking endonucleases. Digestion reactions were assembled for each enzyme with an associated oligonucleotide probe containing the relevant recognition site and following the manufacturers recommended reaction conditions. Reactions for each enzyme were assembled with a total of 10 ng of the M13mp18 template or in the case of the Nb.BtsI reaction, 0.5 pmol of oligonucleotide probe, P25. Reaction components were added as follows; Nt.BstNBI digestion—5 pmol of oligonucleotide probe P17, 5 U Nt.BstNBI (NEB), 1 µl of 10×NEB buffer 3.1 (NEB), 1 µl of M13mp18 and dH$_2$O to a final reaction volume of 10 µl. The reaction was incubated at 55° C. for one hour. Nt.CviPII digestion—5 pmol of oligonucleotide probe P10, 5 U Nt.CviPII (NEB), 1 µl of 10×NEB buffer 3.1 (NEB), 1 µl of M13mp18 and dH$_2$O to a final reaction volume of 10 µl. The reaction was incubated at 45° C. for one hour. Nt.BsmAI digestion—5 pmol of oligonucleotide probe P26, 5 U Nt.BsmAI (NEB), 1 µl of 10×NEB buffer 3.1 (NEB), 1 µl of M13mp18 and dH$_2$O to a final reaction volume of 10 µl. The reaction was incubated at 55° C. for one hour. Nb.BtsI digestion—5 pmol of oligonucleotide probe P27, 5 U Nb.BtsI (NEB), 1 µl of 10×NEB buffer 3.1 (NEB), 1 µl of P25 and dH$_2$O to a final reaction volume of 10 µl. The reaction was incubated at 55° C. for one hour. Nb.BsrDI digestion—5 pmol of oligonucleotide probe P28, 5 U Nb.BsrDI (NEB), 1 µl of 10×NEB buffer 3.1 (NEB), 1 µl of M13mp18 and dH$_2$O to a final reaction volume of 10 µl. The reaction was incubated at 55° C. for one hour. The digestion products of each reaction were analysed by TBE-Urea polyacrylamide gel electrophoresis (PAGE) using a 15% w/v gel stained with SYBR Gold (Life Technologies) and visualised using a transilluminator, (FIG. 16A). Each nicking endonuclease demonstrated efficient M13mp18 mediated probe cleavage and target recycling in all cases, as evidenced by the presence of bands corresponding to the expected size of cleavage products in each lane of the gel. This example demonstrates the potential to use a number of nicking endonucleases in the method.

Low Temperature Oligonucleotide Probe Cleavage

Figure 16B:
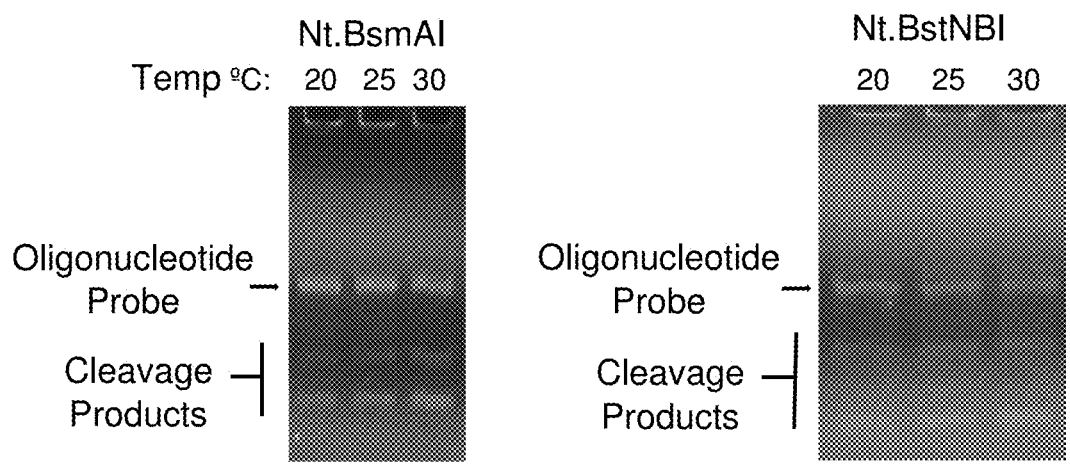
FIG. 16B. Low temperature oligonucleotide probe cleavage (see Example 3).

Temperature is thought to have an influence on the rate of the oligonucleotide probe cleavage reactions, due to the thermal optima of the nicking agents used and the respective melting temperature of the probe and the cleavage products. The majority of commercially available nicking endonucleases are recommended to have heated reactions (see Table 1). To determine the ability of certain enzymes to exhibit activity at low temperature, we performed oligonucleotide probe cleavage reactions at low temperatures. Reactions were prepared containing 5 pmol oligonucleotide probe (P3 for Nt.BstNBI or P7 for Nt.BsmAI), 5 U Nt.BstNBI or Nt.BsmAI, 0.5 pmol oligonucleotide target nucleic acid and dH$_2$O to a final volume of 10 µl. Reactions were incubated at 20° C., 25° C. or 30° C. for 1 hour and the entirety of each reaction was analysed by TBE-Urea PAGE (15% w/v gel), FIG. 16B. Surprisingly, efficient probe cleavage was demonstrated using both nicking endonucleases at 20° C. (lane 1), 25° C. (lane 2) and 30° C. (lane 3). Furthermore, there is evidence of target recycling at low temperatures. This example demonstrates that it would be possible to perform the present invention without heating the probe cleavage reactions. It is anticipated that the exponential signal amplification effect of the method will off-set the reduction in rate resulting from performing probe cleavage reactions below their optimum temperature.

Attachment of Oligonucleotide Probes to Solid Materials

In order for optimal performance of the method, oligonucleotide probes can be covalently attached to a large variety of solid materials. Magnetic beads are one common commercially available material, routinely used for conjugation of biomolecules through a number of different linkers (see detailed description). In order to demonstrate an additional solid material for oligonucleotide probe conjugation, we optimised a coupling procedure for carboxylic acid beads to oligonucleotide probes in the present example. Furthermore, we demonstrate a straightforward hybridisation technique for a simple, semi-quantitative measurement of the quantity of oligonucleotide present on a bead conjugate. This method is generally applicable in terms of measuring the efficiency of this or a number of other coupling procedures of oligonucleotides to solid materials. It is also useful to determine the amount of hybridisation competent probe available on a solid material.

Figure 17:
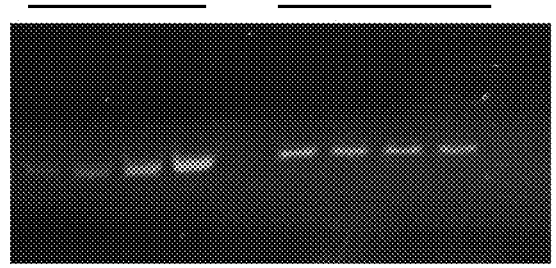
FIG. 17. Attachment of oligonucleotide probes to solid materials (see Example 3).

First, we performed four oligonucleotide conjugation reactions using Dynabeads (MyOne Carboxylic Acid beads, Life technologies) and one of four variants of an oligonucleotide probe (P13) which each contained a 5' amine modification. Each variant probe sequentially differed in length by the inclusion of a 5' C18 spacer (P13), a 5' C18 spacer and four additional thymine nucleotides (P29), or a 5' C18 spacer and eight additional thymine nucleotides (P30). The conjugation reactions were performed as described in the general methods section. Following this, 0.05 mg of each oligonucleotide-bead conjugate and a non-conjugated bead control, were aliquoted to new tubes, beads were pelleted magnetically and the supernatant removed. The beads were re-suspended in 10 µl of a 1×PBS (1.7 mM $KH_2PO_4$, 5 mM $Na_2HPO_4$, 0.5 M NaCl, pH 7.4) containing 100 pmol of a complimentary nucleotide, P2. The mixture was heated at 65° C. for ten minutes and then left to cool slowly to room temperature over the course of forty five minutes. Next, the beads were magnetically pelleted, the supernatant removed and replaced with 1000 of ice cold 1×PBS (1.7 mM $KH_2PO_4$, 5 mM $Na_2HPO_4$, 0.5 M NaCl, pH 7.4), the bead suspension was mixed by gently agitation for two minutes and this wash procedure was repeated a total number of four times to remove excess complimentary oligonucleotide. Finally, the beads were pelleted, supernatant removed and the pellet re-suspended in a final volume of 10 µl of 100 mM phosphate buffer (pH 7.2). The mixture was heated to 80° C. for 10 minutes to dissociate the complementary bound oligonucleotide from the covalently attached oligonucleotide probe conjugated to the beads. Following this, each eluate from the final step was analysed by TBE-Urea polyacrylamide gel electrophoresis (PAGE) using a 15% w/v gel stained with SYBR Gold (Life Technologies) and visualised using a UV transilluminator. Results are displayed in FIG. 17. A serial dilution (FIG. 17; lanes 1-4) of the complimentary oligonucleotide, P2, was also loaded on the gel in order to semi quantitatively determine the hybridisation capacity of the conjugated carboxylic acid beads. No complimentary oligonucleotide was detectable in the negative control (lane 5) while each bead conjugates (0.05 mg) demonstrated the capacity to retain approximately 2 pmol of complimentary oligonucleotide probe (FIG. 17, lanes 6-9). The example evidences another material appropriate for covalent attachment of oligonucleotide probes to solid material and also a method with which to semi-quantitatively determine the hybridisation capacity of a material conjugated with oligonucleotide probes of general utility in preparation of reagents for the performance of the method.

Detection of Two or More Target Nucleic Acids in the Same Sample

Figure 18A:
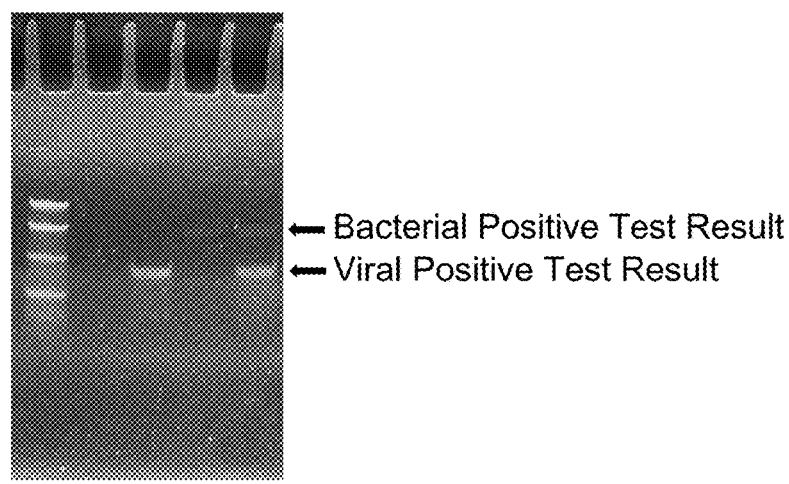
FIG. 18A, FIG. 18B and FIG. 18C. Detection of two or more target nucleic acids in the same sample (see Example 3).
Figure 18B:
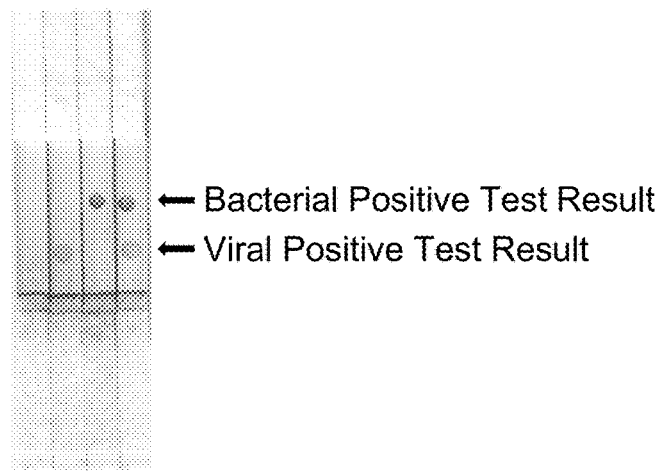

The method of the invention may be readily used to differentially detect two of more target nucleic acids in the same sample. In this example we have performed simultaneous detection of a bacterial and a viral target in the same sample. For each of the bacterial and the viral target an oligonucleotide probe was designed with complementarity to a particular site within the target sequence and containing the recognition sequence and cleavage site for a nicking agent. A different double-strand cleaving restriction endonuclease was employed for each of the targets. The oligonucleotide probes were each conjugated to beads following standard protocols. Reactions were performed containing approximately 50 µg of beads for each oligonucleotide probe, 1 µl of 10× Isothermal reaction buffer (NEB), 5 U of each enzyme, 0.25 pmol of each target nucleic acid sequence (either the bacterial target, the viral target or both together) and $dH_2O$ to a final volume of 10 µl Reactions were incubated at 50° C. for 1 hour and the entire reaction was subsequently analysed by TBE-Urea PAGE (15% w/v gel) (FIG. 18A). Reactions were also analysed by carbon nucleic acid lateral flow (FIG. 18B) wherein the strips were printed with two oligonucleotides in discrete locations, one complementary to the probe fragment that would be produced from the viral target beads and the other complementary to the probe fragment that would be produced from the bacterial target beads. 60 µl of running buffer was added to each reaction and the entire volume was applied to the sample pad of a lateral flow strip, which were photographed following signal development.

The first reaction contained neither template and consequently no signal was observed on the gel or on the lateral flow strip. The second reaction contained the viral target only and produced only the probe fragment from the beads conjugated with the oligonucleotide complementary to the viral target. The third reaction contained the bacterial target only and produced only the probe fragment from the beads conjugated with the oligonucleotide complementary to the bacterial target. The fourth reaction contained both viral and bacterial targets and thus both probe fragments were detected.

This example provides a powerful demonstration that multiple targets can be detected simultaneously in the same sample by addition of multiple different oligonucleotide probes. Furthermore, the carbon nucleic acid lateral flow assay provides a powerful opportunity for rapid multiplex detection of different targets by colour signal change, by virtue of differential hybridisation of the single-stranded probe fragments produced in the method to their complementary oligonucleotide immobilised on the lateral flow strip.

Figure 18C:
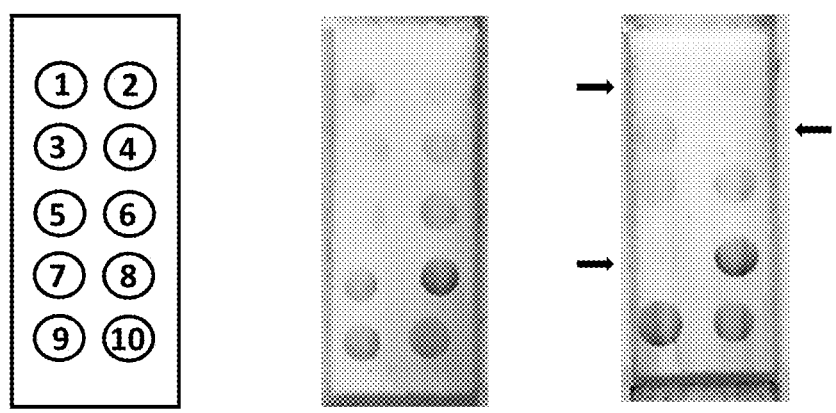

In order to further demonstrate the capability of the method for detection of multiple targets by colorimetric lateral flow assay we have developed a 10-plex assay, comprising ten probe fragments of different sequence with their reverse complementary sequence immobilised on a lateral flow strip. The lateral flow strip was prepared as described in the general methods section. Each of the complementary oligonucleotides was printed at a defined location on lateral flow strips and immobilised by UV crosslinking. 0.1 pmol of each of ten probe fragments attached to a biotin moiety were added 70 µl of running buffer and applied to the sample pad. A control strip was prepared in which three of these probe fragments were omitted on a random basis. Results were recorded by photography following signal development and are displayed in FIG. 18C. All ten probe fragments were detected by clear colour signal change at the expected location. On the control strip, no signal was detected at the position of the three omitted probe fragments (indicated by arrows), demonstrating the integrity of the hybridisation based signal location. This experiment clearly demonstrates the powerful multiplexing capability of the method of the invention for use in a low-cost, rapid, colorimetric nucleic acid lateral flow assay format. In certain applications of the method it is frequently required to detect multiple targets in the same sample, for example, when there are multiple potential causes of a disease, or in order to derive genetic sequence information regarding a number of different sites within the genome of an organism. The method of the invention is particularly amenable to multiplex detection due to the generation of single-stranded probe fragments which can be separated from the other reaction components via a lateral flow membrane and differentially detected at particular locations via hybridisation based localisation.

Example 4

Performance of the Method for a Fast, Sensitive Detection of a Target Nucleic Acid Sequence with a Colorimetric Readout This example describes how we would perform sensitive and rapid detection of target nucleic acid in a single pot reaction using three oligonucleotide probes attached to a solid material and a colorimetric read-out. The reaction would comprise three oligonucleotide probes each attached to a solid material, wherein all three oligonucleotides utilise the same nicking agent and buffer. The oligonucleotide probes would be provided in increasing amounts such that the third probe is present at >1 pmol. The third oligonucleotide probe would also be attached to a colorimetric dye, such as a gold or carbon nanoparticle, or to a moiety enabling its subsequent attachment to a colorimetric dye. The reaction would be triggered by the addition of the target nucleic acid, and would occur at room temperature. The reaction would be performed in 10-50 µl volume. After a reaction of 10 minutes a colour signal would be visible in the reaction tube because gold nanoparticles that had initially been bound to the third oligonucleotide probe would be released into solution attached to the third probe fragment. The presence of colorimetric signal in the reaction would then be determined by eye, by quantification of the absorbance of the reaction supernatant. Alternatively, a lateral flow device could be employed which may further integrate a region of complementarity to the third probe fragment to allow its specific detection. Such a lateral flow device would have further potential for multiplexed reactions because complementary sequences to a range of oligonucleotide probes could be immobilised on the lateral flow membrane at defined spatial locations. Such an example would provide a sensitive and fast detection method for target nucleic acid detection with minimal components and which exploits the exponential amplification effect of the method and combines it with the simplicity of a colorimetric signal change in the presence of target nucleic acid.

Example 4.1

Sensitive Detection of a Viral Nucleic Acid Target by Nucleic Acid Lateral Flow

Figure 19:
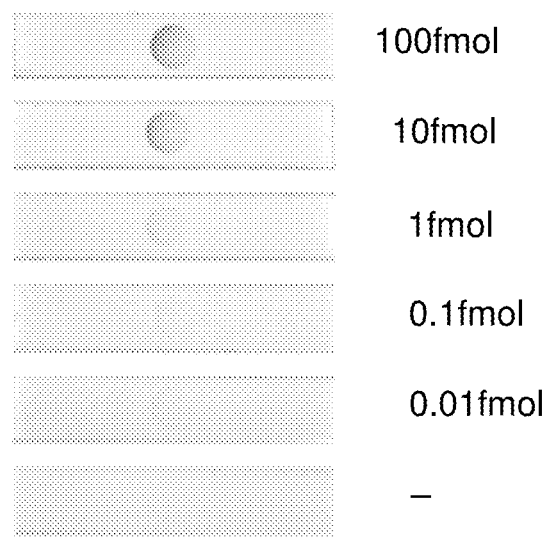
FIG. 19. Sensitive detection of a viral nucleic acid target by nucleic acid lateral flow (see Example 4.1).

This example demonstrates the application of the invention to the detection of a viral nucleic acid target. Three oligonucleotide probes in a sequential series were prepared for the performance of the method. The first of these oligonucleotide probes was designed to contain a region complementary to the target nucleic acid and to also contain the recognition sequence and cleavage site of a double strand cleaving restriction endonuclease. All three oligonucleotide probes in the sequential series were designed to function with the same enzyme. Lateral flow strips were prepared following the protocol described in the general methods section, printed with an oligonucleotide probe of a sequence complementary to the probe fragment that would be produced following cleavage of the third oligonucleotide probe. The oligonucleotide probes were conjugated to beads using standard methods. Reactions were assembled containing 1 µg of beads attached to oligonucleotide 1, 2 µg of beads attached to oligonucleotide 2 and 20 µg of beads attached to oligonucleotide 3, 1 µl of 10× reaction buffer, 20 U of restriction enzyme, various amounts of viral target nucleic acid sequence and $dH_2O$ to a total volume of 10 µl. Reactions were incubated at 25° C. for 1 hour 20 min. 60 µl running buffer was then added and the entire contents of each reaction was applied to the sample pad of a lateral flow strip. Following signal development, the lateral flow strips were photographed (FIG. 19). Signal was clearly visible at the lowest sensitivity tested, being 10 amol of viral nucleic acid target. Furthermore, the colorimetric signal appears to correspond to the level of nucleic acid target in a quantitative assay. This example demonstrates that the method of the invention can be applied to the sensitive, rapid detection of target nucleic acids in a colorimetric assay under ambient conditions and is therefore highly attractive for application to low-cost, diagnostic devices.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

Additional aspects of the invention include those listed below:
1. A method for detecting the presence of a target nucleic acid of defined sequence in a sample which method comprises the steps:
    a) contacting said sample with:
        i. a first oligonucleotide probe; and
        ii. a nicking agent;
        wherein the first oligonucleotide probe comprises a first complementarity region capable of sequence specific hybridisation to the target nucleic acid and a cleavage site for the nicking agent; and wherein the nicking agent specifically recognises double-stranded nucleic acid formed when the first oligonucleotide probe hybridises to the target nucleic acid in said sample and cleaves said first oligonucleotide probe to produce a first probe fragment;

b) contacting said first probe fragment with:
   iii. a second oligonucleotide probe; and
   iv. a nicking agent;
   wherein the second oligonucleotide probe comprises a second complementarity region capable of sequence specific hybridisation to the first probe fragment, a cleavage site for the nicking agent; and wherein the nicking agent specifically recognises double-stranded nucleic acid formed when the second oligonucleotide probe hybridises to the first probe fragment and cleaves said second oligonucleotide probe to produce a second probe fragment;
c) optionally contacting said second probe fragment with:
   v. a third oligonucleotide probe; and
   vi. a nicking agent;
   wherein the third oligonucleotide probe comprises a third complementarity region capable of sequence specific hybridisation to the second probe fragment, a cleavage site for the nicking agent; and wherein the nicking agent specifically recognises double-stranded nucleic acid formed when the third oligonucleotide probe hybridises to the second probe fragment and cleaves said third oligonucleotide probe to produce a third probe fragment;
d) optionally repeating step c) n times, wherein n is a positive integer, using fourth and subsequent sequential (3+n)th oligonucleotide probe(s) to produce fourth and subsequent sequential (3+n)th probe fragment(s); and
e) detecting the presence of the probe fragment produced at the end of step (a) and/or step (b) and/or step (c) and/or step (d) wherein the presence of said fragment(s) indicates the presence of the target nucleic acid in said sample.

2. A method according to aspect 1 wherein at least one of the oligonucleotide probes is attached to a solid material.

3. A method according to aspect 1 wherein at least one of the oligonucleotide probes is attached to a moiety that permits attachment of said oligonucleotide probe to a solid material.

4. A method according to any of aspects 1 to 3 wherein the probe fragment produced from the oligonucleotide probe in one or more of steps (a), (b), and optional steps (c) and (d), is separated from said oligonucleotide probe on the basis of its physicochemical properties, such as its size, sequence or charge, prior to the performance of the subsequent step.

5. A method according to any of aspects 1 to 4 wherein two or more of steps (a), (b), (e), and optional steps (c) and (d) are performed simultaneously.

6. A method according to any of aspects 1 to 5 wherein two or more of the nicking agents in different steps (a), (b), and optional steps (c) and (d) are the same.

7. A method according to any of aspects 1 to 6 wherein one or more of the probe fragments produced in different steps (a), (b), and optional steps (c) and (d) is attached to a moiety that permits its detection, such as a colorimetric or fluorometric dye.

8. A method according to aspect 7 wherein said moiety is an enzyme that yields a detectable signal, such as a colorimetric or fluorometric signal, following contact with a substrate.

9. A method according to aspect 8 wherein said substrate is insoluble in water.

10. A method according to any of aspects 1 to 6 wherein the presence of the probe fragment(s) in step (e) is detected electrically, such as by a change in impedance resulting from the cleavage of one or more of the oligonucleotide probe(s).

11. A method according to any of aspects 1 to 10 wherein the level of target nucleic acid in said sample is quantified in step (e).

12. A method according to any of aspects 1 to 11 wherein no DNA polymerase is used.

13. A method according to any of aspects 1 to 12 wherein at least one oligonucleotide probe fragment in the sequential series of steps (a), (b), and optional steps (c) and (d) is capable of sequence specific hybridisation to the complementarity region of one of the preceding oligonucleotide probes.

14. A method according to any one of aspects 1 to 13 wherein one or more of the nicking agents in steps (a) and (b) and optional steps (c) and (d) is a naturally occurring enzyme, such as a nicking restriction endonuclease.

15. A method according to any one of aspects 1 to 13 wherein one or more of the nicking agents in steps (a) and (b) and optional steps (c) and (d) is an engineered enzyme, such as a mutated form of a naturally occurring enzyme or a DNAzyme.

16. A method according to any of aspects 1 to 13 wherein one or more of the nicking agents in steps (a), (b), and optional steps (c) and (d) is a programmable nicking enzyme.

17. A method according to any of aspects 1 to 16 wherein said target nucleic acid is single-stranded RNA, including single-stranded RNA derived from double-stranded RNA, or single-stranded DNA, including single-stranded DNA derived from double-stranded DNA.

18. A method according to any of aspects 1 to 17 wherein said target nucleic acid is the product of reverse transcriptase, or a DNA polymerase.

19. A method according to any of aspects 1 to 17 wherein said target nucleic acid is a probe fragment produced following cleavage of an oligonucleotide probe by a restriction enzyme other than a nicking agent.

20. A method according to any of aspects 1 to 19 wherein said sample is a biological sample, such as a nasal or nasopharyngeal swab or aspirate, blood or a sample derived from blood, or urine.

21. A method according to any of aspects 1 to 20 wherein said target nucleic acid is viral or derived from viral nucleic acid material.

22. A method according to any of aspects 1 to 20 wherein said target nucleic acid is bacterial or derived from bacterial nucleic acid material.

23. A method according to any of aspects 1 to 20 wherein said target nucleic acid is circulating, cell-free DNA released from cancer cells.

24. A method according to any of aspects 1 to 20 wherein said target nucleic acid is circulating, cell-free DNA released from foetal cells.

25. A method according to any of aspects 1 to 20 or wherein said target nucleic acid is micro RNA or derived from micro RNA.

26. A method according to any of aspects 1 to 25 wherein the region of the target nucleic acid capable of sequence specific hybridisation to the first complementarity region contains a site of epigenetic modification, such as methylation.
27. A method according to any of aspects 1 to 26 wherein the detection of said target nucleic acid is used for the diagnosis, prognosis or monitoring of disease or a diseased state.
28. A method according to aspect 27 wherein said disease is an infectious disease, including but not limited to HIV, influenza, tuberculosis, meningitis, hepatitis, MRSA, Ebola, *Clostridium difficile*, Epstein barr virus, malaria, plague, polio, *Chlamydia*, herpes, gonorrhoea, measles, mumps, rubella, cholera and smallpox.
29. A method according to aspect 27 wherein said disease is a cancer, including but not limited to colorectal cancer, lung cancer, breast cancer, pancreatic cancer, prostate cancer, liver cancer, bladder cancer, leukaemia, esophageal cancer, ovarian cancer, kidney cancer, stomach cancer and melanoma.
30. A method according to any of aspects 1 to 29 wherein the detection of said target nucleic acid is used for human genetic testing, prenatal testing, blood contamination screening, pharmacogenomics or pharmacokinetics.
31. A method according to any of aspects 1 to 30 wherein the presence of two or more different target nucleic acids of defined sequence are detected in the same sample.
32. A method according to any of aspects 1 to 31 wherein said sample is any of the following: a forensic sample, an agricultural sample, a veterinary sample, an environmental sample or a biodefence sample.
33. An oligonucleotide probe comprising:
    a. a first complementarity region capable of sequence specific hybridisation to a target sequence to form double-stranded nucleic acid that is specifically recognised by a nicking agent and that contains the cleavage site for said nicking agent; and
    b. a further complementarity region which is capable of sequence specific hybridisation to another oligonucleotide probe to form a double-stranded nucleic acid that is specifically recognised by a nicking agent, and that contains the anti-sense sequence of the cleavage site for said nicking agent.
34. An oligonucleotide according to aspect 33 wherein said oligonucleotide probe is attached to a solid material.
35. An oligonucleotide according to aspect 33 wherein said oligonucleotide probe is attached to a moiety that permits attachment of said oligonucleotide probe to a solid material.
36. A kit containing an oligonucleotide according to any of aspects 33 to 35 together with instructions for the performance of the method according to any of aspects 1 to 32.
37. A kit containing the following:
    a. A first oligonucleotide probe comprising:
        i. a complementarity region [A] capable of sequence specific hybridisation to a target sequence to form double-stranded nucleic acid that is specifically recognised by a nicking agent and that contains the cleavage site for said nicking agent; and
        ii. a further complementarity region [B] which is capable of sequence specific hybridisation to a second oligonucleotide probe to form a double-stranded nucleic acid that is specifically recognised by a nicking agent, and that contains the anti-sense sequence of the cleavage site for said nicking agent;
    and
    b. A second oligonucleotide probe comprising a complementarity region [C] capable of sequence specific hybridisation to the complementarity region [B] in said first oligonucleotide probe to form a double-stranded nucleic acid that is specifically recognised by a nicking agent and that contains the cleavage site for said nicking agent.
38. A kit according to aspect 37 wherein one or both of said oligonucleotide probes is attached to a solid material.
39. A kit according to aspect 37 wherein one or both of said oligonucleotide probes is attached to a moiety that permits attachment of said oligonucleotide probe(s) to a solid material.
40. A method for detecting the presence of a target nucleic acid of defined sequence in a sample which method comprises the steps:
    a) contacting said sample with:
        i. an oligonucleotide probe attached to an enzyme; and
        ii. a nicking agent;
        wherein the oligonucleotide probe comprises a complementarity region capable of sequence specific hybridisation to the target nucleic acid and a cleavage site for the nicking agent; and wherein the nicking agent specifically recognises double-stranded nucleic acid formed when the oligonucleotide probe hybridises to the target nucleic acid in said sample and cleaves said oligonucleotide probe to produce a probe fragment attached to said enzyme; and
    b) detecting the presence of the probe fragment produced at the end of step (a) by contacting said enzyme with a substrate that yields a colorimetric or fluorometric signal following action of the enzyme, wherein the presence of signal indicates the presence of the target nucleic acid in said sample. In this aspect of the invention an exponentially increasing colorimetric or fluorometric signal is produced in the presence of target nucleic acid without requirement for a DNA polymerase and without requirement for a second or subsequent oligonucleotide probe.
41. A method according to aspect 40 wherein said oligonucleotide probe is attached to a solid material.
42. A method according to aspect 40 wherein said oligonucleotide probe is attached to a moiety that permits attachment of said oligonucleotide probe to a solid material.
43. A method according to any of aspects 40 to 42 wherein said substrate is insoluble in water.
44. A method according to any of aspects 40 to 43 wherein said target nucleic acid is the product of reverse transcriptase or a DNA polymerase.
45. A method according to any of aspects 40 to 44 wherein the level of target nucleic acid in said sample is quantified in step (b).
46. A method according to any of aspects 40 to 45 wherein the detection of said target nucleic acid is used for the diagnosis, prognosis or monitoring of disease or a diseased state.
47. An oligonucleotide probe attached to an enzyme that yields a detectable signal, such as a colorimetric or fluorometric signal, following exposure of said enzyme to a substrate; and wherein said oligonucleotide probe comprises a complementarity region capable of sequence specific hybridisation to form a double-stranded nucleic acid that is specifically recognised by a nicking agent and that contains the cleavage site for said nicking agent.

48. A kit containing an oligonucleotide probe according to aspect 47 together with instructions for the performance of the method of any of aspects 40 to 46.

49. A kit containing an oligonucleotide probe according to aspect 46 together with a nicking agent.

50. A method for detecting the presence of a target nucleic acid of defined sequence in a sample which method comprises the steps:
   a) contacting said sample with:
      i. an oligonucleotide probe attached to a solid material; and
      ii. a nicking agent;
      wherein the oligonucleotide probe comprises a complementarity region capable of sequence specific hybridisation to the target nucleic acid and a cleavage site for the nicking agent; and wherein the nicking agent specifically recognises double-stranded nucleic acid formed when the oligonucleotide probe hybridises to the target nucleic acid in said sample and cleaves said oligonucleotide probe to produce two probe fragments; and
   b) detecting the cleavage of the oligonucleotide probe at the end of step (a) by electrical signal, such as a change in impedance, wherein the presence of signal indicates the presence of the target nucleic acid in said sample.

51. A method according to aspect 50 wherein the level of target nucleic acid in said sample is quantified in step (b).

52. A method according to aspect 50 or 51 wherein the detection of target nucleic acid is used for the diagnosis, prognosis or monitoring of disease or a diseased state.

53. A method for detecting the presence of a target nucleic acid of defined sequence in a sample which method comprises:
   a) contacting said sample with:
      i. an oligonucleotide probe attached to a colorimetric dye and attached to a solid material; and
      ii. a nicking agent;
      wherein the oligonucleotide probe comprises a complementarity region capable of sequence specific hybridisation to the target nucleic acid and a cleavage site for the nicking agent; and wherein the nicking agent specifically recognises double-stranded nucleic acid formed when the oligonucleotide probe hybridises to the target nucleic acid in said sample and cleaves said oligonucleotide probe to produce a probe fragment attached to said colorimetric dye; and
   b) detecting the presence of the probe fragment attached to colorimetric dye produced at the end of step (a) by colorimetric signal detection, wherein the presence of signal indicates the presence of the target nucleic acid in said sample.

54. A method according to aspect 53 wherein the detection of target nucleic acid is used for the diagnosis, prognosis or monitoring of disease or a diseased state.

55. An oligonucleotide probe attached to a colorimetric dye and attached to a solid material; wherein said oligonucleotide probe comprises a complementarity region capable of sequence specific hybridisation to form double-stranded nucleic acid that is specifically recognised by a nicking agent and that contains the cleavage site for said nicking agent.

56. A kit containing an oligonucleotide according to aspect 55 together with instructions for the performance of the method of aspect 53 or 54.

57. A method for detecting the presence of a target nucleic acid of defined sequence in a sample which method comprises the steps:
   a) contacting said sample with:
      i. a first oligonucleotide probe attached to a solid material; and
      ii. a nicking agent;
      wherein the first oligonucleotide probe comprises a first complementarity region capable of sequence specific hybridisation to the target nucleic acid and a cleavage site for the nicking agent; and wherein the nicking agent specifically recognises double-stranded nucleic acid formed when the first oligonucleotide probe hybridises to the target nucleic acid in said sample and cleaves said first oligonucleotide probe to release a first probe fragment from said solid material;
   b) contacting said first probe fragment with:
      iii. a second oligonucleotide probe attached to a solid material; and
      iv. a nicking agent;
      wherein the second oligonucleotide probe comprises a second complementarity region capable of sequence specific hybridisation to the first probe fragment, a cleavage site for the nicking agent; and wherein the nicking agent specifically recognises double-stranded nucleic acid formed when the second oligonucleotide probe hybridises to the first probe fragment and cleaves said second oligonucleotide probe to release a second probe fragment from said solid material;
   c) contacting said second probe fragment with:
      v. a third oligonucleotide probe attached to a solid material and attached to a colorimetric dye; and
      vi. a nicking agent;
      wherein the third oligonucleotide probe comprises a third complementarity region capable of sequence specific hybridisation to the second probe fragment, a cleavage site for the nicking agent; and wherein the nicking agent specifically recognises double-stranded nucleic acid formed when the third oligonucleotide probe hybridises to the second probe fragment and cleaves said third oligonucleotide probe to release a third probe fragment attached to said colorimetric dye from said solid material; and
   d) detecting the presence of colorimetric signal in solution produced at the end of step (c) wherein the presence of said colorimetric signal indicates the presence of the target nucleic acid in said sample.

58. A kit containing the following components (a), (b), (c) and (d):
   a. A first oligonucleotide probe attached to a solid material wherein said first oligonucleotide probe comprises:
      i. a complementarity region [A] capable of sequence specific hybridisation to a target nucleic acid to form double-stranded nucleic acid that is specifically recognised by a nicking agent and that contains the cleavage site for said nicking agent; and ii. a further complementarity region [B] which is capable of acting as a target sequence for a second oligonucleotide probe and which is capable of sequence specific hybridisation to a second oligonucleotide probe to form a double-stranded nucleic acid that is specifically recognised by a nicking agent, and that contains the anti-sense sequence of the cleavage site for said nicking agent;

b. A second oligonucleotide probe attached to a solid material wherein said second oligonucleotide probe comprises:

i. a complementarity region [C] capable of sequence specific hybridisation to the complementarity region [B] in said first oligonucleotide probe to form a double-stranded nucleic acid that is specifically recognised by a nicking agent and that contains the cleavage site for said nicking agent; and ii. a further complementarity region [D] which is capable of sequence specific hybridisation to a third oligonucleotide probe to form a double-stranded nucleic acid that is specifically recognised by a nicking agent, and that contains the anti-sense sequence of the cleavage site for said nicking agent;

c. A third oligonucleotide probe attached to a solid material and attached to a colorimetric dye wherein said third oligonucleotide probe comprises a complementarity region [E] capable of sequence specific hybridisation to the complementarity region in said second oligonucleotide probe to form a double-stranded nucleic acid that is specifically recognised by a nicking agent and that contains the cleavage site for said nicking agent; and d. Nicking agent(s) capable of cleaving the first oligonucleotide probe, second oligonucleotide probe and third oligonucleotide probe.

The invention claimed is:

1. A method for detecting the presence of a target nucleic acid of defined sequence in a sample which method comprises the steps:
   a) contacting said sample with:
      i. a first oligonucleotide probe; and
      ii. a nicking agent;
      wherein the first oligonucleotide probe comprises a first complementarity region capable of sequence specific hybridisation to the target nucleic acid and a cleavage site for the nicking agent; and wherein the nicking agent specifically recognises double-stranded nucleic acid formed when the first oligonucleotide probe hybridises to the target nucleic acid in said sample and cleaves said first oligonucleotide probe to produce a first probe fragment;
   b) contacting said first probe fragment with:
      iii. a second oligonucleotide probe; and
      iv. a nicking agent;
      wherein the second oligonucleotide probe comprises a second complementarity region capable of sequence specific hybridisation to the first probe fragment and a cleavage site for the nicking agent; and wherein the nicking agent specifically recognises double-stranded nucleic acid formed when the second oligonucleotide probe hybridises to the first probe fragment and cleaves said second oligonucleotide probe to produce a second probe fragment;
   c) optionally contacting said second probe fragment with:
      v. a third oligonucleotide probe; and
      vi. a nicking agent;
      wherein the third oligonucleotide probe comprises a third complementarity region capable of sequence specific hybridisation to the second probe fragment and a cleavage site for the nicking agent; and wherein the nicking agent specifically recognises double-stranded nucleic acid formed when the third oligonucleotide probe hybridises to the second probe fragment and cleaves said third oligonucleotide probe to produce a third probe fragment;
   d) optionally repeating step c) n times, wherein n is a positive integer, using fourth and subsequent sequential (3+n)th oligonucleotide probe(s) to produce fourth and subsequent sequential (3+n)th probe fragment(s); and
   e) detecting the presence of the probe fragment produced at the end of step (b) and/or step (c) and/or step (d), wherein one or more of said detected probe fragment(s) is not capable of sequence specific hybridisation to the complementarity region of any of the preceding oligonucleotide probes to form a site that is specifically recognised and cleaved by any of the said nicking agent(s) and/or none of the probe fragments produced is capable of sequence specific hybridisation to the first complementarity region of the first oligonucleotide probe, and wherein the presence of said detected probe fragment(s) indicates the presence of the target nucleic acid in said sample.

2. A method according to claim 1, wherein none of the probe fragments produced in steps (a), (b), and optional steps (c) and (d) are capable of sequence specific hybridisation to the complementarity region of any one of the preceding oligonucleotide probes.

3. A method according to claim 1, wherein at least one of the oligonucleotide probes is attached to a solid material.

4. A method according to claim 1, wherein two or more of the nicking agents in different steps (a), (b), and optional steps (c) and (d) are the same.

5. A method according to claim 1, wherein one or more of the probe fragments produced in step (b), and optional steps (c) and (d) is attached to a moiety that permits its detection, wherein the moiety is selected from a colorimetric or fluorometric dye, and a moiety that is capable of attachment to a colorimetric dye.

6. A method according to claim 5, wherein said moiety is an enzyme that yields a colorimetric or fluorometric signal following contact with a substrate.

7. A method according to claim 1, wherein the presence of the probe fragment(s) in step (e) is detected by nucleic acid lateral flow.

8. A method according to claim 7, wherein the nucleic acid lateral flow utilises one or more nucleic acid(s) capable of sequence specific hybridisation to one or more of the probe fragments in step (e).

9. A method according to claim 7, wherein a colorimetric signal is produced with a colorimetric dye selected from the group consisting of carbon and gold.

10. A method according to claim 1, wherein the level of target nucleic acid in said sample is quantified in step (e).

11. A method according to claim 1, wherein one or more of the nicking agents in steps (a), (b), and optional steps (c) and (d) is selected from the group consisting of a nicking restriction endonuclease, an engineered enzyme, and a programmable nicking enzyme.

12. A method according to claim 1, wherein one or more of the nicking agents in steps (a), (b), and optional steps (c) and (d) is a double-strand cleaving agent which functions as a nicking agent due to i) strand preference, or ii) only one of the two strands within the double-stranded nucleic acid that is specifically recognised by said double-stranded cleaving agent being capable of cleavage.

13. A method according to claim 1, wherein one or more of the oligonucleotide probes comprises one or more modifications that render it resistant to nuclease cleavage.

14. A method according to claim 1, wherein said target nucleic acid is selected from the group consisting of single-stranded RNA, including single-stranded RNA derived from double-stranded RNA and single-stranded RNA derived from double-stranded DNA, or single-stranded DNA, including single-stranded DNA derived from double-stranded DNA, single-stranded DNA derived from double-stranded DNA by use of a nuclease, the product of reverse transcriptase, an RNA polymerase or a DNA polymerase and a probe fragment produced following cleavage of an oligonucleotide probe by a double-strand cleaving agent.

15. A method according claim 1, wherein the presence of two or more different target nucleic acids of defined sequence are detected in the same sample.

16. A method according to claim 15, wherein a separate series of steps (a), (b), optional steps (c), (d), and (e) using different first, second and optionally third, fourth and subsequent sequential (3+n)th oligonucleotide probes for each of the two or more target nucleic acids is performed, which separate series of steps may be conducted simultaneously, or wherein step (a) uses a different first oligonucleotide probe for each of the two or more different target nucleic acids but the probe fragment produced in one or more of steps (a), (b), and optional steps (c) and (d) for two or more target nucleic acids is capable of hybridising to the same oligonucleotide probe in a subsequent step.

17. A method according to claim 1, wherein said sample is selected from the group consisting of a human sample, a forensic sample, an agricultural sample, a veterinary sample, an environmental sample and a biodefence sample, including a biological sample selected from the group consisting of a nasal or nasopharyngeal swab or aspirate, blood or a sample derived from blood, and urine.

18. A method according to claim 1, wherein said target nucleic acid is viral or derived from viral nucleic acid material, is bacterial or derived from bacterial nucleic acid material, is circulating, cell-free DNA released from cancer cells or foetal cells, or is micro RNA or derived from micro RNA.

19. A method according to claim 1, wherein the detection of said target nucleic acid is used for the diagnosis, prognosis or monitoring of a disease or a diseased state, selected from the group consisting of an infectious disease, including but not limited to HIV, influenza, RSV, Rhinovirus, norovirus, tuberculosis, HPV, meningitis, hepatitis, MRSA, Ebola, *Clostridium difficile*, Epstein-Barr virus, malaria, plague, polio, *Chlamydia*, herpes, gonorrhoea, measles, mumps, rubella, cholera or smallpox, and a cancer, including but not limited to colorectal cancer, lung cancer, breast cancer, pancreatic cancer, prostate cancer, liver cancer, bladder cancer, leukaemia, esophageal cancer, ovarian cancer, kidney cancer, stomach cancer or melanoma.

20. A method for detecting the presence of a target nucleic acid of defined sequence in a sample which method comprises the steps:
   a) contacting said sample with:
      i. a first oligonucleotide probe attached to a solid material; and
      ii. a nicking agent;
      wherein the first oligonucleotide probe comprises a first complementarity region capable of sequence specific hybridisation to the target nucleic acid and a cleavage site for the nicking agent; and wherein the nicking agent specifically recognises double-stranded nucleic acid formed when the first oligonucleotide probe hybridises to the target nucleic acid in said sample and cleaves said first oligonucleotide probe to release a first probe fragment from said solid material;
   b) contacting said first probe fragment with:
      iii. a second oligonucleotide probe attached to a solid material; and
      iv. a nicking agent;
      wherein the second oligonucleotide probe comprises a second complementarity region capable of sequence specific hybridisation to the first probe fragment and a cleavage site for the nicking agent; and wherein the nicking agent specifically recognises double-stranded nucleic acid formed when the second oligonucleotide probe hybridises to the first probe fragment and cleaves said second oligonucleotide probe to release a second probe fragment from said solid material;
   c) contacting said second probe fragment with:
      v. a third oligonucleotide probe attached to a solid material and attached to a colorimetric dye or a moiety capable of attachment to a colorimetric dye; and
      vi. a nicking agent;
      wherein the third oligonucleotide probe comprises a third complementarity region capable of sequence specific hybridisation to the second probe fragment and a cleavage site for the nicking agent; and wherein the nicking agent specifically recognises double-stranded nucleic acid formed when the third oligonucleotide probe hybridises to the second probe fragment and cleaves said third oligonucleotide probe to release a third probe fragment attached to said colorimetric dye or moiety capable of attachment to a colorimetric dye from said solid material, wherein said third probe fragments is not capable of sequence specific hybridisation to the complementarity region of any one of the preceding oligonucleotide probes to form a site that is specifically recognised and cleaved by any of the said nicking agents; and
   d) detecting the presence of said third probe fragment produced at the end of step c) by colorimetric detection wherein the presence of a colorimetric signal indicates the presence of the target nucleic acid in said sample.

* * * * *